(12) United States Patent
Jackson et al.

(10) Patent No.: US 11,285,191 B2
(45) Date of Patent: Mar. 29, 2022

(54) IMMUNOSTIMULATORY COMPOSITIONS AND USES THEREFOR

(71) Applicant: The Board of Supervisors of Louisiana State University and Agricultural and Mechanical College, Baton Rouge, LA (US)

(72) Inventors: Ronald James Jackson, Australian Capital Territory (AU); Charani Ranasinghe, Australian Capital Territory (AU)

(73) Assignee: THE BOARD OF SUPERVISORS OF LOUISIANA STATE UNIVERSITY AND AGRICULTURAL AND MECHANICAL COLLEGE, Baton Rouge, LA (US)

( * ) Notice: Subject to any disclaimer, the term of this patent is extended or adjusted under 35 U.S.C. 154(b) by 138 days.

(21) Appl. No.: 16/320,586

(22) PCT Filed: Jul. 26, 2017

(86) PCT No.: PCT/AU2017/050772
§ 371 (c)(1),
(2) Date: Jan. 25, 2019

(87) PCT Pub. No.: WO2018/018082
PCT Pub. Date: Feb. 1, 2018

(65) Prior Publication Data
US 2019/0336581 A1    Nov. 7, 2019

(30) Foreign Application Priority Data

Jul. 26, 2016 (AU) ................................ 2016902939

(51) Int. Cl.
*A61K 38/20* (2006.01)
*A61K 39/012* (2006.01)
*A61K 39/04* (2006.01)
*A61K 39/21* (2006.01)
*A61K 39/295* (2006.01)
*C07K 14/54* (2006.01)
*A61P 37/04* (2006.01)
*A61P 31/18* (2006.01)
*A61K 38/17* (2006.01)
*A61K 39/00* (2006.01)

(52) U.S. Cl.
CPC .......... *A61K 38/20* (2013.01); *A61K 38/1793* (2013.01); *A61K 39/012* (2013.01); *A61K 39/04* (2013.01); *A61K 39/21* (2013.01); *A61K 39/295* (2013.01); *A61P 31/18* (2018.01); *A61P 37/04* (2018.01); *C07K 14/54* (2013.01); *A61K 2039/543* (2013.01); *A61K 2039/545* (2013.01); *A61K 2039/57* (2013.01); *A61K 2039/6031* (2013.01)

(58) Field of Classification Search
None
See application file for complete search history.

(56) References Cited

U.S. PATENT DOCUMENTS

| | | |
|---|---|---|
| 4,184,917 A | 1/1980 | Dorner et al. |
| 4,293,652 A | 10/1981 | Cohen |
| 4,321,365 A | 3/1982 | Wu et al. |
| 4,351,901 A | 9/1982 | Bahl |
| 4,671,958 A | 6/1987 | Rodwell et al. |
| 4,790,824 A | 12/1988 | Morrow et al. |
| 4,816,567 A | 3/1989 | Cabilly et al. |
| 4,945,050 A | 7/1990 | Sanford et al. |
| 5,036,006 A | 7/1991 | Sanford et al. |
| 5,064,413 A | 11/1991 | McKinnon et al. |
| 5,093,242 A | 3/1992 | Bachmair et al. |
| 5,100,792 A | 3/1992 | Sanford et al. |
| 5,122,463 A | 6/1992 | Varshavsky et al. |
| 5,139,941 A | 8/1992 | Muzyczka et al. |
| 5,173,414 A | 12/1992 | Lebkowski et al. |
| 5,179,022 A | 1/1993 | Sanford et al. |
| 5,219,740 A | 6/1993 | Miller et al. |
| 5,241,078 A | 8/1993 | Moreland et al. |
| 5,288,931 A * | 2/1994 | Chang .................. C07K 1/1133 435/69.1 |
| 5,312,335 A | 5/1994 | McKinnon et al. |
| 5,371,015 A | 12/1994 | Sanford et al. |
| 5,383,851 A | 1/1995 | McKinnon, Jr. et al. |
| 5,399,163 A | 3/1995 | Peterson et al. |
| 5,478,744 A | 12/1995 | Sanford et al. |
| 5,505,947 A | 4/1996 | Johnston et al. |
| 5,520,639 A | 5/1996 | Peterson et al. |
| 5,580,756 A | 12/1996 | Linsley et al. |
| 5,584,807 A | 12/1996 | McCabe |

(Continued)

FOREIGN PATENT DOCUMENTS

| | | |
|---|---|---|
| EP | 0500799 | 9/1992 |
| EP | 1092444 | 4/2001 |
| WO | 1989/03429 | 4/1989 |
| WO | 1991/12882 | 9/1991 |
| WO | 1992/01070 | 1/1992 |

(Continued)

OTHER PUBLICATIONS

Fenton et al. (2020, Medicinal Chemistry Research 29:1133-1146).*

(Continued)

*Primary Examiner* — Bridget E Bunner
*Assistant Examiner* — Fozia M Hamud
(74) *Attorney, Agent, or Firm* — Baker Donelson

(57) ABSTRACT

Disclosed are compositions and methods for stimulating immune responses. More particularly, these compositions and methods involve the use of an inhibitor of IL-25 function and an immune stimulator that stimulates an immune response to a target antigen for stimulating protective or therapeutic immune responses to a target antigen. The compositions and methods of the present invention are particularly useful in the prevention and treatment of infections and cancers.

14 Claims, 20 Drawing Sheets
Specification includes a Sequence Listing.

(56) References Cited

U.S. PATENT DOCUMENTS

| | | | |
|---|---|---|---|
| 5,643,576 | A | 7/1997 | Johnston et al. |
| 5,693,762 | A | 12/1997 | Queen et al. |
| 5,831,005 | A | 11/1998 | Zuckerman et al. |
| 5,843,723 | A | 12/1998 | Dubensky, Jr. et al. |
| 5,846,796 | A | 12/1998 | Cerami et al. |
| 5,865,796 | A | 2/1999 | McCabe |
| 5,993,412 | A | 11/1999 | Deily et al. |
| 6,008,035 | A | 12/1999 | Johnston et al. |
| 6,010,478 | A | 1/2000 | Bellhouse et al. |
| 6,015,686 | A | 1/2000 | Dubensky, Jr. et al. |
| 6,015,694 | A | 1/2000 | Dubensky, Jr. et al. |
| 6,072,033 | A | 6/2000 | Yao et al. |
| 6,287,556 | B1 | 9/2001 | Portnoy et al. |
| 6,352,697 | B1 | 3/2002 | Cox et al. |
| 6,562,578 | B1 | 5/2003 | Gorman et al. |
| 6,635,443 | B1 | 10/2003 | Shi et al. |
| 7,112,660 | B1 * | 9/2006 | Domingues ........ C07K 14/5406 530/351 |
| 8,658,169 | B2 | 2/2014 | Matthews et al. |
| 8,785,605 | B2 | 7/2014 | Almagro et al. |
| 9,840,557 | B2 | 12/2017 | Orengo et al. |
| 2003/0045474 | A1 * | 3/2003 | Sailer ...................... A61P 19/00 514/8.8 |
| 2012/0064073 | A1 | 3/2012 | Chen et al. |
| 2014/0154743 | A1 * | 6/2014 | Levy ...................... C07K 16/00 435/69.6 |
| 2014/0322238 | A1 | 10/2014 | Budelsky et al. |

FOREIGN PATENT DOCUMENTS

| | | |
|---|---|---|
| WO | 1992/03545 | 3/1992 |
| WO | 1993/03769 | 3/1993 |
| WO | 1998/51810 | 11/1998 |
| WO | 1999/02694 | 1/1999 |
| WO | 1999/15641 | 4/1999 |
| WO | 1999/30742 | 6/1999 |
| WO | 1999/24465 | 8/1999 |
| WO | 1999/42564 | 8/1999 |
| WO | 1999/31251 | 10/1999 |
| WO | 1999/51754 | 12/1999 |
| WO | 2000/00600 | 1/2000 |
| WO | 2000/42215 | 7/2000 |
| WO | 2000/66759 | 11/2000 |
| WO | 2001/85207 | 11/2001 |
| WO | 2001/88097 | 11/2001 |
| WO | 2008/129263 | 10/2008 |
| WO | 2015/031778 | 3/2015 |
| WO | WO 2015/031778 | * 3/2015 |

OTHER PUBLICATIONS

Alaoui-Ismaili (2009, Cytokine Growth Factor Rev. 20(5-6):501-7).*
Guo et al. (2004, PNAS USA 101(25):9205-10).*
Ulloa-Aguirre et al. (2004, Traffic 5:821-837) and Bernier et al. (2004, Curr. Opin. Pharmacol. 4:528-533).*
Bhattacharya et al. (2017, PLoS ONE 12(3): e0171355, https://doi.org/10.1371/journal.pone.0171355).*
Rossjohn, Jamie, et al. "Structure of a cholesterol-binding, thiol-activated cytolysin and a model of its membrane form." Cell 89.5 (1997): 685-692.
Sadis S, Atienza C Jr, Finley D. Synthetic signals for ubiquitin-dependent proteolysis. Mol Cell Biol. Aug. 1995;15 (8):4086-94.
Salmonellosis GenBank Accession No. L03833 2005.
Salmons, Brian, and Walter H. Gunzburg. "Targeting of retroviral vectors for gene therapy." Human gene therapy 4.2 (1993): 129-141.
Sambrook, J., E. F. Fritsch, and T. Maniatis. "Molecular cloning, A laboratory manual 3rd edition, Book 2." (2001).
Sandhu JS. Protein engineering of antibodies. Crit Rev Biotechnol. 1992;12(5-6):437-62.
Scarpa, M., et al. "Characterization of recombinant helper retroviruses from Moloney-based vectors in ecotropic and amphotropic packaging cell lines." Virology 180.2 (1991): 849-852.

Schulz, Manfred, Rolf M. Zinkernagel, and Hans Hengartner. "Peptide-induced antiviral protection by cytotoxic T cells." Proceedings of the National Academy of Sciences 88.3 (1991): 991-993.
Seth, Prem, et al. "Mechanism of enhancement of DNA expression consequent to cointernalization of a replication-deficient adenovirus and unmodified plasmid DNA." Journal of virology 68.2 (1994): 933-940.
Shastri N. Needles in haystacks: identifying specific peptide antigens for T cells. Curr Opin Immunol. Apr. 1996;8 (2):271-7.
Shelling AN, Smith MG. Targeted integration of transfected and infected adeno-associated virus vectors containing the neomycin resistance gene. Gene Ther. May 1994; 1(3):165-9.
Shigekawa, Katherine, and William J. Dower. "Electroporation of eukaryo and prokaryotes: a general approach to the introduction of macromolecules into cells." Biotechniques 6.8 (1988): 742-751.
Singer, Irwin I., et al. "Optimal humanization of 1B4, an anti-CD18 murine monoclonal antibody, is achieved by correct choice of human V region framework sequences." The Journal of Immunology 150.7 (1993): 2844-2857.
Stoltze L, Schirle M, Schwarz G, Schroter C, Thompson MW, Hersh LB, Kalbacher H, Stevanovic S, Rammensee HG, Schild H. Two new proteases in the MHC class I processing pathway. Nat Immunol. Nov. 2000;1(5):413-8.
Sturmhoefel K, Lee K, Gray GS, Thomas J, Zollner R, O'Toole M, Swiniarski H, Dorner A, Wolf SF. Potent activity of soluble B7-IgG fusion proteins in therapy of established tumors and as vaccine adjuvant. Cancer Res. Oct. 1, 1999;59 (19):4964-72.
Takamizawa, Masaru, et al. "Dendritic cells that process and present nominal antigens to naive T lymphocytes are derived from CD2+ precursors." The Journal of Immunology 158.5 (1997): 2134-2142.
Thomas, Ranjeny, and Peter E. Lipsky. "Human peripheral blood dendritic cell subsets. Isolation and characterization of precursor and mature antigen-presenting cells." The Journal of Immunology 153.9 (1994): 4016-4028.
Thurnher, M., et al. "In vitro generation of CD83+ human blood dendritic cells for active tumor immunotherapy." Experimental hematology 25.3 (1997): 232-237.
Tian, Erming, et al. "Evi27 encodes a novel membrane protein with homology to the IL17 receptor." Oncogene 19.17 (2000): 2098-2109.
Tsai, Hsing-Chuan, et al. "IL-17A and Th17 cells in lung inflammation: an update on the role of Th17 cell differentiation and IL-17R signaling in host defense against infection." Clinical and Developmental Immunology (2013).
Ulmer, Jeffrey B., et al. "Heterologous protection against influenza by injection of DNA encoding a viral protein." Science 259.5102 (1993): 1745-1749.
Van der Bruggen P, Traversari C, Chomez P, Lurquin C, De Plaen E, Van den Eynde B, Knuth A, Boon T. A gene encoding an antigen recognized by cytolytic T lymphocytes on a human melanoma. Science. Dec. 13, 1991;254 (5038):1643-7.
Vigna, Elisa, and Luigi Naldini. "Lentiviral vectors: excellent tools for experimental gene transfer and promising candidates for gene therapy." The journal of gene medicine 2.5 (2000): 308-316.
Vollenweider, Iren, and P. Groscurth. "Comparison of four DNA staining fluorescence dyes for measuring cell proliferation of lymphokine-activated killer (LAK) cells." Journal of immunological methods 149.1 (1992): 133-135.
Wagner, Ernst, et al. "Coupling of adenovirus to transferrin-polylysine/DNA complexes greatly enhances receptor-mediated gene delivery and expression of transfected genes." Proceedings of the national academy of sciences 89.13 (1992): 6099-6103.
Wallin, Reidar, Catherine Stanton, and R. Paul Ross. "Intracellular proteolytic processing of the two-chain vitamin K-dependent coagulation factor X." Thrombosis research 73.6 (1994): 395-403.
Walther, Wolfgang, and Ulrike Stein. "Viral vectors for gene transfer." Drugs 60.2 (2000): 249-271.
Wang, Dalton, and Stanford Moore. "Polyspermine-ribonuclease prepared by cross-linkage with dimethyl suberimidate." Biochemistry 16.13 (1977): 2937-2942.

(56) References Cited

OTHER PUBLICATIONS

Weissman, Drew, et al. "Three populations of cells with dendritic morphology exist in peripheral blood, only one of which is infectable with human immunodeficiency virus type 1." Proceedings of the National Academy of Sciences 92.3 (1995): 826-830.
Wenzel, Sally, et al. "Effect of an interleukin-4 variant on late phase asthmatic response to allergen challenge in asthmatic patients: results of two phase 2a studies." The Lancet 370.9596 (2007): 1422-1431.
Wolff, Jon A., et al. "Direct gene transfer into mouse muscle in vivo." Science 247.4949 (1990): 1465-1468.
Wong, Chun K., et al. "Interleukin-25-induced chemokines and interleukin-6 release from eosinophils is mediated by p38 mitogen-activated protein kinase, c-Jun N-terminal kinase, and nuclear factor-?B." American journal of respiratory cell and molecular biology 33.2 (2005): 186-194.
Woodberry, T., et al. "Immunogenicity of a human immunodeficiency virus (HIV) polytope vaccine containing multiple HLA A2 HIV CD8+ cytotoxic T-cell epitopes." Journal of virology 73.7 (1999): 5320-5325.
Written Opinion of the International Searching Authority for PCT/AU2017/050772, dated Sep. 21, 2017.
Wu, Naxin, and Mohammad M. Ataai. "Production of viral vectors for gene therapy applications." Current opinion in biotechnology 11.2 (2000): 205-208.
Yaglom, Julia A., et al. "The molecular chaperone Ydj1 is required for the p34CDC28-dependent phosphorylation of the cyclin Cln3 that signals its degradation." Molecular and Cellular Biology 16.7 (1996): 3679-3684.
Yaglom, Julia, et al. "p34Cdc28-mediated control of Cln3 cyclin degradation." Molecular and Cellular Biology 15.2 (1995): 731-741.
Yoshitake, Shinji, et al. "Conjugation of glucose oxidase from Aspergillus niger and rabbit antibodies using N-hydroxysuccinimide ester of N-(4-carboxycyclohexylmethyl)-maleimide." European journal of biochemistry 101.2 (1979): 395-399.
Young, James W., and Ralph M. Steinman. "Dendritic cells stimulate primary human cytolytic lymphocyte responses in the absence of CD4+ helper T cells." The Journal of experimental medicine 171.4 (1990): 1315-1332.
Zhou, Fan, and Leaf Huang. "Liposome-mediated cytoplasmic delivery of proteins: an effective means of accessing the MHC class I-restricted antigen presentation pathway." Immunomethods 4.3 (1994): 229-235.
Zhou, Shang Zhen, et al. "Adeno-associated virus 2-mediated high efficiency gene transfer into immature and mature subsets of hematopoietic progenitor cells in human umbilical cord blood." The Journal of experimental medicine 179.6 (1994): 1867-1875.
Zhu, Ning, et al. "Systemic gene expression after intravenous DNA delivery into adult mice." Science 261.5118 (1993) 209-211.
Zwickl, Peter, Wolfgang Baumeister, and Alasdair Steven. "Disassembly lines: the proteasome and related ATPase-assisted proteases." Current opinion in structural biology 10.2 (2000): 242-250.
Lee, James, et al. "IL-17E, a novel proinflammatory ligand for the IL-17 receptor homolog IL-17Rh1." Journal of Biological Chemistry 276.2 (2001): 1660-1664.
Levine, Myron M. "Immunization against bacterial diseases of the intestine." Journal of pediatric gastroenterology and nutrition 31.4 (2000): 336-355.
Li X, Coffino P. Distinct domains of antizyme required for binding and proteolysis of ornithine decarboxylase. Mol Cell Biol. Jan. 1994;14(1):87-92.
Lim, Ai Ing, et al. "IL-12 drives functional plasticity of human group 2 innate lymphoid cells." Journal of Experimental Medicine 213.4 (2016): 569-583.
Loeffler, David A., et al. "Analysis of distribution of tumor-and preneoplasia-infiltrating lymphocytes using simultaneous hoechst 33342 labeling and immunophenotyping." Cytometry: The Journal of the International Society for Analytical Cytology 13.2 (1992): 169-174.
Lois, Carlos, et al. "Germline transmission and tissue-specific expression of transgenes delivered by lentiviral vectors." Science 295.5556 (2002): 868-872.
Luft, T., et al. "A serum-free culture model for studying the differentiation of human dendritic cells from adult CD34+ progenitor cells." Experimental hematology 26.6 (1998): 489-500.
Luft, Thomas, et al. "Type I IFNs enhance the terminal differentiation of dendritic cells." The Journal of Immunology 161.4 (1998): 1947-1953.
Lyme disease GenBank Accession No. U59487 1997.
Maezawa, Yuko, et al. "Involvement of TNF receptor-associated factor 6 in IL-25 receptor signaling." The Journal of Immunology 176.2 (2006): 1013-1018.
MAGE-1 GenBank Accession No. X541 56 and AA494311 2011.
Malaria GenBank Accession No. X53832 1991.
McGee, J. P., et al. "The encapsulation of a model protein in poly (D, L lactide-co-glycolide) microparticles of various sizes: an evaluation of process reproducibility." Journal of microencapsulation 14.2 (1997): 197-210.
McHugh, Rebecca S., et al. "Detection of a soluble form of B7-1 (CD80) in synovial fluid from patients with arthritis using monoclonal antibodies against distinct epitopes of human B7-1." Clinical immunology and immunopathology 87.1 (1998): 50-59.
Melanotransferrin GenBank Accession No. M12154 2009.
Mengaud, J., et al. "Expression in *Escherichia coli* and sequence analysis of the listeriolysin O determinant of Listeria monocytogenes." Infection and Immunity 56.4 (1988): 766-772.
Menne, Kerstin ML, Henning Hermjakob, and Rolf Apweiler. "A comparison of signal sequence prediction methods using a test set of signal peptides." Bioinformatics 16.8 (2000): 741-742.
Mestecky, Jiri. "The common mucosal immune system and current strategies for induction of immune responses in external secretions." Journal of clinical immunology 7.4 (1987): 265-276.
Michael, Sharon I., et al. "Binding-incompetent adenovirus facilitates molecular conjugate-mediated gene transfer by the receptor-mediated endocytosis pathway." Journal of Biological Chemistry 268.10 (1993): 6866-6869.
Miller AD, Rosman GJ. Improved retroviral vectors for gene transfer and expression. Biotechniques. Oct. 1989;7 (9):980-2, 984-6, 989-90.
Miller AD. Retrovirus packaging cells. Hum Gene Ther. 1990 Spring;1(1):5-14.
Miller, A. Dusty. "Human gene therapy comes of age." Nature 357.6378 (1992): 455-460.
Mittereder, Nanette, et al. "Evaluation of the efficacy and safety of in vitro, adenovirus-mediated transfer of the human cystic fibrosis transmembrane conductance regulator cDNA." Human gene therapy 5.6 (1994): 717-729.
Moore, Mark W., Francis R. Carbone, and Michael J. Bevan. "Introduction of soluble protein into the class I pathway of antigen processing and presentation." Cell 54.6 (1988): 777-785.
Morrison, Sherie L., et al. "Chimeric human antibody molecules: mouse antigen-binding domains with human constant region domains." Proceedings of the National Academy of Sciences 81.21 (1984): 6851-6855.
Mulligan, Richard C. "The basic science of gene therapy." Science 260.5110 (1993): 926-932.
Muzyczka, N. "Use of adeno-associated virus as a general transduction vector for mammalian cells." Viral expression vectors (1992): 97-129.
Neutra, Marian R., and Pamela A. Kozlowski. "Mucosal vaccines: the promise and the challenge." Nature reviews Immunology 6.2 (2006): 148-158.
Nothwehr, Steven F., and Jeffrey I. Gordon. "Targeting of proteins into the eukaryotic secretory pathway: signal peptide structure/function relationships." Bioessays 12.10 (1990): 479-484.
O'doherty, U., et al. "Human blood contains two subsets of dendritic cells, one immunologically mature and the other immature." Immunology 82.3 (1994): 487.
O'Hagan DT, McGee JP, Holmgren J, Mowat AM, Donachie AM, Mills KH, Gaisford W, Rahman D, Challacombe SJ. Biodegradable microparticles for oral immunization. Vaccine. 1993;11(2):149-54.
Onchocerciasis, GenBank Accession No. M27807 1993.

(56) References Cited

OTHER PUBLICATIONS

Ordiz, Isabel, et al. "Glucose-induced inactivation of isocitrate lyase in *Saccharomyces cerevisiae* is mediated by the cAMP-dependent protein kinase catalytic subunits Tpk 1 and Tpk2." FEBS letters 385.1-2 (1996): 43-46.
Orlandi, Rosaria, et al. "Cloning immunoglobulin variable domains for expression by the polymerase chain reaction." Proceedings of the National Academy of Sciences 86.10 (1989): 3833-3837.
Palmer, Michael, et al. "Streptolysin O: a proposed model of allosteric interaction between a pore-forming protein and ts target lipid bilayer" Biochemistry 37.8 (1998): 2378-2383.
Pan G, French D, Mao W, Maruoka M, Risser P, Lee J, Foster J, Aggarwal S, Nicholes K, Guillet S, Schow P, Gurney AL. Forced expression of murine IL-17E induces growth retardation, jaundice, a Th2-biased response, and multiorgan nflammation in mice. J Immunol. Dec. 1, 2001;167(11):6559-67.
Piemonti, Lorenzo, et al. "Glucocorticoids affect human dendritic cell differentiation and maturation." The Journal of Immunology 162.11 (1999): 6473-6481.
Portnoy, D. A., et al. "Capacity of listeriolysin O, streptolysin O, and perfringolysin O to mediate growth of Bacillus subtilis within mammalian cells." Infection and immunity 60.7 (1992): 2710-2717.
Poznansky, Mark J., et al. "Insulin: carrier potential for enzyme and drug therapy." Science 223.4642 (1984): 1304-1306.
Provinciali M, Di Stefano G, Fabris N. Optimization of cytotoxic assay by target cell retention of the fluorescent dye carboxyfluorescein diacetate (CFDA) and comparison with conventional 51CR release assay. J Immunol Methods. Oct. 19, 1992;155(1):19-24.
Ranasinghe, C., et al. "Unique IL-13Ra2-based HIV-1 vaccine strategy to enhance mucosal immunity, CD8+ T-cell avidity and protective immunity." Mucosal immunology 6.6 (2013): 1068-1080.
Ravichandran, J., et al., Cytokine Res, 2015, 35(3): 176-85 Ravichandran J, Jackson RJ, Trivedi S, Ranasinghe C. IL-17A expression in HIV-specific CD8 T cells is regulated by IL-4/IL-13 following HIV-1 prime-boost immunization. J Interferon Cytokine Res. Mar. 2015;35(3):176-85.
Reddy, Anita, et al. "A monocyte conditioned medium is more effective than defined cytokines in mediating the terminal maturation of human dendritic cells." Blood, The Journal of the American Society of Hematology 90.9 (1997): 3640-3646.
Rich DP, Couture LA, Cardoza LM, Guiggio VM, Armentano D, Espino PC, Hehir K, Welsh MJ, Smith AE, Gregory RJ. Development and analysis of recombinant adenoviruses for gene therapy of cystic fibrosis. Hum Gene Ther. Aug. 1993;4(4):461-76.
Rickel EA, Siegel LA, Yoon BR, Rottman JB, Kugler DG, Swart DA, Anders PM, Tocker JE, Comeau MR, Budelsky AL. Identification of functional roles for both IL-17RB and IL-17RA in mediating IL-25-induced activities. J Immunol. Sep. 15, 2008;181(6):4299-310.
Rivoltini, Licia, et al. "Phenotypic and functional analysis of lymphocytes infiltrating paediatric tumours, with a characterization of the tumour phenotype." Cancer Immunology, Immunotherapy 34.4 (1992): 241-251.
Rogers, Scott W., and M. Rechsteiner. "Degradation of structurally characterized proteins injected into HeLa cells. Basic measurements." Journal of Biological Chemistry 263.36 (1988): 19833-19842.
Rogers, Scott, Rodney Wells, and Martin Rechsteiner. "Amino acid sequences common to rapidly degraded proteins: the PEST hypothesis." Science 234.4774 (1986): 364-368.
Romani, Nikolaus, et al. "Generation of mature dendritic cells from human blood an improved method with special regard to clinical applicability." Journal of immunological methods 196.2 (1996): 137-151.

Rose, John K., Lm Buonocore, and M. A. Whitt. "A new cationic liposome reagent mediating nearly quantitative transfection of animal cells." BioTechniques 10.4 (1991): 520-525.
Ahonen, Cory L., et al. "Dendritic cell maturation and subsequent enhanced T-cell stimulation induced with the novel synthetic immune response modifier R-848." Cellular immunology 197.1 (1999): 62-72.
Aichele, P., et al. "Antiviral cytotoxic T cell response induced by in vivo priming with a free synthetic peptide." The Journal of experimental medicine 171.5 (1990): 1815-1820.
Albert, Matthew L., Birthe Sauter, and Nina Bhardwaj. "Dendritic cells acquire antigen from apoptotic cells and induce class I-restricted CTLs." Nature 392.6671 (1998): 86-89.
Albert, Matthew L., et al. "Tumor-specific killer cells in paraneoplastic cerebellar degeneration." Nature medicine 4.11 (1998): 1321-1324.
Alexander-Miller, Martha A. "High-avidity cd8+ t cells." Immunologic research 31.1 (2005): 13-24.
Alexander-Miller, Martha A., et al. "Role of antigen, CD8, and cytotoxic T lymphocyte (CTL) avidity in high dose antigen induction of apoptosis of effector CTL." The Journal of experimental medicine 184.2 (1996): 485-492.
Mien, Todd M., et al. "Induction of AIDS virus-specific CTL activity in fresh, unstimulated peripheral blood lymphocytes from rhesus macaques vaccinated with a DNA prime/modified vaccinia virus Ankara boost regimen." The Journal of Immunology 164.9 (2000): 4968-4978.
Allies, L. E. and Naldini, L, Lentiviral Vectors, Springer-Verlag, Bedin, Heidelberg, New York, 2002, 31-52.
Apostolopoulos V, Yu M, McKenzie IF, Wilson IA. Structural implications for the design of molecular vaccines. Curr Opin Mol Ther. Feb. 2000;2(1):29-36.
Mis, David, and Hergen Spits. "The biology of innate lymphoid cells." Nature 517.7534 (2015): 293-301.
Athanasopoulos T, Fabb S, Dickson G. Gene therapy vectors based on adeno-associated virus: characteristics and applications to acquired and inherited diseases (review). Int J Mol Med. Oct. 2000;6(4):363-75. doi: 10.3892/jmm.6.4.363.
Atherton and Shephard, 1994, Synthetic Vaccines, Chapter 9—"Peptide Synthesis", ed. By Nicholson and published by Blackwell Scientific Publications.
Ausubel, F.M., Brent, R., Kingston, R.E., Moore, D.D., Seidman, J.G., Smith, J.A. and Struhl, K. (2003) Current Protocols in Molecular Biology. Wiley, New York.
Bachmann, Martin F., et al. "Dendritic cells process exogenous viral proteins and virus-like particles for class I presentation to CD8+ cytotoxic T lymphocytes." European journal of immunology 26.11 (1996): 2595-2600.
Barr, Eliav, and Jeffrey M. Leiden. "Systemic delivery of recombinant proteins by genetically modified myoblasts." Science 254. 5037 (1991): 1507-1509.
Barr, Eliav, et al. "Efficient catheter-mediated gene transfer into the heart using replication-defective adenovirus." Gene therapy 1.1 (1994): 51-58.
Berkner, Kathleen L. "Development of adenovirus vectors for the expression of heterologous genes." Biotechniques 6.7 (1988): 616-629.
Bemink, Jochem H., et al. "Interleukin-12 and-23 control plasticity of CD127+ group 1 and group 3 innate lymphoid cells in the intestinal lamina propria." Immunity 43.1 (2015): 146-160.
Bertling, Wolf M., et al. "Use of liposomes, viral capsids, and nanoparticles as DNA carriers." Biotechnology and applied biochemistry 13.3 (1991): 390-405.
Bett AJ, Prevec L, Graham FL. Packaging capacity and stability of human adenovirus type 5 vectors. J Virol. Oct. 1993;67(10):5911-21.
Bohley, Peter, et al. "Post-translational arginylation and intracellular proteolysis." Biomedica biochimica acta 50.4-6 (1991): 343-346.
Bohley, Peter. "Surface hydrophobicity and intracellular degradation of proteins." Biological chemistry 377.7-8 (1996): 425-435.
Bordetella pertussis, GenBank Accession No. M35274 1993.
Boris-Lawrie KA, Temin HM. Recent advances in retrovirus vector technology. Curr Opin Genet Dev. Feb. 1993;3 (1): 102-9.

(56) References Cited

OTHER PUBLICATIONS

Burns, Jane C., et al. "Vesicular stomatitis virus G glycoprotein pseudotyped retroviral vectors: concentration to very high titer and efficient gene transfer into mammalian and nonmammalian cells." Proceedings of the National Academy of Sciences 90.17 (1993): 8033-8037.
Cai, Liping, et al. "Pathways by which interleukin 17 induces articular cartilage breakdown in vitro and in vivo." Cytokine 16.1 (2001): 10-21.
Calabretta, Bruno, et al. "Prospects for gene-directed therapy with antisense oligodeoxynucleotides." Cancer treatment reviews 19.2 (1993): 169-179.
Camilli, Andrew, Howard Goldfine, and Daniel A. Portnoy. "Listeria monocytogenes mutants lacking phosphatidylinositol-specific phospholipase C are avirulent " Journal of Experimental Medicine 173.3 (1991): 751-754.
Carlsson, Jan, H. A. K. A. N. Drevin, and R. O. L. F. Axén. "Protein thiolation and reversible protein-protein conjugation. N-Succinimidyl 3-(2-pyridyldithio) propionate, a new heterobifunctional reagent." Biochemical Journal 173.3 (1978): 723-737.
Carmichael, A., et al. "Quantitative analysis of the human immunodeficiency virus type 1 (HIV-1)-specific cytotoxic T ymphocyte (CTL) response at different stages of HIV-1 infection: differential CTL responses to HIV-1 and Epstein-Barr virus in late disease." The Journal of experimental medicine 177.2 (1993): 249-256.
Carter, Barrie J. "Adeno-associated virus vectors." Current Opinion in Biotechnology 3.5 (1992): 533-539.
Darter, Paul, et al. "Humanization of an anti-p185HER2 antibody for human cancer therapy." Proceedings of the National Academy of Sciences 89.10 (1992): 4285-4289.
Caux C, Vanbervliet B, Massacrier C, Durand I, Banchereau J. Interleukin-3 cooperates with tumor necrosis factor alpha for the development of human dendritic/Langerhans cells from cord blood CD34+ hematopoietic progenitor cells. Blood. Mar. 15, 1996;87(6):2376-85. PMID: 8630401.
Caux, Christophe, et al. "CD34+ hematopoietic progenitors from human cord blood differentiate along two independent dendritic cell pathways in response to GM-CSF+ TNF alpha." The Journal of experimental medicine 184.2 (1996): 695-706.
Della M, Engering A, Pinet V, Pieters J, Lanzavecchia A. Inflammatory stimuli induce accumulation of MHC class II complexes on dendritic cells. Nature. Aug. 21, 1997;388(6644):782-7.
Cella M, Scheidegger D, Palmer-Lehmann K, Lane P, Lanzavecchia A, Alber G. Ligation of CD40 on dendritic cells triggers production of high levels of interleukin-12 and enhances T cell stimulatory capacity: T-T help via APC activation. J Exp Med. Aug. 1, 1996;184(2):747-52.
Cella, Marina, et al. "Maturation, activation, and protection of dendritic cells induced by double-stranded RNA." The Journal of experimental medicine 189.5 (1999): 821-829.
Chang, Alfred E., et al. "Clinical observations on adoptive immunotherapy with vaccine-primed T-lymphocytes secondarily sensitized to tumor in vitro." Cancer research 53.5 (1993): 1043-1050.
Chapman, Andrew P., et al. "Therapeutic antibody fragments with prolonged in vivo half-lives." Nature biotechnology 17.8 (1999): 780-783.
Chen, William S., et al. "Requirement for intrinsic protein tyrosine kinase in the immediate and late actions of the EGF receptor." Nature 328.6133 (1987): 820-823.
Chimera Protein R3_S GenBank Accession No. E07883 2005.
Clostridium tetani, GenBank Accession No. M64353 1995.
Cohen, John. "Naked DNA pointsway to vaccines." Science 259. 5102 (1993): 1691-1693.
Coupar, Barbara EH, et al. "Fowlpox virus vaccines for HIV and SHIV clinical and pre-clinical trials." Vaccine 24.9 (2006): 1378-1388.
Cox, John C., and Alan R. Coulter. "Adjuvants—a classification and review of their modes of action." Vaccine 15.3 (1997): 248-256.
Creemers JW, Jackson RS, Hutton JC. Molecular and cellular regulation of prohormone processing. Semin Cell Dev Biol. Feb. 1998;9(1):3-10.
Dalbey, Ross E., et al. "The chemistry and enzymology of the type I signal peptidases." Protein Science 6.6 (1997): 1129-1138.
Dengue Virus type 2 GenBank Accession No. M24444 1993.
Dhawan, Jyotsna, et al. "Systemic delivery of human growth hormone by injection of genetically engineered myoblasts." Science 254.5037 (1991): 1509-1512.
Faas, Susan J., et al. "Primary structure and functional characterization of a soluble, alternatively spliced form of B7-1." The Journal of Immunology 164.12 (2000): 6340-6348.
Falkner FG, Moss B. Transient dominant selection of recombinant vaccinia viruses. J Virol. Jun. 1990;64(6):3108-11.
Fearnley, D. B., et al. "Isolation of human blood dendritic cells using the CMRF-44 monoclonal antibody: implications for studies on antigen-presenting cell function and immunotherapy." Blood, The Journal of the American Society of Hematology 89.10 (1997): 3708-3716.
Feigner, P.L., Advanced Drug Delivery Reviews (1990) 5:163-187.
Ferber, Sarah, and Aaron Ciechanover. "Role of arginine-tRNA in protein degradation by the ubiquitin pathway." Nature 326.6115 (1987): 808-811.
Fields, B.N. Fundamental Virology, Second Edition, 1996, Raven Press, New York.
Filariasis, GenBank Accession No. J03266 1993.
Freudenthal, Peter S., and Ralph M. Steinman. "The distinct surface of human blood dendritic cells, as observed after an improved isolation method." Proceedings of the National Academy of Sciences 87.19 (1990): 7698-7702.
Gao, Xiao-Ming, et al. "Priming of influenza virus-specific cytotoxic T lymphocytes vivo by short synthetic peptides." The Journal of Immunology 147.10 (1991): 3268-3273.
Ghoda L, Sidney D, Macrae M, Coffino P. Structural elements of ornithine decarboxylase required for intracellular degradation and polyamine-dependent regulation. Mol Cell Biol. May 1992;12(5):2178-85.
Giardiasis, GenBank Accession No. M33641 199.
Glotzer, Michael, Andrew W. Murray, and Marc W. Kirschner. "Cyclin is degraded by the ubiquitin pathway." Nature 349.6305 (1991): 132-138.
Haj-Ahmad, Yousef, and Frank L. Graham. "Development of a helper-independent human adenovirus vector and its use in the transfer of the herpes simplex virus thymidine kinase gene." Journal of virology 57.1 (1986): 267-274.
Heine, H-G., and D. B. Boyle. "Infectious bursal disease virus structural protein VP 2 expressed by a fowlpox virus recombinant confers protection against disease in chickens." Archives of virology 131.3-4 (1993): 277-292.
Hepatitis C Virus Antigen GenBank Accession No. E06890 2005.
Hepworth, Matthew R., Marcus Maurer, and Susanne Hartmann. "Regulation of type 2 immunity to helminths by mast cells." Gut microbes 3.5 (2012): 476-481.
Hill, Adrian VS, et al. "Molecular analysis of the association of HLA-B53 and resistance to severe malaria." Nature 360.6403 (1992): 434-439.
Human Hepatitis B Virus GenBank Accession No. E02707 2005.
IGHM GenBank Accession No. M34678 2016.
Iizuka, Tomomichi, et al. "Intracellular generation of amyloid β-protein from amyloid β-protein precursor fragment by direct cleavage with β-and ?-secretase." Biochemical and biophysical research communications 218.1 (1996): 238-242.
IL-25 gene (identified by GenBank accession No. AF305200; UniProt accession No. Q9H293) 2001.
IL17RA—UniProt accession No. Q96F46; GenBank accession No. BC01 1624 2006.
IL17RB-UniProtKB accession No. Q9NRM6 2021.
International Search Report for PCT/AU2017/050//2, dated Sep. 21, 2017.
Invitrogen technical manual "Viral Power Lentiviral Expression System Version B 050102 25-0501 ." Jul. 7, 2010.

(56) References Cited

OTHER PUBLICATIONS

Izard, Jennifer W., and Debra A. Kendall. "Signal peptides: exquisitely designed transport promoters." Molecular microbiology 13.5 (1994): 765-773.

Jackson, R.J., Boyle, D.B., Ranasinghe, C, Methods Mol Biol, 2014, 1143:61-90.

Jackson, Ronald J., Diana F. Hall, and Peter J. Kerr. "Construction of recombinant myxoma viruses expressing foreign genes from different intergenic sites without associated attenuation." Journal of General Virology 77.7 (1996): 1569-1575.

Jeannin, Pascale, et al. "Soluble CD86 is a costimulatory molecule for human T lymphocytes." Immunity 13.3 (2000): 303-312.

Jeffery, Hayley, Stanley S. Davis, and Derek T. O'Hagan. "The preparation and characterization of poly (lactide-co-glycolide) microparticles. II. The entrapment of a model protein using a (water-in-oil)-in-water emulsion solvent evaporation technique." Pharmaceutical research 10.3 (1993): 362-368.

Johnson, R. P., et al. "Identification of overlapping HLA class I-restricted cytotoxic T cell epitopes in a conserved region of the human immunodeficiency virus type 1 envelope glycoprotein: definition of minimum epitopes and analysis of the effects of sequence variation." The Journal of experimental medicine 175.4 (1992): 961-971.

Jondal, Mikael, Reinhold Schirmbeck, and Jörg Reimann. "MHC class I-restricted CTL responses to exogenous antigens." Immunity 5.4 (1996): 295-302.

Jones, Peter T., et al. "Replacing the complementarity-determining regions in a human antibody with those from a mouse." Nature 321.6069 (1986): 522-525.

Jue, Rodney, et al. "Addition of sulfhydryl groups of *Escherichia coli* ribosomes by protein modification with 2-minothiolane (methyl 4 mercaptobutyrimidate)." Biochemistry 17.25 (1978): 5399 5406.

Kaposi's Sarcoma-Associated Herpes-like Virus GenBank Accession No. U18552 1995.

Kay, Mark A., Joseph C. Glorioso, and Luigi Naldini. "Viral vectors for gene therapy: the art of turning infectious agents into vehicles of therapeutics." Nature medicine 7.1 (2001): 33-40.

Keiler, Kenneth C., Patrick RH Waller, and Robert T. Sauer. "Role of a peptide tagging system in degradation of proteins synthesized from damaged messenger RNA." Science 271.5251 (1996): 990-993.

Kelley ("Engineering Therapeutic Antibodies," in Protein Engineering: Principles and Practice Cleland et al. (eds.), 1996, pp. 399-434 (John Wiley & Sons, Inc. 1996).

Kennedy, Jeffrey S., and Richard N. Greenberg. "IMVAMUNE®: modified vaccinia Ankara strain as an attenuated smallpox vaccine." Expert review of vaccines 8.1 (2009): 13-24.

Kim HY, Chang YJ, Subramanian S, Lee HH, Albacker LA, Matangkasombut P, Savage PB, McKenzie AN, Smith DE, Rottman JB, DeKruyff RH, Umetsu DT. Innate lymphoid cells responding to IL-33 mediate airway hyperreactivity Independently of adaptive immunity. J Allergy Clin Immunol. Jan. 2012;129(1):216-27.e1-6.

King, Randall W., et al. "How proteolysis drives the cell cycle." Science 274.5293 (1996): 1652-1659.

King, Randall W., M. Glotzer, and M. W. Kirschner. "Mutagenic analysis of the destruction signal of mitotic cyclins and structural characterization of ubiquitinated intermediates." Molecular biology of the cell 7.9 (1996): 1343-1357.

Klotz, Irving M., and Richard E. Heiney. "Introduction of sulfhydryl groups into proteins using acetylmercaptosuccinic anhydride." Archives of biochemistry and biophysics 96.3 (1962): 605-612.

Kotin, Robert M. "Prospects for the use of adeno-associated virus as a vector for human gene therapy." Human gene therapy 5.7 (1994): 793-801.

Koup, Richard A., et al. "Limiting dilution analysis of cytotoxic T lymphocytes to human immunodeficiency virus gag antigens in infected persons: in vitro quantitation of effector cell populations with p17 and p24 specificities." The Journal of experimental medicine 174.6 (1991): 1593-1600.

Kunkel, Eric J., and Eugene C. Butcher. "Plasma-cell homing." Nature Reviews Immunology 3.10 (2003): 822-829.

Kuzu, Hiroshi, et al. "In vivo priming effect during various stages of ontogeny of an influenza A virus nucleoprotein peptide." European journal of immunology 23.6 (1993): 1397-1400.

La Gruta, Nicole L., Stephen J. Turner, and Peter C. Doherty. "Hierarchies in cytokine expression profiles for acute anti Yesolving influenza virus-specific CD8+ T cell responses: correlation of cytokine profile and TCR avidity." The Journal of Immunology 172.9 (2004): 5553-5560.

Ladunga, Istvan. "Large-scale predictions of secretory proteins from mammalian genomic and EST sequences." Current Opinion in Biotechnology 11.1 (2000): 13-18.

Lamm ME. Interaction of antigens and antibodies at mucosal surfaces. Annu Rev Microbiol. 1997;51:311-40.

Lebkowski JS, McNally MM, Okarma TB, Lerch LB. Adeno-associated virus: a vector system for efficient introduction and integration of DNA into a variety of mammalian cell types. Mol Cell Biol. Oct. 1988;8(10):3988-96.

\* cited by examiner

IMMUNOSTIMULATORY COMPOSITIONS AND USES THEREFOR

This application claims priority to Australian Provisional Application No. 2016902939 entitled "Immunostimulatory Compositions and Uses Therefor" filed 26 Jul. 2016, the contents of which are incorporated herein by reference in their entirety.

SEQUENCE LISTING

The instant application contains a Sequence Listing which has been filed electronically in ASCII format and is hereby incorporated by reference in its entirety. Said ASCII copy, created on Apr. 2, 2019, is named 2932719-074-US1_SL.txt and is 54,409 bytes in size.

FIELD OF THE INVENTION

This invention relates generally to compositions and methods for stimulating immune responses. More particularly, the present invention relates to the co-expression, co-location or co-presentation on host cells (e.g. antigen-presenting cells, leukocytes, etc.) of an inhibitor of IL-25 function and an immune stimulator that stimulates an immune response to a target antigen in compositions and methods for stimulating protective or therapeutic immune responses to the target antigen. The compositions and methods of the present invention are particularly useful in the prevention and treatment of infections and cancers.

BACKGROUND OF THE INVENTION

Most infectious agents penetrate the defense barriers of a host at the mucosal membranes or surfaces. Perhaps unsurprisingly, it is becoming increasingly clear that local mucosal immune responses are particularly important for protection against disease (see, Levine, M. M., *J Pediatr Gastroenterol Nutr*, 2000, 31: 336-355). In this regard, mucosal immune responses are most efficiently induced by the administration of vaccines onto mucosal surfaces, whereas injected (i.e., systemic) immunizations are generally poor inducers of mucosal immunity and are therefore considered to be less effective against infection at a mucosal surface (see, Lamm, M. E., *Annu Rev Microbiol*, 1997, 51: 311-340). Nevertheless, clinical vaccine research continues to remain primarily based on the injection of antigens, administered either intramuscularly or subcutaneously (see, Neutra, M. R. and Kozlowski, P. A., *Nat Rev Immunol*, 2006, 6: 148-158).

For many pathogens, optimal protection is likely to require in parallel both mucosal and systemic immune responses. The most effective mucosal vaccine strategies might be prime-boost combinations that involve both mucosal and systemic delivery. It has been reported that mucosal immunization can prime the immune system for both systemic and mucosal responses, presumably by inducing the expression of both mucosal and systemic homing receptors by responding lymphocytes (see, Kunkel, E. J., and Butcher, E. C., *Nature Rev Immunol*, 2003, 3: 822-829). By contrast, parenteral priming is unlikely to prime the immune system for subsequent mucosal vaccination (Mestecky, J., *J Clin Immunol*, 1987, 7: 265-276).

It has previously been established that mucosal immunizations can generate high-avidity HIV-specific $CD8^+$ T cells, as compared to systemic immunization. The present inventors have demonstrated that the cytokine interleukin (IL)-13 is detrimental to the functional avidity of these T cells, and that T cell avidity is significantly improved by transient inhibition of IL-13 function in the local milieu of the immune response (see, Ranasinghe et al., *Mucosal Immunity*, 2013, 6(6): 1068-1080).

Although many of the current HIV vaccine trials show enhanced immunity in animals, they have failed to establish true correlates of protection. These findings increasingly suggest that not only the magnitude but also the "quality" or "avidity" of the T cell response generated against vaccine antigens may be important in protection against pathogenic organisms such as HIV-1. The quality of the T cell response is reflected in the functional avidity of T cells towards the MHC-peptide complex on target cells. High avidity cytotoxic T lymphocytes (CTL) recognise low concentrations of antigen, whilst low avidity CTL are functionally ineffective at these antigen concentrations (Alexander-Miller et al., 1996, *J. Exp. Med.* 184: 485-492; La Gruta et al., 2004, *J. Immunol.* 172: 5553-5560). It is now well established that high avidity CTL also have greater capacity to clear an infection compared to low avidity T cells (Alexander-Miller et al., 2005, *Immunol. Res.* 31: 13-24).

Moreover, local antiviral immune responses in the genital and rectal tissues where HIV is usually first encountered are vital. Local immune responses in the gastro-intestinal tract are also important given that it is a major site of HIV replication. The presence of high-avidity antiviral T cells at sites of initial HIV exposure, i.e., the mucosa, offers great potential for reducing mucosal $CD4^+$ T cell depletion and local control of HIV infection. Given their demonstrated capacity to recognise target cells expressing very low levels of viral antigen (e.g., early after infection of a cell), and a more rapid initiation of target cell lysis even at low concentrations of target antigen, vaccine strategies that elicit high-avidity CTL are likely to offer substantial protection against infection.

The innate lymphoid cells (ILC) are a recently identified class of lymphocytes that do not express antigen receptors (in contrast to T or B cells), or surface markers characteristic of other immune cell types, i.e., Lineage negative ($Lin^-$), (see, Artis, D., and Spits, H., *Nature*, 2015, 517(7534): 293-301).

ILC are currently characterized into three sub-groups based upon their cell surface receptors, transcription factors and cytokine expression. Group 1 ILC ("ILC1") are $T-bet^+$, and express IFN-γ and TNF-α. Group 2 ILC ("ILC2") are $IL-25R^+$, $IL-33R^+$, $TSLPR^+$, and $GATA3^+$, and express cytokines IL-5, IL-13, IL-9 and IL-4. Group 3 ILC ("ILC3") are $RORγt^+$ and express cytokines IL-17A and IL-22. Notably, recent publications suggest that ILC type may be fluid depending upon the cytokine environment determining ILC differentiation. For example, ILC3 and ILC2 can reportedly develop into ILC1 when activated by either IL-12 or IL-18 (see, Bernink, J. H., et al., *Immunity*, 2015, 43(1): 146-60; and Lim, A. I., et al., *J Exp Med*, 2016).

The majority of ILC studies concern inflammatory conditions such as allergy, asthma and atopic dermatitis (ILC2), psoriasis and inflammatory bowel disease (ILC1 and ILC3). ILC2 cells have been shown to be required for Th2 mediated immunity towards parasitic helminth infections (see, Artis and Spits, supra). The requirement of ILC1 in Th1 mediated immunity towards intracellular infections (e.g., viruses) and ILC3 in Th17 mediated immunity towards bacterial and fungal infections has been proposed. The specific molecular mechanisms by which these cell types might act is yet to be fully understood.

SUMMARY OF THE INVENTION

The present inventors have surprisingly discovered that the avidity of antigen-specific immune responses to a target antigen can be increased by inhibiting IL-25 function. This co-administration (i.e., antigen and inhibitor of IL-25 function) has particular advantages in the prevention or treatment of any diseases and/or conditions that are associated with the presence or aberrant expression of a target antigen in a subject.

Thus, in one aspect, the present invention provides immunostimulatory compositions for stimulating an immune response to a target antigen in a subject. In certain embodiments, the immune response is a T-cell mediated response. In another aspect, the present invention provides compositions for preventing or treating a disease or condition associated with the presence or aberrant expression of a target antigen in a subject.

The immunostimulatory compositions of the present invention generally comprise a first agent comprising an immune stimulator or a polynucleotide sequence from which a nucleotide sequence encoding an immune stimulator is expressible, wherein the immune stimulator stimulates or otherwise enhances an immune response to a target antigen in a subject, together with a second agent comprising an inhibitor of IL-25 function or a polynucleotide from which a nucleotide sequence encoding an inhibitor of IL-25 function is expressible.

In some embodiments, the immunostimulatory composition comprises a nucleic acid composition comprising: a first agent comprising a coding sequence for an immune stimulator operably linked to a regulatory polynucleotide, wherein the immune stimulator stimulates or otherwise enhances an immune response to a target antigen in a subject and a second agent comprising a coding sequence for an inhibitor of IL-25 operably linked to a regulatory polynucleotide.

In some embodiments, the immune stimulator is selected from an antigen that corresponds to at least a portion of the target antigen. The target antigen is typically associated with a disease or condition of interest, including but not limited to pathogenic infections and cancers, such as but not limited to human immunodeficiency virus (HIV) infection, tuberculosis (TB), non-pharyngeal carcinoma, and hepatitis C, as well as agricultural diseases such as bovine tuberculosis and Johne's disease. The antigen that corresponds to at least a portion of the target antigen may be provided to the subject in soluble form (e.g., a peptide or polypeptide), or in soluble form when expressed.

In some embodiments, the inhibitor of IL-25 function is selected from a variant form of IL-25, soluble or defective IL-25 receptors or fragments thereof, or antigen-binding molecules that are immuno-interactive with IL-25 or an IL-25 receptor.

In some embodiments, the subject is naïve to the target antigen or has previously raised an immune response to the target antigen. Suitably, in embodiments in which the subject has previously raised an immune response to the target antigen and the immune stimulator comprises an antigen that corresponds to the target antigen, the amino acid sequence of the corresponding antigen is the same as the amino acid sequence of at least a portion of the target antigen. In illustrative examples of this type, the corresponding antigen is a naturally-occurring antigen to which the subject has previously raised an immune response.

Exemplary immunostimulatory compositions of the present invention include vaccines or constructs, including but not limited to recombinant vaccines.

Notably, the immunostimulatory compositions of the present invention have any one or more activities selected from the group consisting of: stimulating or inducing the development of a Th17 response to the antigen; stimulating or inducing the development of a Th1 response to the antigen; suppressing the expression of any one or more of IL-13, IL-4 IL-9, and IL-5 by ILC2 cells; stimulating the development of ILC1; and stimulating the development of ILC3;

In some embodiments, the immunostimulatory compositions further comprises one or more ancillary agents. For example, a suitable ancillary agent is a cytokine selected from the group consisting of IL-12, IL-3, IL-5, TNF-α, GMCSF, and IFN-γ.

In some embodiments, the immunostimulatory compositions further comprise a pharmaceutically acceptable carrier or diluent. In some embodiments, the compositions further comprise an adjuvant that enhances the effectiveness of the immune stimulation. Suitably, the adjuvant delivers the antigen to the class I major histocompatibility (MHC) pathway. For example, such adjuvants include, but are not limited to, saponin-containing compounds (e.g., ISCOMs) and cytolysins, which mediate delivery of antigens to the cytosol of a target cell. The cytolysin may be linked to, or otherwise associated with, the antigen. In some embodiments, the cytolysin mediates transfer of the antigens from the vacuole (e.g., phagosome or endosome) to the cytosol of an antigen-presenting cell and in illustrative examples of this type, the cytolysin is a listeriolysin.

In some embodiments, the antigen comprises, or is otherwise associated with, an intracellular degradation signal or degron. In illustrative examples of this type, the intracellular degradation signal comprises a destabilizing amino acid at the amino-terminus of the antigen. Suitably, the destabilizing amino acid is selected from isoleucine and glutamic acid, preferably from histidine tyrosine and glutamine, and even more preferably from aspartic acid, asparagine, phenylalanine, leucine, tryptophan and lysine. In a specific embodiment, the destabilizing amino acid is arginine. In other illustrative examples of this type, the antigen is fused or otherwise conjugated to a masking entity, which masks the amino terminus so that when unmasked the antigen will exhibit an enhanced rate of intracellular proteolytic degradation. Suitably, the masking entity is a masking protein sequence. The masking protein sequence is suitably cleavable by an endoprotease, which is typically an endogenous endoprotease of a mammalian cell. For example, an endoprotease cleavage site may be interposed between the masking protein sequence and the antigen. Suitable endoproteases include, but are not restricted to, serine endoproteases (e.g., subtilisins and furins), proteasomal endopeptidases, proteases relating to the MHC class I processing pathway and signal peptidases. In a preferred embodiment of this type, the masking protein sequence comprises a signal peptide sequence. Suitable signal peptides sequences are described, for example, by Nothwehr et al. (1990, *Bioessays* 12 (10): 479-484); Izard, et al. (1994, *Mol. Microbiol.* 13 (5): 765-773); Menne, et al. (2000, *Bioinformatics.* 16 (8): 741-742); and Ladunga (2000, *Curr. Opin. Biotechnol.* 11 (1): 13-18).

Alternatively, or in addition, the intracellular degradation signal comprises a ubiquitin acceptor, which allows for the attachment of ubiquitin by intracellular enzymes, which target the antigen for degradation via the ubiquitin-proteosome pathway. Suitably, the ubiquitin acceptor is a molecule which contains a residue appropriately positioned from the amino terminus of the antigen as to be able to be bound by ubiquitin molecules. Such residues may have an epsilon amino group such as lysine. In illustrative examples of this type, the ubiquitin acceptor comprises at least one, preferably at least two, more preferably at least four and still more preferably at least six lysine residues, which are suitably present in a sufficiently segmentally mobile region of the antigen.

In some embodiments, the intracellular degradation signal comprises a ubiquitin or biologically active fragment thereof. In non-limiting examples of this type, the ubiquitin or biologically active fragment thereof is fused, or otherwise conjugated, to the antigen. Suitably, the ubiquitin is of mammalian origin. By way of an illustrative example, a suitable ubiquitin could be of human or other primate origin.

Another aspect of the present invention provides methods for stimulating an immune response to a target antigen in a subject. In certain embodiments, the immune response is a T cell mediated response (e.g., a $CD8^+$ T cell response, and/or a $CD4^+$ T cell response). In some of the same and other embodiments, the immune response is a B cell mediated response. A further aspect of the present invention provides methods for treating or preventing a disease or condition associated with the presence or aberrant expression of a target antigen in a subject.

The methods of the present invention generally comprise administering to the subject an effective amount of a first agent comprising an immune stimulator or a polynucleotide sequence from which a nucleotide sequence encoding an immune stimulator is expressible, wherein the immune stimulator stimulates or otherwise enhances an immune response to a target antigen in a subject together with a second agent comprising an inhibitor of IL-25 function or a polynucleotide from which a nucleotide sequence encoding an inhibitor of IL-25 function is expressible, as broadly described above. The target antigen is typically associated with a disease or condition of interest, including but not limited to pathogenic infections and cancers, such as but not limited to HIV, TB, non-pharyngeal carcinoma, hepatitis C, as well as agricultural diseases such as bovine tuberculosis and Johne's disease.

In some embodiments, the subject is naïve to the target antigen or has previously raised an immune response to the target antigen. Suitably, in embodiments in which the subject has previously raised an immune response to the target antigen and the immune stimulator comprises an antigen that corresponds to the target antigen, the amino acid sequence of the corresponding antigen is the same as the amino acid sequence of at least a portion of the target antigen. In illustrative examples of this type, the corresponding antigen is a naturally-occurring antigen to which the subject has previously raised an immune response.

In some embodiments, the first agent and the second agent are administered intramuscularly. It is proposed that the inhibitor of IL-25 function may sequester the availability of free IL-25 to bind muscle cell IL-25R and thus provide a transient blockade of IL-25 signaling.

In yet another aspect, the invention contemplates the use of first agent comprising an immune stimulator or a polynucleotide sequence from which a nucleotide sequence encoding an immune stimulator is expressible, wherein the immune stimulator stimulates or otherwise enhances an immune response to a target antigen in a subject together with a second agent comprising an inhibitor of IL-25 function or a polynucleotide from which a nucleotide sequence encoding an inhibitor of IL-25 function is expressible as broadly defined above in the manufacture of a medicament for stimulating an immune response to the target antigen in a subject. In certain embodiments, the immune response is a T cell mediated response (e.g., a $CD8^+$ T cell response, and/or a $CD4^+$ T cell response). The target antigen is typically associated with a disease or condition of interest, including but not limited to pathogenic infections and cancers, such as, but not limited to HIV, TB, non-pharyngeal carcinoma, and hepatitis C. Agricultural diseases such as bovine tuberculosis and Johne's disease are also contemplated.

In still another aspect, the invention resides in the use of a first agent comprising an immune stimulator or a polynucleotide sequence from which a nucleotide sequence encoding an immune stimulator is expressible, wherein the immune stimulator stimulates or otherwise enhances an immune response to a target antigen in a subject together with a second agent comprising an inhibitor of IL-25 function or a polynucleotide from which a nucleotide sequence encoding an inhibitor of IL-25 function is expressible as broadly defined above in the manufacture of a medicament for preventing or treating a disease or condition associated with the presence or aberrant expression of the target antigen in a subject. The target antigen is typically associated with a disease or condition of interest, including but not limited to pathogenic infections and cancers, such as but not limited to HIV, TB, non-pharyngeal carcinoma and hepatitis C, as well as agricultural diseases such as bovine tuberculosis and Johne's disease.

In one aspect, the present invention provides a method of enhancing a Th17 immune response in a subject, wherein the Th17 immune response can be determined by detecting an increase in the expression of any one of the cytokines: IL-17A, IL-22, TNF-α, IL-17F, IL-21, IL-26, GM-CSF, and MIP-A.

In various aspects, the present invention is directed to a method of enhancing a Th1 immune response, wherein the Th1 immune response comprises an increase in the expression of any one of IFN-γ, IL-2 and TNF-β.

In yet some other aspects, the present invention provides methods for suppressing the expression of one or more cytokines selected from any one of IL-13, IL-4, IL-9, and IL-5 at the vaccination site of the subject.

Yet another aspect of the present invention provides an immunostimulatory antigen-presenting cell or antigen-presenting cell precursor that presents an antigen that corresponds to at least a portion of the target antigen, and wherein the antigen-presenting cell or antigen-presenting cell precursor expresses or otherwise produces an inhibitor of IL-25 function.

Yet a further aspect of the present invention provides a method for producing an immunostimulatory antigen-presenting cell, the method comprising contacting an antigen-presenting cell or antigen-presenting cell precursor with an antigen that corresponds to at least a portion of the target antigen or a composition of the invention for a time and under conditions sufficient for the antigen or a processed form thereof to be presented by the antigen-presenting cell or antigen-presenting cell precursor, and wherein the antigen-presenting cell or antigen-presenting cell precursor expresses or otherwise produces an inhibitor of IL-25 function.

Still another aspect of the present invention provides a method for enhancing mucosal immunity to a target antigen in a subject that is administered a first agent comprising an immune stimulator or a polynucleotide sequence from which a nucleotide sequence encoding an immune stimulator is expressible, wherein the immune stimulator stimulates or otherwise enhances an immune response to the target antigen, the method comprising systemically administering to the subject a second agent comprising an inhibitor of IL-25 function or a polynucleotide from which a nucleotide sequence encoding an inhibitor of IL-25 function is expressible, as broadly described above, to thereby enhance mucosal immunity to the target antigen. In certain embodiments, the first agent and the second agent are systemically administered concurrently to the subject.

In a related aspect, the present invention provides a use of an IL-25 inhibitory agent comprising an inhibitor of IL-25 function or a polynucleotide from which a nucleotide sequence encoding an inhibitor of IL-25 function is expressible, as broadly described above, for enhancing mucosal immunity to a target antigen by an immunostimulatory agent comprising an immune stimulator or a polynucleotide sequence from which a nucleotide sequence encoding an immune stimulator is expressible, wherein the immune stimulator stimulates or otherwise enhances an immune response to the target antigen, wherein the IL-25 inhibitory agent is formulated for systemic administration. In some embodiments, both the IL-25 inhibitory agent and the immunostimulatory agent are formulated for concurrent administration via a systemic route. In specific embodiments, the systemic route is intramuscular.

DETAILED DESCRIPTION OF THE INVENTION

1. Definitions

Figure 1:
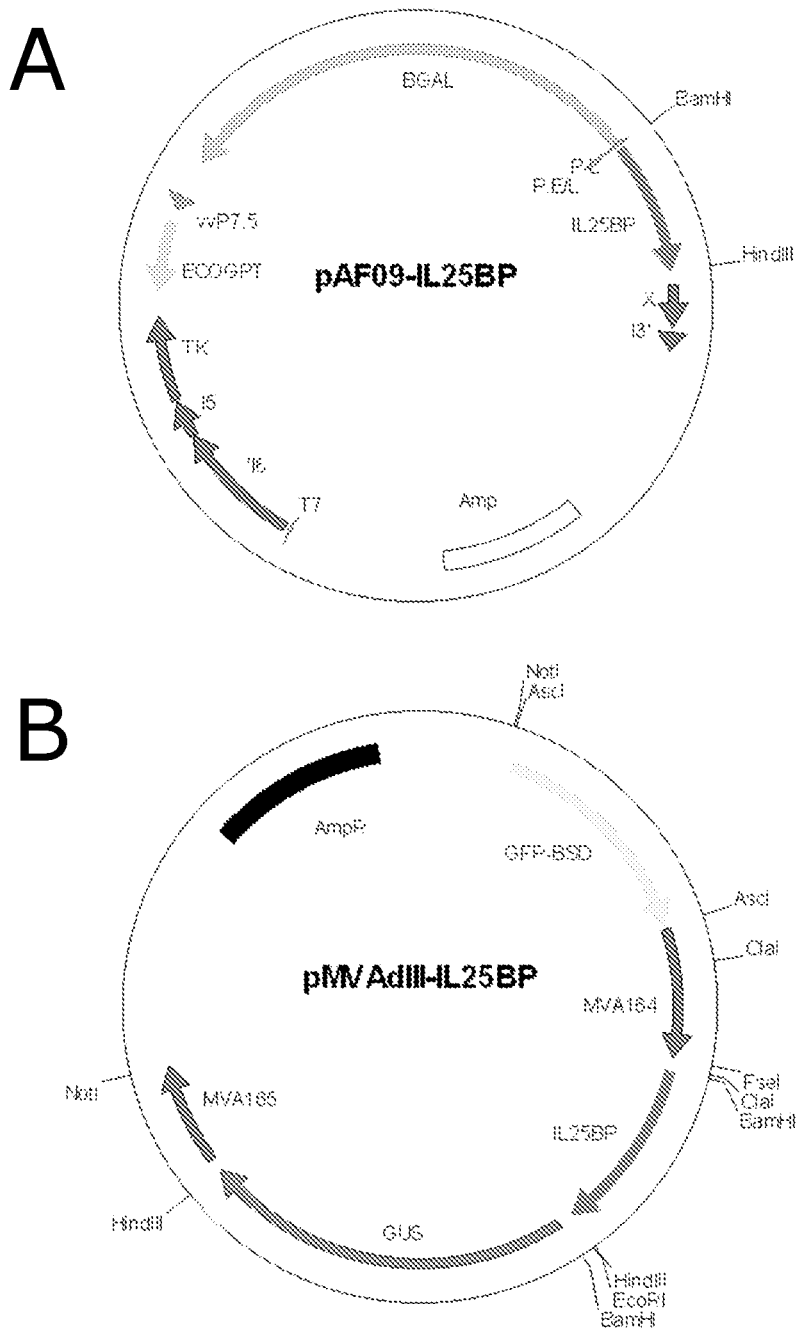
FIG. 1 shows a vector map of the (A) FPV vector pAF09-IL25BP, and (B) MVA vector pMVAdIII-IL25BP.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

The term "about" is used herein to refer to conditions (e.g., amounts, concentrations, time etc.) that vary by as much as 15%, 14%, 13%, 12%, 11%, 10%, 9%, 8%, 7%, 6%, 5%, 4%, 3%, 2%, or 1% to a specified condition.

The terms "administration concurrently" or "administering concurrently" or "co-administering" and the like refer to the administration of a single composition containing two or more actives, or the administration of each active as separate compositions and/or delivered by separate routes either contemporaneously or simultaneously or sequentially within a short enough period of time that the effective result is equivalent to that obtained when all such actives are administered as a single composition. By "simultaneously" is meant that the active agents are administered at substantially the same time, and desirably together in the same formulation. By "contemporaneously" it is meant that the active agents are administered closely in time, e.g., one agent is administered within from about 1 min to within about 1 d before or after another. Any contemporaneous time is useful. However, it will often be the case that when not administered simultaneously, the agents will be administered within about 1 min to within about 8 h and preferably within less than about 1 h to about 4 h. When administered contemporaneously, the agents are suitably administered at the same site on the subject. The term "same site" includes the exact location, but can be within about 0.5 cm to about 15 cm, preferably from within about 0.5 cm to about 5 cm. The term "separately" as used herein means that the agents are administered at an interval, for example at an interval of about a day to several weeks or months. The active agents may be administered in either order. The term "sequentially" as used herein means that the agents are administered in sequence, for example at an interval or intervals of minutes, hours, days or weeks. If appropriate the active agents may be administered in a regular repeating cycle.

As used herein, "and/or" refers to and encompasses any and all possible combinations of one or more of the associated listed items, as well as the lack of combinations when interpreted in the alternative (or).

The terms "antagonist" and "inhibitor" are used interchangeably herein to refer to any molecule that partially or fully blocks, inhibits, stops, diminishes, reduces, impedes, impairs or neutralizes one or more biological activities or functions of IL-25 or a receptor to which it binds (e.g., IL-25R) in any setting including, in vitro, in situ, or in vivo. Likewise, the terms "antagonize", "antagonizing", "inhibit", "inhibiting" and the like are used interchangeably herein to refer to blocking, inhibiting stopping, diminishing, reducing, impeding, impairing or neutralizing an activity or function as described for example above and elsewhere herein. By way of example, the terms "antagonize" and "inhibit" can refer to a decrease of about 10%, 20%, 30%, 40%, 50%, 60%, 70%, 80%, 90% or 100% in an activity, or function.

As used herein, the term "antigen" and its grammatically equivalents expressions (e.g., "antigenic") refer to a compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, and proteins. Common categories of antigens include, but are not limited to, viral antigens, bacterial antigens, fungal antigens, protozoa and other parasitic antigens, tumor antigens, antigens involved in autoimmune disease, allergy and graft rejection, toxins, and other miscellaneous antigens.

By "antigen-binding molecule" is meant a molecule that has binding affinity for a target antigen. It will be understood that this term extends to immunoglobulins, immunoglobulin fragments and non-immunoglobulin derived protein frameworks that exhibit antigen-binding activity. Representative antigen-binding molecules that are useful in the practice of the present invention include polyclonal and monoclonal antibodies as well as their fragments (such as Fab, Fab', F(ab')$_2$, Fv), single chain (scFv) and domain antibodies (including, for example, shark and camelid antibodies), and fusion proteins comprising an antibody, and any other modified configuration of the immunoglobulin molecule that comprises an antigen-binding/recognition site. An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called α, δ, ε, γ, and μ, respectively. The subunit structures and three-dimensional configurations of different classes of immunoglobulins are well known. Antigen-binding molecules also encompass dimeric antibodies, as well as multivalent forms of antibodies. In some embodiments, the antigen-binding molecules are chimeric antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, for example, U.S. Pat. No. 4,816,567; and Morrison et al., 1984, *Proc. Natl. Acad. Sci. USA* 81:6851-6855). Also contemplated, are humanized antibodies, which are generally produced by transferring complementarity determining regions (CDRs) from heavy and light variable chains of a non-human (e.g., rodent, preferably mouse) immunoglobulin into a human variable domain. Typical residues of human antibodies are then substituted in the framework regions of the non-human counterparts. The use of antibody components derived from humanized antibodies obviates potential problems associated with the immunogenicity of non-human constant regions. General techniques for cloning non-human, particularly murine, immunoglobulin variable domains are described, for example, by Orlandi et al. (1989, Proc. Natl. Acad. Sci. USA 86: 3833). Techniques for producing humanized monoclonal antibodies are described, for example, by Jones et al. (1986, *Nature* 321: 522), Carter et al. (1992, *Proc. Natl. Acad. Sci. USA* 89: 4285), Sandhu (1992, *Crit. Rev. Biotech.* 12: 437), Singer et al. (1993, *J. Immun.* 150: 2844), Sudhir (ed., Antibody Engineering Protocols, Humana Press, Inc. 1995), Kelley ("Engineering Therapeutic Antibodies," in Protein Engineering: Principles and Practice Cleland et al. (eds.), pages 399-434 (John Wiley & Sons, Inc. 1996), and by Queen et al., U.S. Pat. No. 5,693,762 (1997). Humanized antibodies include "primatized" antibodies in which the antigen-binding region of the antibody is derived from an antibody produced by immunizing macaque monkeys with the antigen of interest. Also contemplated as antigen-binding molecules are humanized antibodies.

By "autologous" is meant something (e.g., cells, tissues etc.) derived from the same organism.

The term "allogeneic" as used herein refers to cells, tissues, organisms etc. that are of different genetic constitution.

By "biologically active fragment" is meant a fragment of a full-length parent polypeptide which fragment retains an activity of the parent polypeptide. As used herein, the term "biologically active fragment" includes deletion mutants and small peptides, for example of at least 6, 7, 8, 9, 10, 11, 12, 13, 14, 15, 16, 17, 18, 19, 20, 21, 22, 23, 24, 25, 26, 27, 28, 29 or 30 contiguous amino acids, which comprise an activity of the parent polypeptide. Peptides of this type may be obtained through the application of standard recombinant nucleic acid techniques or synthesized using conventional liquid or solid phase synthesis techniques. For example, reference may be made to solution synthesis or solid phase synthesis as described, for example, in Chapter 9 entitled "Peptide Synthesis" by Atherton and Shephard which is included in a publication entitled "Synthetic Vaccines" edited by Nicholson and published by Blackwell Scientific Publications. Alternatively, peptides can be produced by digestion of a polypeptide of the invention with proteinases such as endoLys-C, endoArg-C, endoGlu-C and *staphylococcus* V8-protease. The digested fragments can be purified by, for example, high performance liquid chromatographic (HPLC) techniques.

As used herein, a "cellular preparation," refers to a composition comprising at least one cell population as an active ingredient.

By "coding sequence" is meant any nucleic acid sequence that contributes to the code for the polypeptide product of a gene or for the final mRNA product of a gene (e.g. the mRNA product of a gene following splicing). By contrast, the term "non-coding sequence" refers to any nucleic acid sequence that does not contribute to the code for the polypeptide product of a gene or for the final mRNA product of a gene.

Throughout this specification, unless the context requires otherwise, the words "comprise," "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The terms "construct" and "synthetic construct" are used interchangeably herein to refer to heterologous nucleic acid sequences that are operably linked to each other and may include sequences providing the expression of a polynucleotide in a host cell and optionally sequences that provide for the maintenance of the construct.

By "corresponds to" or "corresponding to" is meant an antigen which encodes an amino acid sequence that displays substantial sequence identity or similarity to an amino acid sequence in a target antigen. In general, the antigen will display at least about 30, 40, 50, 55, 60, 65, 70, 75, 80, 85, 90, 91, 92, 93, 94, 95, 96, 97, 98, 99% identity or similarity to at least a portion of the target antigen.

As used herein, "culturing," "culture" and the like refer to the set of procedures used in vitro where a population of cells (or a single cell) is incubated under conditions which have been shown to support the growth or maintenance of the cells in vitro. The art recognizes a wide number of formats, media, temperature ranges, gas concentrations etc. which need to be defined in a culture system. The parameters will vary based on the format selected and the specific needs of the individual who practices the methods herein disclosed. However, it is recognized that the determination of culture parameters is routine in nature.

By "effective amount", in the context of stimulating an immune response or treating or preventing a disease or condition, is meant the administration of that amount of composition to an individual in need thereof, either in a single dose or as part of a series, that is effective for that modulation, treatment or prevention. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials.

By "expression vector" is meant any autonomous genetic element capable of directing the synthesis of a protein encoded by the vector. Such expression vectors are known by practitioners in the art.

The term "gene" is used in its broadest context to include both a genomic DNA region corresponding to the gene as well as a cDNA sequence corresponding to exons or a recombinant molecule engineered to encode a functional form of a product.

The term "IL-25 receptor" as used herein means a receptor or a receptor complex mediating IL-25 signaling. IL-25 signaling requires two receptors, IL17RB and IL17RA, which may form a heteromeric complex. IL-25 binds to IL17RB with high affinity, whereas IL17RA does not bind IL-25 but is required for activating signaling pathways upon ligand binding (see, Rickel et al., *J Immunol*, 2008, 181: 4299-310). Thus, "IL-25 receptor" contemplates both IL17RB and IL17RA. The term "IL17RB" (also known as IL-17BR, CRL4, EVI27, IL17RH1, and MGC5245) as used herein means "interleukin 17 receptor B," a polypeptide having an amino acid sequence according to UniProtKB accession no. Q9NRM6, the product of an IL17RB gene (e.g., a human IL17RB gene (identified by GenBank accession no. AF212365)), and includes all of the variants, isoforms and species homologs of IL17RB. Both IL-25 and IL-17B are ligands for IL17RB, but the receptor binds IL-25 with higher affinity (see, Lee, et al., *J Biol Chem*, 2001, 276, 1660-64, 2001). The term "IL17RA," (also known as CD217, IL17R, CDw217, IL-17RA, hIL-17R, and MGC10262) as used herein means "interleukin 17 receptor A," a polypeptide having an amino acid sequence according to UniProt accession no. Q96F46, the product of an IL17RA gene (e.g., a human IL17RA gene (identified by GenBank accession no. BC011624)), and includes all of the variants, isoforms and species homologs of IL17RA. Variants of IL17RB and IL17RA also include soluble mature receptors.

The terms "IL-25" and "IL-25 polypeptide" (also commonly known as IL17E, and IL-17E) as used herein means "interleukin-25," a polypeptide having a sequence according to UniProt accession no. Q9H293, the product of an IL-25 gene (e.g., the human IL17E gene (identified by GenBank accession no. AF305200), and includes all of the variants, isoforms and species homologs of IL-25.

"IL-25 signaling" as used herein means the processes initiated by IL-25 or another IL-25 receptor ligand interacting with the IL-25 receptor on the cell surface, resulting in measurable changes in cell function. The IL-25 receptor complex includes IL17RB and IL17RA, and ligand binding activates downstream signal transduction pathways for example adaptor molecule TRAF6, JNK/p38 and ERK, and NFκB, leading to the production of cytokines and chemokines (see, Maezawa et al., *J Immunol*, 2006, 176: 1013-18). IL-25 signaling can be measured, for example, by assessing the amount of cytokines and chemokines produced upon induction with an IL-25 receptor ligand, for example measuring production of CXCL-8, IL-6, G-CSF, MCP-1, MIP-1.alpha., RANTES, or CCL2 (as described in Cai et al., *Cytokine*, 2001, 16: 10-21; Lee et al., *J Biol Chem*, 276: 1660-64; Pan et al., *J Immunol*, 2001, 167: 6559-67; Wong et al., *Am J Respir Cell Mol Biol*, 2005, 33: 186-194). The methods and suitable readout systems are well known in the art and are commercially available.

To enhance immune response ("immunoenhancement"), as is well-known in the art, means to increase the animal's capacity to respond to foreign or disease-specific antigens (e.g., cancer antigens) i.e., those cells primed to attack such antigens are increased in number, activity, and ability to detect and destroy those antigens. Strength of immune response is measured by standard tests including: direct measurement of peripheral blood lymphocytes by means known to the art; natural killer cell cytotoxicity assays (see, e.g., Provinciali M. et al. (1992, *J. Immunol. Meth.* 155: 19-24), cell proliferation assays (see, e.g., Vollenweider, I. And Groseurth, P. J. (1992, *J. Immunol. Meth.* 149: 133-135), immunoassays of immune cells and subsets (see, e.g., Loeffler, D. A., et al. (1992, *Cytom.* 13: 169-174); Rivoltini, L., et al. (1992, *Can. Immunol. Immunother.* 34: 241-251); or skin tests for cell-mediated immunity (see, e.g., Chang, A. E. et al. (1993, *Cancer Res.* 53: 1043-1050). Any statistically significant increase in strength of immune response as measured by the foregoing tests is considered "enhanced immune response", "immunoenhancement" or "immunopotentiation" as used herein. Enhanced immune response is also indicated by physical manifestations such as fever and inflammation, as well as healing of systemic and local infections, and reduction of symptoms in disease, i.e., decrease in tumor size, alleviation of symptoms of a disease or condition including, but not restricted to, leprosy, tuberculosis, malaria, aphthous ulcers, herpetic and papillomatous warts, gingivitis, arthrosclerosis, the concomitants of AIDS such as Kaposi's sarcoma, bronchial infections, and the like. Such physical manifestations also define "enhanced immune response" "immunoenhancement" or "immunopotentiation" as used herein.

Reference herein to "immuno-interactive" includes reference to any interaction, reaction, or other form of association between molecules and in particular where one of the molecules is, or mimics, a component of the immune system.

"Inactivation" of a cell is used herein to indicate that the cell has been rendered incapable of cell division to form progeny. The cell may nonetheless be capable of response to stimulus, or biosynthesis and/or secretion of cell products such as cytokines. Methods of inactivation are known in the art. Preferred methods of inactivation are treatment with toxins such as mitomycin C, or irradiation. Cells that have been fixed or permeabilized and are incapable of division are also examples of inactivated cells.

By "isolated" is meant material that is substantially or essentially free from components that normally accompany it in its native state.

A composition is "immunostimulatory" if it is capable of either: a) generating an immune response against an antigen (e.g., a tumor antigen) in a naïve individual; or b) reconstituting, boosting, or maintaining an immune response in an individual beyond what would occur if the compound or composition was not administered. A composition is immunogenic if it is capable of attaining either of these criteria when administered in single or multiple doses.

By "stimulating" is meant directly or indirectly increasing the level and/or functional activity of a target molecule. For example, an agent may indirectly stimulate the said level/activity by interacting with a molecule other than the target molecule. In this regard, indirect stimulation of a gene encoding a target polypeptide includes within its scope stimulation of the expression of a first nucleic acid molecule, wherein an expression product of the first nucleic acid molecule stimulates the expression of a nucleic acid molecule encoding the target polypeptide. In certain embodiments, "stimulation" or "stimulating" means that a desired/selected response is more efficient (e.g., at least 10%, 20%, 30%, 40%, 50%, 60% or more), more rapid (e.g., at least 10%, 20%, 30%, 40%, 50%, 60% or more), greater in magnitude (e.g., at least 10%, 20%, 30%, 40%, 50%, 60% or more), and/or more easily induced (e.g., at least 10%, 20%, 30%, 40%, 50%, 60% or more) than if the antigen had been used alone.

The term "5' non-coding region" is used herein in its broadest context to include all nucleotide sequences which are derived from the upstream region of an expressible gene, other than those sequences which encode amino acid residues which comprise the polypeptide product of said gene, wherein 5' non-coding region confers or activates or otherwise facilitates, at least in part, expression of the gene.

By "obtained from" is meant that a sample such as, for example, a nucleic acid extract or polypeptide extract is isolated from, or derived from, a particular source of the host. For example, the extract may be obtained from a tissue or a biological fluid isolated directly from the host.

The term "oligonucleotide" as used herein refers to a polymer composed of a multiplicity of nucleotide units (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotides and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule may vary depending on the particular application. An oligonucleotide is typically rather short in length, generally from about 10 to 30 nucleotides, but the term can refer to molecules of any length, although the term "polynucleotide" or "nucleic acid" is typically used for large oligonucleotides.

The term "operably connected" or "operably linked" as used herein means placing a structural gene under the regulatory control of a regulatory polynucleotide such as a promoter, which controls the transcription and optionally translation of the gene. For example, in the construction of heterologous promoter/structural gene combinations, it is generally preferred to position the genetic sequence or promoter at a distance from the gene transcription start site that is approximately the same as the distance between that genetic sequence or promoter and the gene it controls in its natural setting; i.e., the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting; i.e., the genes from which it is derived.

The terms "patient," "subject," "host" or "individual" used interchangeably herein, refer to any subject, particularly a vertebrate subject, and even more particularly a mammalian subject, for whom therapy or prophylaxis is desired. Suitable vertebrate animals that fall within the scope of the invention include, but are not restricted to, any member of the subphylum Chordata including primates, rodents (e.g., mice rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as canaries, budgerigars etc), marine mammals (e.g., dolphins, whales), reptiles (e.g., snakes, frogs, lizards etc), and fish. A preferred subject is a human in need of treatment or prophylaxis for a condition or disease, which is associated with the presence or aberrant expression of an antigen of interest. However, it will be understood that the aforementioned terms do not imply that symptoms are present.

By "pharmaceutically-acceptable carrier" is meant a solid or liquid filler, diluent or encapsulating substance that may be safely used in topical or systemic administration.

The term "pharmaceutically compatible salt" as used herein refers to a salt which is toxicologically safe for human and animal administration. This salt may be selected from a group including hydrochlorides, hydrobromides, hydroiodides, sulfates, bisulfates, nitrates, citrates, tartrates, bitartrates, phosphates, malates, maleates, napsylates, fumarates, succinates, acetates, terephthalates, pamoates and pectinates.

The term "polynucleotide" or "nucleic acid" as used herein designates mRNA, RNA, cRNA, cDNA or DNA. The term typically refers to oligonucleotides greater than 30 nucleotides in length.

The terms "polynucleotide variant" and refers to polynucleotides displaying substantial sequence identity with a reference polynucleotide sequence or polynucleotides that hybridize with a reference sequence under stringent conditions that are defined hereinafter. These terms also encompass polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide. The terms "polynucleotide variant" and "variant" also include naturally occurring allelic variants.

"Polypeptide," "peptide" and "protein" are used interchangeably herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally-occurring amino acid polymers.

The term "peptide variant," "polypeptide variant," and "variant" refer to polypeptides which vary from a reference polypeptide by the addition, deletion or substitution of at least one amino acid. It is well understood in the art that some amino acids may be changed to others with broadly similar properties without changing the nature of the activity of the polypeptide. Preferred variant polypeptides comprise conservative amino acid substitutions. Exemplary conservative substitutions in a polypeptide may be made according to the following table:

TABLE A

| ORIGINAL RESIDUE | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |

TABLE A-continued

| ORIGINAL RESIDUE | Exemplary Substitutions |
| --- | --- |
| Met | Leu, Ile, |
| Phe | Met, Leu, Tyr |
| Ser | Thr |
| Thr | Ser |
| Trp | Tyr |
| Tyr | Trp, Phe |
| Val | Ile, Leu |

The term "inactive variant" refers to a polypeptide which varies from a reference polypeptide by the addition, deletion or substitution of at least one amino acid that is important in conferring activity to the polypeptide. It is well understood in the art that some amino acids may be changed to disrupt critical interactions and therefore change the nature of the activity of the polypeptide. Suitably, an inactive variant polypeptide will have only around 50%, 45%, 40%, 35%, 20%, 19%, 18%, 17%, 16%, 15%, 14%, 13%, 12%, 11%, 10%, 9%, 8%, 7%, 6%, 5%, 4%, 3%, 2%%, 1%, less than 1% or 0% activity of the corresponding wild-type polypeptide.

Substantial changes in function are made by selecting substitutions that are less conservative than those shown in TABLE A. Other replacements would be non-conservative substitutions and relatively fewer of these may be tolerated. Generally, the substitutions which are likely to produce the greatest changes in a polypeptide's properties are those in which (a) a hydrophilic residue (e.g., Ser or Asn) is substituted for, or by, a hydrophobic residue (e.g., Ala, Leu, Ile, Phe or Val); (b) a cysteine or proline is substituted for, or by, any other residue; (c) a residue having an electropositive side chain (e.g., Arg, His or Lys) is substituted for, or by, an electronegative residue (e.g., Glu or Asp) or (d) a residue having a smaller side chain (e.g., Ala, Ser) or no side chain (e.g., Gly) is substituted for, or by, one having a bulky side chain (e.g., Phe or Trp).

Reference herein to a "promoter" is to be taken in its broadest context and includes the transcriptional regulatory sequences of a classical genomic gene, including the TATA box which is required for accurate transcription initiation, with or without a CCAAT box sequence and additional regulatory elements (i.e., upstream activating sequences, enhancers and silencers) which alter gene expression in response to developmental and/or environmental stimuli, or in a tissue-specific or cell-type-specific manner. A promoter is usually, but not necessarily, positioned upstream or 5', of a structural gene, the expression of which it regulates. Furthermore, the regulatory elements comprising a promoter are usually positioned within 2 kb of the start site of transcription of the gene. Preferred promoters according to the invention may contain additional copies of one or more specific regulatory elements to further enhance expression in a cell, and/or to alter the timing of expression of a structural gene to which it is operably connected.

The term "recombinant polynucleotide" as used herein refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably linked to the nucleotide sequence.

By "recombinant polypeptide" is meant a polypeptide made using recombinant techniques, i.e., through the expression of a recombinant polynucleotide.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

As used herein "stimulating" an immune or immunological response refers to administration of a composition that initiates, boosts, or maintains the capacity for the host's immune system to react to a target substance or antigen, such as a foreign molecule, an allogeneic cell, or a tumor cell, at a level higher than would otherwise occur. Stimulating a "primary" immune response refers herein to eliciting specific immune reactivity in a subject in which previous reactivity was not detected; for example, due to lack of exposure to the target antigen, refractoriness to the target, or immune suppression. Stimulating a "secondary" response refers to the reinitiation, boosting, or maintenance of reactivity in a subject in which previous reactivity was detected; for example, due to natural immunity, spontaneous immunization, or treatment using one or several compositions or procedures.

As used herein, the term "suppress" or "suppressing" means partially or totally blocking stimulation, decreasing, preventing, delaying activation, inactivating, desensitizing, inhibiting, or down regulating a measureable change in IL-25 signaling. For example, suppressing IL-25 signaling can be achieved by blocking IL-25 and IL-25 receptor interaction or suppressing IL-25 receptor expression.

The term "Th17" refers to a subclass of T helper cells that produce inter alia IL-17A, IL-17F, IL-21, IL-22, IL-26, interferon-gamma (IFN-γ), tumor necrosis factor-alpha (TNF-α), GM-CSF, and MIP-A, and which elicit inflammatory reactions associated with a cellular, i.e., non-immunoglobulin, response to a challenge. Thus, a Th17 cytokine response encompasses an immune response whose most prominent feature comprises abundant CD4+ helper T cell activation that is associated with increased levels of Th17 cytokines (e.g., IL-17A, IL-17F, IL-21, IL-22, IL-26, IFN-γ, TNF-α, etc.) relative to these cytokine amounts in the absence of activation. A Th17 cytokine response can also refer to the production of cytokines from other white blood cells and non-white blood cells. A Th17 cytokine response can include abundant CD8+ cytotoxic T lymphocyte activity including cytokine production, and the activation of type 1 T cytotoxic cells (including ILC1). A Th17 response is typically promoted by CD4+"Th17" T-helper cells however a Th17 response can include CD8+ type 1 T cytotoxic cells.

By "treatment," "treat," "treated" and the like is meant to include both prophylactic and therapeutic treatment, including but not limited to preventing, relieving, altering, reversing, affecting, inhibiting the development or progression of, ameliorating, or curing (1) a disease or condition associated with the presence or aberrant expression of a target antigen, or (2) a symptom of the disease or condition, or (3) a predisposition toward the disease or condition, including conferring protective immunity to a subject.

By "vector" is meant a nucleic acid molecule, preferably a DNA molecule derived, for example, from a plasmid, bacteriophage, or plant virus, into which a nucleic acid sequence may be inserted or cloned. A vector preferably contains one or more unique restriction sites and may be capable of autonomous replication in a defined host cell including a target cell or tissue or a progenitor cell or tissue thereof, or be integrable with the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. The vector may also include a selection marker such as an antibiotic resistance gene that can be used for selection of suitable transformants. Examples of such resistance genes are well known to those of skill in the art.

2. Compositions

The present invention is predicated at least in part on the determination that expression of the cytokine IL-25 plays an important role in regulating the functional avidity of innate lymphoid cells (ILC), and that T cell avidity is improved by inhibition of IL-25 function in the local milieu of the immune response, leading the inventors to discover that a subject's T cell mediated immune response may be enhanced by removal, inhibition or neutralization of IL-25 production and/or function in the local milieu of the immune response.

Based on these observations, the present inventors propose that more efficacious prophylactic or therapeutic immune responses to a target antigen can be achieved using compositions that comprise a first agent comprising an immune stimulator or a polynucleotide sequence from which a nucleotide sequence encoding an immune stimulator is expressible, wherein the immune stimulator stimulates or otherwise enhances an immune response to a target antigen in a subject, together with a second agent comprising an inhibitor of IL-25 function or a polynucleotide from which a nucleotide sequence encoding an inhibitor of IL-25 function is expressible. In specific embodiments, the compositions are introduced into antigen-presenting cells such that the first and second agents are co-located in or on or co-presented by the antigen-presenting cells. In some specific embodiments, the first agent and the second agent are not fused or conjugated to one another, but present as separate components in the composition.

2.1 Inhibitors of IL-25 Function

The inhibitor of IL-25 function includes any molecule or compound that directly or indirectly binds or physically associates with IL-25 or its receptor(s) (e.g., IL-25R) and that suitably blocks, inhibits or otherwise antagonizes at least one of its functions or activities (e.g., binding to or interaction with one or more surface molecules (e.g., receptors) present on white blood cells, especially lymphocytes and more especially ILC2). The binding or association may involve the formation of an induced magnetic field or paramagnetic field, covalent bond formation, an ionic interaction such as, for example, occur in an ionic lattice, a hydrogen bond or alternatively, a van der Waals interaction such as, for example, a dipole-dipole interaction, dipole-induced-dipole interaction, induced-dipole-induced-dipole interaction or a repulsive interaction or any combination of the above forces of attraction.

In certain embodiments, the inhibitor of IL-25 function is any molecule capable of specifically preventing activation of cellular receptors for IL-25. For example, inhibitors of this type can be selected from soluble, membrane-bound or defective IL-25 receptors or soluble IL-25 receptor subunits, including but not limited to IL-17 receptor A (IL17RA) and IL-17 receptor B (IL17RB) polypeptides. An illustrative IL17RA polypeptide sequence is shown in SEQ ID NO: 1 of U.S. Pat. No. 6,072,033 and deposited as UniProtKB accession no. Q96F46:

[SEQ ID NO: 1]
MGAARSPPSAVPGPLLGLLLLLLGVLAPGGASLRLLDHRALVCSQPGLNC

TVKNSTCLDDSWIHPRNLTPSSPKDLQIQLHFAHTQQGDLFPVAHIEWTL

QTDASILYLEGAELSVLQLNTNERLCVRFEFLSKLRHHHRRWRFTFSHFV

VDPDQEYEVTVHHLPKPIPDGDPNHQSKNFLVPDCEHARMKVTTPCMSSG

SLWDPNITVETLEAHQLRVSFTLWNESTHYQILLTSFPHMENHSCFEHMH

HIPAPRPEEFHQRSNVTLTLRNLKGCCRHQVQIQPFFSSCLNDCLRHSAT

VSCPEMPDTPEPIPDYMPLWVYWFITGISILLVGSVILLIVCMTWRLAGP

GSEKYSDDTKYTDGLPAADLIPPPLKPRKVWIIYSADHPLYVDVVLKFAQ

FLLTACGTEVALDLLEEQAISEAGVMTWVGRQKQEMVESNSKIIVLCSRG

TRAKWQALLGRGAPVRLRCDHGKPVGDLFTAAMNMILPDFKRPACFGTYV

VCYFSEVSCDGDVPDLFGAAPRYPLMDRFEEVYFRIQDLEMFQPGRMHRV

GELSGDNYLRSPGGRQLRAALDRFRDWQVRCPDWFECENLYSADDQDAPS

LDEEVFEEPLLPPGTGIVKRAPLVREPGSQACLAIDPLVGEEGGAAVAKL

EPHLQPRGQPAPQPLHTLVLAAEEGALVAAVEPGPLADGAAVRLALAGEG

EACPLLGSPGAGRNSVLFLPVDPEDSPLGSSTPMASPDLLPEDVREHLEG

LMLSLFEQSLSCQAQGGCSRPAMVLTDPHTPYEEEQRQSVQSDQGYISRS

SPQPPEGLTEMEEEEEEEQDPGKPALPLSPEDLESLRSLQRQLLFRQLQK

NSGWDTMGSESEGPSA

IL-17B and its many isoforms are known in the art, such as those disclosed and described in Tial et al., Oncogene, 19:2098 (2000). By way of an illustrative example, a suitable inhibitor of IL-25 function of this type is a soluble fragment of a human IL17RB polypeptide (e.g., the human IL17RB polypeptide deposited as UniProt accession no. Q9NRM6 and as set forth in SEQ ID NO: 2, below).

[SEQ ID NO: 2]
MSLVLLSLAALCRSAVPREPTVQCGSETGPSPEWMLQHDLIPGDLRDLRV

EPVTTSVATGDYSILMNVSWVLRADASIRLLKATKICVTGKSNFQSYSCV

RCNYTEAFQTQTRPSGGKWTFSYIGFPVELNTVYFIGAHNIPNANMNEDG

PSMSVNFTSPGCLDHIMKYKKKCVKAGSLWDPNITACKKNEETVEVNFTT

TPLGNRYMALIQHSTIIGFSQVFEPHQKKQTRASVVIPVTGDSEGATVQL

TPYFPTCGSDCIRHKGTVVLCPQTGVPFPLDNNKSKPGGWLPLLLLSLLV

ATWVLVAGIYLMWRHERIKKTSFSTTTLLPPIKVLVVYPSEICFHHTICY

FTEFLQNHCRSEVILEKWQKKKIAEMGPVQWLATQKKAADKVVFLLSNDV

NSVCDGTCGKSEGSPSENSQDLFPLAFNLFCSDLRSQIHLHKYVVVYFRE

IDTKDDYNALSVCPKYHLMKDATAFCAELLHVKQQVSAGKRSQACHDGCC

SL

More specifically, a particularly suitable soluble IL17RB polypeptide may lack the native transmembrane domain (i.e., lacking amino acid residues 293-313 of the wild-type human IL17RB polypeptide set forth in SEQ ID NO: 2). Accordingly, in some embodiments, the inhibitor of IL-25 function is an IL17RB polypeptide that comprises the extracellular domain (corresponding to amino acid residues 18-292 of the sequence set forth in SEQ ID NO: 2) or a fragment thereof. Optionally, the IL17RB polypeptide may also comprises the native signal sequence (i.e., residues 1-17 of the amino acid sequence set forth in SEQ ID NO: 2).

Thus, certain aspects of the present invention are drawn to agents (e.g., antigen-binding proteins) that block the association of IL-17RA with IL-17RB (and/or with additional receptor subunits) and thereby preventing formation of a functional receptor complex (i.e., a receptor complex that is capable of being activated). Illustrative examples of suitable inhibitors of this type are disclosed in U.S. Patent Publication No. 2014/0322238, all of which are incorporated herein by reference. For example, illustrative examples of suitable antibodies that bind IL-17RA are listed in TABLE B:

TABLE B

| Antibody | SEQ ID NO: | Description | SEQ ID NO: | Description |
| --- | --- | --- | --- | --- |
| 3.1404.1 | 3 | $AM_H14$ Vh | 9 | $AM_L14$ Vl |
| 4.361.1 | 4 | $AM_H17$ Vh | 10 | $AM_L17$ Vl |
| 4.16.1 | 5 | $AM_L19$ Vh | 11 | $AM_L19$ Vl |
| 381.1.1 | 6 | $AM_L22$ Vh | 12 | $AM_L22$ Vl |
| 3.454.1 | 7 | $AM_H23$ Vh | 13 | $AM_L23$ Vl |
| 3.454.1.1 | 8 | $AM_H24$ Vh | 14 | $AM_L24$ Vl | wherein:

SEQ ID NO: 3 is:
QVQLVQSGAEVKKPGASVKVSCKASGYTFTRYGISWVRQAPGQGLEWMGW

ISTYSGNTNYAQKLQGRVTMTTDTSTSTAYMELRSLRSDDTAVYYCARRQ

LYFDYWGQGTLVTVSS;

SEQ ID NO: 4 is:
QVQLVQSGAEVKKPGAAVKVSCKATGYTLTSYGISWVRQAPGQGLEWMGW

ISAYSGNTKYAQKLQGRVTMTTDTSTSTAYMELRSLRSDDTAVYYCARKQ

LVFDYWGQGTLVTVSS;

SEQ ID NO: 5 is:
QVQLVQSGAEVKKPGASVKVSCKASGYTLTSYGISWVRQAPGQGLEWMGW

ISAYSGNTKYAQKFQGRVTMTTDTSTSTAYMELRSLRSDDTAVYYCARRQ

LALDYWGQGTLVTVSS;

SEQ ID NO: 6 is:
QVQLVQSGAEVKKPGASVKVSCKASGYTFTRYGISWVRQAPGQGLEWMGW

ISAYSGNTNYAQKLQGRVTMTTDTSTSTAYMELRSLRSDDTAVYYCARRQ

LYFDYWGQGTLVTVSS;

SEQ ID NO: 7 is:
QVQLQESGPGLVKPSETLSLTCTVSGGSISSYYWSWIRQPAGKRLEWIGR

IYPSGRTNYNPSLKSRVTMSVDTSKNQFSLKLSSVTAADTAVYYCAREAY

ELQLGLYYYYGMDVWGQGTPVTVSS;

SEQ ID NO: 8 is:
QVQLQESGPGLVKPSETLSLTCTVSGGSISSYYWSWIRQAAGKRLEWIGR

IYPSGRTNYNPSLKSRVTMSVDTSKNQFSLKLSSVTAADTAVYYCAREAY

ELQLGLYYYYGMDVWGQGTPVTVSS;

-continued

SEQ ID NO: 9 is:
EIVMTQSPATLSVSPGERATLSCRASQSVSSNLAWFQQKPGQAPRPLIYD

ASTRATGVPARFSGSGSGTDFTLTISSLQSEDFAVYYCQQYDNWPLTFGG

GTKVEIK;

SEQ ID NO: 10 is:
EIVMTQSPATLSVSPGERATLSCRASQSVSSNLAWYQQKPGQAPRLLIYG

ASTRATGIPARFSGSGSGTEFTLTISSLQSEDFAVYSCQQYDNWPLTFGG

GTKVEIK;

SEQ ID NO: 11 is:
EIVMTQSPATLSVSPGERATLSCRASQSISSNLAWYQQKPGQAPRLLIYG

ASTRATGIPARFSDNGSGTEFTLTISSLQSEDFAVYFCQQYDTWPLTFGG

GTKVEIK;

SEQ ID NO: 12 is:
EIVMTQSPATLSVSPGERVTLSCRASQSVSSNLAWFQQKPGQAPRPLIYD

ASTRAAGIPARFSGSGSGTDFTLTISSLQSEDFAVYYCQQYDNWPLTFGG

GTKVEIK;

SEQ ID NO: 13 is:
DIQMTQSPSSLSASVGDRVTISCRASQGIINDLGWYQQKPGKAPKRLIYA

ASSLQSGVPSRFSGSGSGTEFTFTISSLQPEDFATYYCLQHNSYPPTFGQ

GTKVEIK;
and

SEQ ID NO: 14
DIVMTQSPLSLPVTLGQPASISCRSSQSLVYSDGHTCLNWFQQRPGQSPR

RLIYKVSNWDSGVPDRFSGSGSGTDFTLKISRVEADDVGVYYCMQGTHWP

LCSFGQGTKLEI.

In certain embodiments, the inhibitor of IL-25 function is an inactive variant form of IL-25. For example, an inactive variant IL-25 polypeptides may be distinguished from a wild-type IL-25 polypeptide by one or more amino acids. By way of an illustrative example, a suitable wild-type polypeptide is the human IL-25 polypeptides, as identified by UniProt accession no. Q9H293, and as set forth below:

[SEQ ID NO: 15]
MRERPRLGEDSSLISLFLQVVAFLAMVMGTHTYSHWPSCCPSKGQDTSEE

LLRWSTVPVPPLEPARPNRHPESCRASEDGPLNSRAISPWRYELDRDLNR

LPQDLYHARCLCPHCVSLQTGSHMDPRGNSELLYHNQTVFYRRPCHGEKG

THKGYCLERRLYRVSLACVCVRPRVMG.

Alternatively, such an inhibitor can be an antigen-binding molecule that is immuno-interactive with IL-25 receptor. In these embodiments, the antigen-binding molecule may bind to the IL-25 receptor but will not signal via the receptor, thus blocking any host IL-25 signaling (such antigen-binding molecules are also referred to herein as antagonistic antigen-binding molecules). In other embodiments, the inhibitor of IL-25 function is an antigen-binding molecule that is immuno-interactive with at least a portion of IL-25. In these embodiments, the antigen-binding molecules can be immuno-interactive with an active or an inactive form of IL-25, the difference being that antigen-binding molecules to the active cytokine are more likely to recognize epitopes that are only present in the active conformation. Representative examples of such inhibitors include the antibodies disclosed in U.S. Pat. Nos. 8,785,605 and 8,658,169, and U.S. Pat. Appl. Pub. No. 2016/0083466.

By way of a specific example, one such IL-25 antibody comprises:
(a) an antibody VL domain comprising a CDR1 having the amino acid sequence SASQGISNYLN [SEQ IDNO:102], and CDR2 having the amino acid sequence YTSSLHS [SEQ IDNO:103], and a CDR3 having the amino acid sequence QQYLAFPYTF [SEQ IDNO:104]; and
(b) an antibody VH domain comprising a CDR1 having the amino acid sequence GYTMN [SEQ IDNO:105], a CDR2 having the amino acid sequence LINPYNGGT-SYNQNFKG [SEQ IDNO:106], and a CDR3 having the amino acid sequence EDYDGYLYFAMY [SEQ IDNO:107].

By way of a specific example, one such IL-25 antibody comprises a VL domain comprising the amino acid sequence set forth in SEQ ID NO:16 and a VH domain comprising SEQ ID NO: 17 (i.e., the "M6" antibody),
wherein:

SEQ ID NO: 16 is:
DIQMTQTTSSLSASLGDRVTISCSASQGISNYLNWYQQKADGTVELLIY

YTSSLHSGVPSRFSGSGSGTDYSLTISNLEPEDIATYYCQQYSKLPYTF

GGGTKLEIK;
and

SEQ ID NO: 17 is:
EVQLQQSGPELVKPGASMKISCKASGYSFTDYTMNWVKQSHGKNLEWIG

LINPYNGGTSYNQNFKGKATLTVDKSSSTAYMELLSLTSEDSAVYYCAR

EGYDGYLYFAMDYWGQGTSVTVS.

In alternative embodiments, the IL-25 antibody binds one or more amino acid sequences of human IL-25 selected from the group SEDGPLNSRAISPWRY (SEQ ID NO: 108), DLNRLPQDLYHARCLCPHC (SEQ ID NO: 109), and RLYRVSL (SEQ ID NO: 110).

Yet other examples of suitable antibodies comprise:
(a) an antibody VL domain comprising a CDR1 having an amino acid sequence selected from the group consisting of SEQ ID NOs: 18, 19, 20, 21, 22, 23, 24, 25, 26, 27, 28, 29, 30, 31, 32 and 33; a CDR2 having an amino acid sequence selected from the group consisting of SEQ ID NOs: 34, 35, 36, 37, 38 and 39; and a CDR3 having an amino acid sequence selected from the group consisting of SEQ ID NOs: 40, 41, 42, 43, 44, 45, 46, 47, 48, 49, 50, 52, 53 and 54; and
(b) an antibody VH domain comprising a CDR1 having the amino acid sequence selected from the group consisting of SEQ ID NOs: 55, 56, 57, 58, 59, 60, 61, 62, 63, 64, 65, 66, 67, 68, 69 and 70; a CDR2 having an amino acid sequence selected from the group consisting of SEQ ID NOs: 71, 72, 73, 74, 75, 76, 77, 78, 79, 80, 81 and 82; a CDR3 having an amino acid sequence selected from the group consisting of SEQ ID NOs: 83, 84, 85, 86, 87, 88, 89, 90, 91, 92, 93, 94, 95, 97, 98 and 99,
wherein:

SEQ ID NO: 18 is:
QSIGSY;

SEQ ID NO: 19 is:
QSISSY;

SEQ ID NO: 20 is:
QSVFLGSNNKNY;

-continued

SEQ ID NO: 21 is:
QSVLYSSNNKNY;

SEQ ID NO: 22 is:
QDINNY;

SEQ ID NO: 23 is:
QSISSY;

SEQ ID NO: 24 is:
QGITNY;

SEQ ID NO: 25 is:
QNINSH;

SEQ ID NO: 26 is:
QNILLTSSNKNY;

SEQ ID NO: 27 is:
QDINSY;

SEQ ID NO: 28 is:
QSVLDSSNNKN;

SEQ ID NO: 29 is:
QSVLDSSNNKNY;

SEQ ID NO: 30 is:
QNVLITSNNKNY;

SEQ ID NO: 31 is:
QTIYSY;

SEQ ID NO: 32 is:
QSILYNSDNKNY;

SEQ ID NO: 33 is:
QDISSF;

SEQ ID NO: 34 is:
AAS;

SEQ ID NO: 35 is:
WAS;

SEQ ID NO: 36 is:
WSS;

SEQ ID NO: 37 is:
STS;

SEQ ID NO: 38 is:
TAS;

SEQ ID NO: 39 is:
DAS;

SEQ ID NO: 40 is:
QQTYSTPIT;

SEQ ID NO: 41 is:
QQYFITPLT;

SEQ ID NO: 42 is:
QQYFSTPWT;

SEQ ID NO: 43 is:
QQTFITPLT;

SEQ ID NO: 44 is:
QQSYLTPLT;

SEQ ID NO: 45 is:
QQYGSAPWT;

SEQ ID NO: 46 is:
QQTYITPLT;

SEQ ID NO: 47 is:
QQYYITPFT;

-continued

SEQ ID NO: 48 is:
QHLSSFPPT;

SEQ ID NO: 49 is:
QQYYFTPLT;

SEQ ID NO: 50 is:
QQFYNSPWT;

SEQ ID NO: 51 is:
QQYYSTPFT;

SEQ ID NO: 52 is:
QQTYSTPLT;

SEQ ID NO: 53 is:
QQYFFTPFT;

SEQ ID NO: 36 is:
WSS;

SEQ ID NO: 37 is:
STS;

SEQ ID NO: 38 is:
TAS;

SEQ ID NO: 39 is:
DAS;

SEQ ID NO: 40 is:
QQTYSTPIT;

SEQ ID NO: 41 is:
QQYFITPLT;

SEQ ID NO: 54 is:
QQVNSYPIT;

SEQ ID NO: 55 is:
GFTFSNYD;

SEQ ID NO: 56 is:
GFTFSNAW;

SEQ ID NO: 57 is:
GYTFTSYG;

SEQ ID NO: 58 is:
GYTFTNYG;

SEQ ID NO: 59 is:
GYTFSSYG;

SEQ ID NO: 60 is:
GGSISSHY;

SEQ ID NO: 61 is:
GGSISSYF;

SEQ ID NO: 62 is:
GGSISNYF;

SEQ ID NO: 63 is:
GGSISSYY;

SEQ ID NO: 64 is:
GGSISDYY;

SEQ ID NO: 65 is:
GGSINSYY;

SEQ ID NO: 66 is:
GGSINSYS;

SEQ ID NO: 67 is:
GASISNYY;

SEQ ID NO: 68 is:
DFAFTTYG;

-continued

SEQ ID NO: 69 is:
EYTFSNYG;

SEQ ID NO: 70 is:
SGSIRSSNYY;

SEQ ID NO: 71 is:
IERKTDGGTT;

SEQ ID NO: 72 is:
ARVPITGTTWFDP;

SEQ ID NO: 73 is:
IYYSGST;

SEQ ID NO: 74 is:
IFYSGNT;

SEQ ID NO: 75 is:
IDYSGST;

SEQ ID NO: 76 is:
ISAYNDNT;

SEQ ID NO: 77 is:
NYNSGST;

SEQ ID NO: 78 is:
ISAYNGNT;

SEQ ID NO: 79 is:
IGAYSGFT;

SEQ ID NO: 80 is:
IYYSGNT;

SEQ ID NO: 81 is:
IYNSENT;

SEQ ID NO: 82 is:
IGSAGDT;

SEQ ID NO: 83 is:
TTVGPYSVPFDY;

SEQ ID NO: 84 is:
ARVPITGTTWFDP;

SEQ ID NO: 85 is:
ARVRFSDYELNWFDP;

SEQ ID NO: 86 is:
ARVPLQWFGESF;

SEQ ID NO: 87 is:
ARVGTGTDSYFDF;

SEQ ID NO: 88 is:
ARVPITGTTSSFDF;

SEQ ID NO: 89 is:
ARHDYNDYELNYFDL;

SEQ ID NO: 90 is:
ARQEIINFELNWFDP;

SEQ ID NO: 91 is:
ARGYNWNYEIAWFDP;

SEQ ID NO: 92 is:
ARDPDYCSSNTCSDAFDL;

SEQ ID NO: 93 is:
ARHYFDSGTYELGY;

SEQ ID NO: 94 is:
ARDGYSSSGFYYFGM;

SEQ ID NO: 95 is:
ARGVIWNYELREF;

-continued

SEQ ID NO: 96 is:
ARQGYSDYELNWFDP;

SEQ ID NO: 97 is:
ARTYNWNYEIGAM;

SEQ ID NO: 98 is:
ARHDSDYELYGMDV;
and

SEQ ID NO: 99 is:
ARGDNWNYVSWFF.

By way of yet another specific example, another suitable antibody is the "2C3" antibody as disclosed in the International Patent Publication No WO2008/129263, in which the IL-25 antibody comprises a VL domain comprising the amino acid sequence set forth in SEQ ID NO: 16; and/or a VH domain comprising the amino acid sequence set forth in SEQ ID NO: 17. In some embodiments, the inhibitor of IL-25 function is an antisense or siRNA molecule designed against IL-25 gene or an IL-25 receptor gene (for example, such as IL-25 siRNA (catalogue sc-105567) available from Santa Cruz Biotechnology, Texas, U.S.A.).

Peptides, oligonucleotides, or small molecules blocking the interaction between IL-25 and the IL-25 receptor can be used. Such agents and inhibitors can also be peptides, proteins, fusion proteins, or small molecules that prevent interaction of IL-25 with an IL-25 receptor. Agents inhibiting IL-25 function that are suitable for use with the present invention have been previously described, for example, the peptide IL-25 variants disclosed in U.S. Pat. No. 6,562,578, and the IL17R like proteins disclosed in U.S. Pat. No. 6,635,443.

2.2 Immune-Stimulating Agents 2.2.1 Antigens

The present invention contemplates the use of the compositions of the invention of an immune stimulator comprising any antigen that corresponds to at least a portion of a target antigen of interest for stimulating an immune response to the target antigen. The antigen that corresponds to at least a portion of the target antigen may be in soluble form (e.g., a peptide or polypeptide) when expressed.

Target antigens useful in the present invention are typically proteinaceous molecules, representative examples of which include polypeptides and peptides. Target antigens may be selected from endogenous antigens produced by a host or exogenous antigens that are foreign to the host. Suitable endogenous antigens include, but are not restricted to, cancer or tumor antigens. Non-limiting examples of cancer or tumor antigens include antigens from a cancer or tumor selected from ABL1 proto-oncogene, AIDS related cancers (e.g., Kaposi sarcoma), acoustic neuroma, acute lymphocytic leukemia, acute myeloid leukemia, adenocystic carcinoma, adrenocortical cancer, agnogenic myeloid metaplasia, alopecia, alveolar soft-part sarcoma, anal cancer, angiosarcoma, aplastic anaemia, astrocytoma, ataxia-telangiectasia, basal cell carcinoma (skin), bladder cancer, bone cancers, bowel cancer, brain stem glioma, brain and CNS tumors, breast cancer, CNS tumors, carcinoid tumors, cervical cancer, childhood brain tumors, childhood cancer, childhood leukemia, childhood soft tissue sarcoma, chondrosarcoma, choriocarcinoma, chronic lymphocytic leukemia, chronic myeloid leukemia, colorectal cancers, cutaneous T-cell lymphoma, dermatofibrosarcoma protuberans, desmoplastic small round cell tumor, ductal carcinoma, endocrine cancers, endometrial cancer, ependymoma, esophageal cancer, Ewing's Sarcoma, extra-hepatic bile duct cancer, eye cancer, melanoma, retinoblastoma, fallopian tube cancer, Fanconi anemia, fibrosarcoma, gall bladder cancer, gastric cancer, gastrointestinal cancers, gastrointestinal-carcinoid-tumor, genitourinary cancers, germ cell tumors, gestational-trophoblastic-disease, glioma, gynecological cancers, hematological malignancies, hairy cell leukemia, head and neck cancer, hepatocellular cancer, hereditary breast cancer, histiocytosis, Hodgkin's disease, human papillomavirus, hydatidiform mole, hypercalcemia, hypopharynx cancer, intraocular melanoma, islet cell cancer, Kaposi's sarcoma, kidney cancer, Langerhans cell histiocytosis, laryngeal cancer, leiomyosarcoma, leukemia, Li-Fraumeni syndrome, lip cancer, liposarcoma, liver cancer, lung cancer, lymphedema, lymphoma, Hodgkin's lymphoma, non-Hodgkin's lymphoma, male breast cancer, malignant-rhabdoid tumor of kidney, medulloblastoma, melanoma, Merkel cell cancer, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nephroblastoma, neuroblastoma, neurofibromatosis, Nijmegen breakage syndrome, non-melanoma skin cancer, non-small-cell-lung-cancer (NSCLC), ocular cancers, esophageal cancer, oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal tumors, pituitary cancer, polycythemia vera, prostate cancer, rare cancers and associated disorders, renal cell carcinoma, retinoblastoma, rhabdomyosarcoma, Rothmund-Thomson syndrome, salivary gland cancer, sarcoma, schwannoma, Sezary syndrome, skin cancer, small cell lung cancer (SCLC), small intestine cancer, soft tissue sarcoma, spinal cord tumors, squamous-cell-carcinoma-(skin), stomach cancer, synovial sarcoma, testicular cancer, thymus cancer, thyroid cancer, transitional-cell-cancer-(bladder), transitional-cell-cancer-(renal-pelvis-/-ureter), trophoblastic cancer, urethral cancer, urinary system cancer, uroplakins, uterine sarcoma, uterus cancer, vaginal cancer, vulva cancer, Waldenstrom's macroglobulinemia, Wilms' tumor. In certain embodiments, the cancer or tumor relates to nasopharyngeal cancer. Illustrative examples of nasopharyngeal cancer antigens include EBNA-1, LMP-1, LMP-2, or a combination thereof. Other tumor-specific antigens include, but are not limited to: etv6, aml1, cyclophilin b (acute lymphoblastic leukemia); Ig-idiotype (B cell lymphoma); E-cadherin, α-catenin, β-catenin, γ-catenin, p120ctn (glioma); p21ras (bladder cancer); p21ras (biliary cancer); MUC family, HER2/neu, c-erbB-2 (breast cancer); p53, p21ras (cervical carcinoma); p21ras, HER2/neu, c-erbB-2, MUC family, Cripto-1protein, Pim-1 protein (colon carcinoma); Colorectal associated antigen (CRC)-CO17-1A/GA733, APC (colorectal cancer); carcinoembryonic antigen (CEA) (colorectal cancer; choriocarcinoma); cyclophilin b (epithelial cell cancer); HER2/neu, c-erbB-2, ga733 glycoprotein (gastric cancer); α-fetoprotein (hepatocellular cancer); Imp-1, EBNA-1 (Hodgkin's lymphoma); CEA, MAGE-3, NY-ESO-1 (lung cancer); cyclophilin b (lymphoid cell-derived leukemia); melanocyte differentiation antigen (e.g., gp100, MART, Melan-A/MART-1, TRP-1, Tyros, TRP2, MC1R, MUC1F, MUC1R or a combination thereof) and melanoma-specific antigens (e.g., BAGE, GAGE-1, gp100In4, MAGE-1 (e.g., GenBank Accession No. X54156 and AA494311), MAGE-3, MAGE4, FRAME, TRP2IN2, NYNSO1a, NYNSO1b, LAGE1, p97 melanoma antigen (e.g., GenBank Accession No. M12154) p5 protein, gp75, oncofetal antigen, GM2 and GD2 gangliosides, cdc27, p21ras, gp100$^{Pmel117}$ or a combination thereof (melanoma); MUC family, p21ras (myeloma); HER2/neu, c-erbB-2 (non-small cell lung carcinoma); MUC family, HER2/neu, c-erbB-2, MAGE-A4, NY-ESO-1 (ovarian cancer); Prostate Specific Antigen (PSA) and its antigenic epitopes PSA-1, PSA-2, and PSA-3, PSMA, HER2/neu, c-erbB-2, ga733 glycoprotein (prostate cancer); HER2/neu, c-erbB-2 (renal cancer); viral products such as human papillomavirus proteins (squamous cell cancers of the cervix and esophagus); NY-ESO-1 (testicular cancer); and HTLV-1 epitopes (T cell leukemia).

Foreign or exogenous antigens are suitably selected from antigens of pathogenic organisms. Exemplary pathogenic organisms include, but are not limited to, viruses, bacteria, fungi, parasites, algae and protozoa and amoebae. Illustrative viruses include viruses responsible for diseases including, but not limited to, measles, mumps, rubella, poliomyelitis, hepatitis A, B (e.g., GenBank Accession No. E02707), and C (e.g., GenBank Accession No. E06890), as well as other hepatitis viruses, influenza, adenovirus (e.g., types 4 and 7), rabies (e.g., GenBank Accession No. M34678), yellow fever, Epstein-Barr virus and other herpesviruses such as papillomavirus, Ebola virus, influenza virus, Japanese encephalitis (e.g., GenBank Accession No. E07883), dengue (e.g., GenBank Accession No. M24444), hantavirus, Sendai virus, respiratory syncytial virus, orthomyxoviruses, vesicular stomatitis virus, visna virus, cytomegalovirus and human immunodeficiency virus (HIV) (e.g., GenBank Accession No. U18552). Any suitable antigen derived from such viruses are useful in the practice of the present invention. For example, illustrative retroviral antigens derived from HIV include, but are not limited to, antigens such as gene products of the gag, pol, and env genes, the Nef protein, reverse transcriptase, and other HIV components. Illustrative examples of hepatitis viral antigens include, but are not limited to, antigens such as the S, M, and L proteins of hepatitis B virus, the pre-S antigen of hepatitis B virus, and other hepatitis, e.g., hepatitis A, B, and C, viral components such as hepatitis C viral RNA. Illustrative examples of influenza viral antigens include; but are not limited to, antigens such as hemagglutinin and neuraminidase and other influenza viral components. Illustrative examples of measles viral antigens include, but are not limited to, antigens such as the measles virus fusion protein and other measles virus components. Illustrative examples of rubella viral antigens include, but are not limited to, antigens such as proteins E1 and E2 and other rubella virus components; rotaviral antigens such as VP7sc and other rotaviral components. Illustrative examples of Cytomegaloviral antigens include, but are not limited to, antigens such as envelope glycoprotein B and other Cytomegaloviral antigen components. Non-limiting examples of respiratory syncytial viral antigens include antigens such as the RSV fusion protein, the M2 protein and other respiratory syncytial viral antigen components. Illustrative examples of herpes simplex viral antigens include, but are not limited to, antigens such as immediate early proteins, glycoprotein D, and other herpes simplex viral antigen components. Non-limiting examples of varicella zoster viral antigens include antigens such as 9PI, gpII, and other varicella zoster viral antigen components. Non-limiting examples of Japanese encephalitis viral antigens include antigens such as proteins E, M-E, M-E-NS 1, NS 1, NS 1-NS2A, and other Japanese encephalitis viral antigen components. Representative examples of rabies viral antigens include, but are not limited to, antigens such as rabies glycoprotein, rabies nucleoprotein and other rabies viral antigen components. Illustrative examples of papillomavirus antigens include, but are not limited to, the L1 and L2 capsid proteins as well as the E6/E7 antigens associated with cervical cancers (see Fundamental Virology, Second Edition, eds. Fields, B. N. and Knipe, D. M., 1991, Raven Press, New York, for additional examples of viral antigens).

Illustrative examples of fungi include *Acremonium* spp., *Aspergillus* spp., *Basidiobolus* spp., *Bipolaris* spp., *Blastomyces dermatitidis*, *Candida* spp., *Cladophialophora carrionii*, *Coccidioides immitis*, *Conidiobolus* spp., *Cryptococcus* spp., *Curvularia* spp., *Epidermophyton* spp., *Exophiala jeanselmei*, *Exserohilum* spp., *Fonsecaea compacta*, *Fonsecaea pedrosoi*, *Fusarium oxysporum*, *Fusarium solani*, *Geotrichum candidum*, *Histoplasma capsulatum* var. *capsulatum*, *Histoplasma capsulatum* var. *duboisii*, *Hortae werneckii*, *Lacazia loboi*, *Lasiodiplodia theobromae*, *Leptosphaeria senegalensis*, *Madurella grisea*, *Madurella mycetomatis*, *Malassezia furfur*, *Microsporum* spp., *Neotestudina rosati*, *Onychocola canadensis*, *Paracoccidioides brasiliensis*, *Phialophora verrucosa*, *Piedraia hortae*, *Pityriasis versicolor*, *Pseudallescheria boydii*, *Pyrenochaeta romeroi*, *Rhizopus arrhizus*, *Scopulariopsis brevicaulis*, *Scytalidium dimidiatum*, *Sporothrix schenckii*, *Trichophyton* spp., *Trichosporon* spp., *Zygomycota fungi*, *Absidia corymbifera*, *Rhizomucor pusillus* and *Rhizopus arrhizus*. Thus, representative fungal antigens that can be used in the compositions and methods of the present invention include, but are not limited to, *candida* fungal antigen components; *histoplasma* fungal antigens such as heat shock protein 60 (HSP60) and other *histoplasma* fungal antigen components; cryptococcal fungal antigens such as capsular polysaccharides and other cryptococcal fungal antigen components; coccidioses fungal antigens such as spherule antigens and other coccidioses fungal antigen components; and tinea fungal antigens such as trichophytin and other coccidioses fungal antigen components.

Illustrative examples of bacteria include bacteria that are responsible for diseases including, but not restricted to, diphtheria (e.g., *Corynebacterium diphtheria*), pertussis (e.g., *Bordetella pertussis*, GenBank Accession No. M35274), tetanus (e.g., *Clostridium tetani*, GenBank Accession No. M64353), tuberculosis (e.g., *Mycobacterium tuberculosis*), bacterial pneumonias (e.g., *Haemophilus influenzae*.), cholera (e.g., *Vibrio cholerae*), anthrax (e.g., *Bacillus anthracis*), typhoid, plague, shigellosis (e.g., *Shigella dysenteriae*), botulism (e.g., *Clostridium botulinum*), salmonellosis (e.g., GenBank Accession No. L03833), peptic ulcers (e.g., *Helicobacter pylori*), Legionnaire's Disease, Lyme disease (e.g., GenBank Accession No. U59487). Other pathogenic bacteria include *Escherichia coli*, *Clostridium perfringens*, *Pseudomonas aeruginosa*, *Staphylococcus aureus* and *Streptococcus pyogenes*. Thus, bacterial antigens which can be used in the compositions and methods of the invention include, but are not limited to: pertussis bacterial antigens such as pertussis toxin, filamentous hemagglutinin, pertactin, FIM2, FIM3, adenylate cyclase and other pertussis bacterial antigen components; diphtheria bacterial antigens such as diphtheria toxin or toxoid and other diphtheria bacterial antigen components; tetanus bacterial antigens such as tetanus toxin or toxoid and other tetanus bacterial antigen components, streptococcal bacterial antigens such as M proteins and other streptococcal bacterial antigen components; gram-negative bacilli bacterial antigens such as lipopolysaccharides and other gram-negative bacterial antigen components; *Mycobacterium tuberculosis* bacterial antigens such as mycolic acid, heat shock protein 65 (HSP65), antigen 85A, the 30 kDa major secreted protein (also known as, antigen 856), and other mycobacterial antigen components; *Helicobacter pylori* bacterial antigen components, pneumococcal bacterial antigens such as pneumolysin, pneumococcal capsular polysaccharides and other pneumococcal bacterial antigen components; *Haemophilus influenza* bacterial antigens such as capsular polysaccharides and other *Haemophilus influenza* bacterial antigen components; anthrax bacterial antigens such as anthrax protective antigen and other anthrax bacterial antigen components; rickettsiae bacterial antigens such as rompA and other rickettsiae bacterial antigen component. Also included with the bacterial antigens described herein are any other bacterial, mycobacterial, mycoplasmal, rickettsial, or chlamydial antigens.

Illustrative examples of protozoa include protozoa that are responsible for diseases including, but not limited to, malaria (e.g., GenBank Accession No. X53832), hookworm, onchocerciasis (e.g., GenBank Accession No. M27807), schistosomiasis (e.g., GenBank Accession No. LOS 198), toxoplasmosis, trypanosomiasis, leishmaniasis, giardiasis (GenBank Accession No. M33641), amoebiasis, filariasis (e.g., GenBank Accession No. J03266), borreliosis, and trichinosis. Thus, protozoal antigens which can be used in the compositions and methods of the invention include, but are not limited to: *Plasmodium falciparum* antigens such as merozoite surface antigens, sporozoite surface antigens, circumsporozoite antigens, gametocyte/gamete surface antigens, blood-stage antigen pf 155/RESA and other plasmodial antigen components; *toxoplasma* antigens such as SAG-1, p30 and other toxoplasmal antigen components; schistosomae antigens such as glutathione-S-transferase, paramyosin, and other schistosomal antigen components; *Leishmania major* and other leishmaniae antigens such as gp63, lipophosphoglycan and its associated protein and other leishmanial antigen components; and *Trypanosoma cruzi* antigens such as the 75-77 kDa antigen, the 56 kDa antigen and other trypanosomal antigen components.

The present invention also contemplates toxin components as antigens. Illustrative examples of toxins include, but are not restricted to, staphylococcal enterotoxins, toxic shock syndrome toxin; retroviral antigens (e.g., antigens derived from HIV), streptococcal antigens, staphylococcal enterotoxin-A (SEA), staphylococcal enterotoxin-B (SEB), staphylococcal enterotoxin$_{1-3}$ (SE$_{1-3}$), staphylococcal enterotoxin-D (SED), staphylococcal enterotoxin-E (SEE) as well as toxins derived from *mycoplasma*, *mycobacterium*, and herpes viruses.

Peptide antigens may be of any suitable size that can be utilized to stimulate or inhibit an immune response to a target antigen of interest. A number of factors can influence the choice of peptide size. For example, the size of a peptide can be chosen such that it includes, or corresponds to the size of, T cell epitopes and/or B cell epitopes, and their processing requirements. Practitioners in the art will recognize that class I-restricted T cell epitopes are typically between 8 and 10 amino acid residues in length and if placed next to unnatural flanking residues, such epitopes can generally require 2 to 3 natural flanking amino acid residues to ensure that they are efficiently processed and presented. Class II-restricted T cell epitopes usually range between 12 and 25 amino acid residues in length and may not require natural flanking residues for efficient proteolytic processing although it is believed that natural flanking residues may play a role. Another important feature of class II-restricted epitopes is that they generally contain a core of 9-10 amino acid residues in the middle which bind specifically to class II MHC molecules with flanking sequences either side of this core stabilizing binding by associating with conserved structures on either side of class II MHC antigens in a sequence independent manner. Thus the functional region of class II-restricted epitopes is typically less than about 15 amino acid residues long. The size of linear B cell epitopes and the factors affecting their processing, like class II-restricted epitopes, are quite variable although such epitopes are frequently smaller in size than 15 amino acid residues. From the foregoing, it is advantageous, but not essential, that the size of the peptide is at least 6, 7, 8, 9, 10, 11, 12, 13, 14, 15, 20, 25, 30 amino acid residues. Suitably, the size of the peptide is no more than about 500, 200, 100, 80, 60, 50, 40 amino acid residues. In certain advantageous embodiments, the size of the peptide is sufficient for presentation by an antigen-presenting cell of a T cell and/or a B cell epitope contained within the peptide.

Criteria for identifying and selecting effective antigenic peptides (e.g., minimal peptide sequences capable of eliciting an immune response) can be found in the art. For example, Apostolopoulos et al., (*Curr Opin Mol Ther*, 2000, 2: 29-36) discusses the strategy for identifying minimal antigenic peptide sequences based on an understanding of the three-dimensional structure of an antigen-presenting molecule and its interaction with both an antigenic peptide and T cell receptor. Shastri (*Curr Opin Immunol*, 1996, 8: 271-277) discloses how to distinguish rare peptides that serve to activate T cells from the thousands of peptides normally bound to MHC molecules.

2.3 Compositions

Exemplary compositions of the present invention include vaccines or constructs, including but not limited to recombinant vaccines.

In some embodiments, the immunostimulatory compositions have any one or more of the following characteristics:

(a) stimulate or induce an antigen-specific Th17 response (e.g., an increase in cytokine expression of any one of IL-17A, IL-22, TNF-α, IL-17F, IL-21, IL-26, GM-CSF, and MIP-A);

(b) stimulate or induce an antigen-specific Th1 response (e.g., of IFN-γ, IL-2 and TNF-β);

(c) suppress the expression of one or more of IL-13, IL-4, IL-5 and IL-9 by ILC2; and (d) suppressing an Th2 immune response (e.g., reduces stimulation of Th2 responses by conventional dendritic cells).

In some embodiments, the composition comprises a nucleic acid composition comprising: a first agent comprising a coding sequence for an immune stimulator operably linked to a regulatory polynucleotide, wherein the immune stimulator stimulates or otherwise enhances an immune response to a target antigen in a subject and a second agent comprising a coding sequence for an inhibitor of IL-25 function operably linked to a regulatory polynucleotide and from which a nucleotide sequence encoding an inhibitor of IL-25 function is expressible. The regulatory polynucleotide may be the same or different.

In some embodiments, the first and second polynucleotides are located on the same construct (or expression vector). In other embodiments, the first and second polynucleotides are located on different constructs.

The regulatory polynucleotide suitably comprises transcriptional and/or translational control sequences, which will be compatible for expression in the cell or tissue type of interest. Typically, the transcriptional and translational regulatory control sequences include, but are not limited to, a promoter sequence, a 5' non-coding region, a cis-regulatory region such as a functional binding site for transcriptional regulatory protein or translational regulatory protein, an upstream open reading frame, ribosomal-binding sequences, transcriptional start site, translational start site, and/or nucleotide sequence which encodes a leader sequence, termination codon, translational stop site and a 3' non-translated region. Constitutive or inducible promoters as known in the art are contemplated by the invention. The promoters may be either naturally occurring promoters, or hybrid promoters that combine elements of more than one promoter. Promoter sequences contemplated by the present invention may be native to the organism of interest or may be derived from an alternative source, where the region is functional in the chosen organism. The choice of promoter will differ depending on the intended host. For example, promoters which could be used for expression in mammalian cells generally include the metallothionein promoter, which can be induced in response to heavy metals such as cadmium, the β-actin promoter as well as viral promoters such as the SV40 large T antigen promoter, human cytomegalovirus (CMV) immediate early (IE) promoter, rous sarcoma virus LTR promoter, adenovirus promoter, or a HPV promoter, particularly the HPV upstream regulatory region (URR) may also be used. All these promoters are well described and readily available in the art. Alternatively, the promoter may be lineage specific and, in this regard, epithelial-specific promoters are particularly desirable such as, but not limited to, promoters of the following genes transglutaminase type 1, involucrin, loricrin, SPR genes and filaggrin as well as those of keratin genes (e.g., K10, K14, K5, K1).

The synthetic construct (or expression vector) may also comprise a 3' non-translated sequence. A 3' non-translated sequence refers to that portion of a gene comprising a DNA segment that contains a polyadenylation signal and any other regulatory signals capable of effecting mRNA processing or gene expression. The polyadenylation signal is characterized by effecting the addition of polyadenylic acid tracts to the 3' end of the mRNA precursor. Polyadenylation signals are commonly recognized by the presence of homology to the canonical form 5' AATAAA-3' although variations are not uncommon. The 3' non-translated regulatory DNA sequence preferably includes from about 50 to 1,000 nucleotide base pairs and may contain transcriptional and translational termination sequences in addition to a polyadenylation signal and any other regulatory signals capable of effecting mRNA processing or gene expression.

In some embodiments, the synthetic construct (or expression vector) further contains a screenable marker gene to permit identification of cells containing the synthetic construct. Screenable genes (e.g., lacZ, gfp, etc.) are well known in the art and will be compatible for expression in a particular cell or tissue type.

It will be understood, however, that expression of protein-encoding polynucleotides in heterologous systems is now well known, and the present invention is not directed to or dependent on any particular vector, transcriptional control sequence or technique for its production. Rather, synthetic polynucleotides prepared according to the methods as set forth herein may be introduced into selected cells or tissues or into a precursors or progenitors thereof in any suitable manner in conjunction with any suitable synthetic construct or vector, and the synthetic polynucleotides may be expressed with known promoters in any conventional manner.

The synthetic constructs or vectors can be introduced into suitable host cells for expression using any of a number of non-viral or viral gene delivery vectors. For example, retroviruses (in particular, lentiviral vectors) provide a convenient platform for gene delivery systems. A coding sequence of interest (for example, a sequence useful for gene therapy applications) can be inserted into a gene delivery vector and packaged in retroviral particles using techniques known in the art. Recombinant virus can then be isolated and delivered to cells of the subject either in vivo or ex vivo.

In one illustrative embodiment, retroviruses provide a convenient and effective platform for gene delivery systems. A selected nucleotide sequence that encodes an antigen corresponding to the target antigen and a selected nucleotide sequence that encodes an inhibitor of IL-25 function (where the two selected nucleotide sequences can be part of the same sequence or separate sequences) can be inserted into a construct or vector and packaged in retroviral particles using techniques known in the art. The recombinant virus can then be isolated and delivered to a subject. Several illustrative retroviral systems have been described examples of which include: U.S. Pat. No. 5,219,740; Miller and Rosman, *Bio Techniques,* 1989, 7: 980-990; Miller, A. D., *Human Gene Therapy,* 1990, 1: 5-14; Scarpa et al., *Virology,* 1991, 180: 849-852; Burns et al., *Proc Nat Acad Sci USA,* 1993, 90: 8033-8037; and Boris-Lawrie and Temin, *Cur Opin Genet Develop,* 1993, 3: 102-109.

In addition, several illustrative adenovirus-based systems have also been described. Unlike retroviruses which integrate into the host genome, adenoviruses persist extrachromosomally thus minimizing the risks associated with insertional mutagenesis (see, e.g., Haj-Ahmad and Graham, *J Virol,* 1986, 57: 267-274; Bett et al., *J Virol,* 1993, 67: 5911-5921; Mittereder et al., *Human Gene Therapy,* 1994, 5: 717-729; Seth et al., *J Virol,* 1994, 68: 933-940; Barr et al., *Gene Therapy,* 1994, 1: 51-58; Berkner, K. L., *Bio Techniques,* 1988, 6: 616-629; and Rich et al., *Human Gene Therapy,* 1993, 4: 461-476).

Various adeno-associated virus (AAV) vector systems have also been developed for polynucleotide delivery. AAV vectors can be readily constructed using techniques well known in the art. See, for example, U.S. Pat. Nos. 5,173,414 and 5,139,941; International PCT publication nos. WO 92/01070 and WO 93/03769; Lebkowski et al., *Molec Cell Biol,* 1988, 8: 3988-3996; Vincent et al., *Vaccines,* 1990, 90, Cold Spring Harbor Laboratory Press; Carter, B. J., *Current Opinion in Biotechnology,* 1992, 3: 533-539; Muzyczka, N., *Current Topics in Microbiol and Immunol,* 1992 158: 97-129; Kotin, R. M., *Human Gene Therapy,* 1994, 5: 793-801; Shelling and Smith, *Gene Therapy,* 1: 165-169; and Zhou et al., *J Exp Med,* 1994, 179: 1867-1875.

Additional viral vectors useful for delivering the antigen-encoding polynucleotide and the IL-25 inhibitor-encoding polynucleotide (which can be the same polynucleotide or two separate polynucleotides) by gene transfer include those derived from the pox family of viruses, such as vaccinia virus (e.g., Modified Vaccinia Ankara (MVA) virus) and avian poxvirus (e.g., Fowlpox virus). By way of example, vaccinia virus recombinants expressing the antigen-encoding polynucleotide and the IL-25 inhibitor-encoding polynucleotide can be constructed as follows. The polynucleotides are first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the expression products of interest into the viral genome. The resulting $TK^{(-)}$ recombinant can be selected by culturing the cells in the presence of 5-BrdU and picking viral plaques resistant thereto. In specific embodiments, a recombinant Fowlpox virus is prepared from which an antigen-encoding polynucleotide and an IL-4 antagonist-encoding polynucleotide are expressible for administration by a mucosal route (e.g., intranasally) and a recombinant MVA virus is prepared from which an antigen-encoding polynucleotide and an IL-4 antagonist-encoding polynucleotide are expressible for administration by a systemic route (e.g., intramuscularly). In illustrative examples of this type, the antigen encoded by the antigen-encoding polynucleotide may comprise an HIV antigen and/or a *M. tuberculosis* antigen.

Alternatively, avipoxviruses, such as the fowlpox and canarypox viruses, can also be used to deliver the coding sequences of interest. The use of an Avipox vector is particularly desirable in human and other mammalian species since members of the Avipox genus can only productively replicate in susceptible avian species and therefore are not infective in mammalian cells. Methods for producing recombinant Avipoxviruses are known in the art and employ genetic recombination, as described above with respect to the production of vaccinia viruses (see, e.g., International PCT publication nos. WO 91/12882; WO 89/03429; and WO 92/03545).

Any of a number of alphavirus vectors can also be used for delivery of polynucleotide compositions of the present invention, such as those vectors described in U.S. Pat. Nos. 5,843,723; 6,015,686; 6,008,035 and 6,015,694. Certain vectors based on Venezuelan Equine Encephalitis (VEE) can also be used, illustrative examples of which can be found in U.S. Pat. Nos. 5,505,947 and 5,643,576.

Moreover, molecular conjugate vectors, such as the adenovirus chimeric vectors described in Michael et al., *J. Biol. Chem.* 268:6866-69, 1993; and Wagner et al., *Proc. Natl. Acad. Sci. USA* 89:6099-6103, 1992, can also be used for gene delivery under the invention.

In other illustrative embodiments, lentiviral vectors are employed to deliver an antigen-encoding polynucleotide into selected cells or tissues. Typically, these vectors comprise a 5' lentiviral LTR, a tRNA binding site, a packaging signal, a promoter operably linked to one or more genes of interest, an origin of second strand DNA synthesis and a 3' lentiviral LTR, wherein the lentiviral vector contains a nuclear transport element. The nuclear transport element may be located either upstream (5') or downstream (3') of a coding sequence of interest (for example, a synthetic Gag or Env expression cassette of the present invention). A wide variety of lentiviruses may be utilized within the context of the present invention, including for example, lentiviruses selected from the group consisting of HIV, HIV-1, HIV-2, FIV, BIV, EIAV, MVV, CAEV, and SIV. Illustrative examples of lentiviral vectors are described in International PCT Publication Nos. WO 00/66759, WO 00/00600, WO 99/24465, WO 98/51810, WO 99/51754, WO 99/31251, WO 99/30742, and WO 99/15641. Desirably, a third generation SIN lentivirus is used. Commercial suppliers of third generation SIN (self-inactivating) lentiviruses include INVITROGEN (VIRAPOWER Lentiviral Expression System). Detailed methods for construction, transfection, harvesting, and use of lentiviral vectors are given, for example, in the Invitrogen technical manual "ViraPower Lentiviral Expression System Version B 050102 25-0501." Lentiviral vectors have emerged as an efficient method for gene transfer. Improvements in biosafety characteristics have made these vectors suitable for use at biosafety level 2 (BL2). A number of safety features are incorporated into third generation SIN (self-inactivating) vectors. Deletion of the viral 3' LTR U3 region results in a provirus that is unable to transcribe a full length viral RNA. In addition, a number of essential genes are provided in trans, yielding a viral stock that is capable of but a single round of infection and integration. Lentiviral vectors have several advantages, including: 1) pseudotyping of the vector using amphotropic envelope proteins allows them to infect virtually any cell type; 2) gene delivery to quiescent, post mitotic, differentiated cells, including neurones, has been demonstrated; 3) their low cellular toxicity is unique among transgene delivery systems; 4) viral integration into the genome permits long term transgene expression; 5) their packaging capacity (6-14 kb) is much larger than other retroviral, or adeno-associated viral vectors. In a recent demonstration of the capabilities of this system, lentiviral vectors expressing GFP were used to infect murine stem cells resulting in live progeny, germline transmission, and promoter-, and tissue-specific expression of the reporter (see, Ailles, L. E. and Naldini, L., *Lentiviral Vectors*, Springer-Verlag, Berlin, Heidelberg, New York, 2002, 31-52). An example of the current generation vectors is outlined in FIG. 2 of a review by Lois et al. (see, Lois, C., Hong, E. J., Pease, S., Brown, E. J., and Baltimore, D., *Science*, 2002, 295: 868-872).

In certain embodiments, a polynucleotide may be integrated into the genome of a target cell. This integration may be in the specific location and orientation via homologous recombination (gene replacement) or it may be integrated in a random, non-specific location (gene augmentation). In yet further embodiments, the polynucleotide may be stably maintained in the cell as a separate, episomal segment of DNA. Such polynucleotide segments or "episomes" encode sequences sufficient to permit maintenance and replication independent of or in synchronization with the host cell cycle. The manner in which the expression construct is delivered to a cell and where in the cell the polynucleotide remains is dependent on the type of expression construct employed.

In other embodiments, a polynucleotide is administered/delivered as "naked" DNA, for example as described in Ulmer et al., Science 259:1745-49, 1993 and reviewed by Cohen, *Science* 259:1691-92, 1993. The uptake of naked DNA may be increased by coating the DNA onto biodegradable beads, which are efficiently transported into the cells.

In still other embodiments, a composition of the present invention can be delivered via a particle bombardment approach, many of which have been described. In one illustrative example, gas-driven particle acceleration can be achieved with devices such as those manufactured by Powderject Pharmaceuticals PLC (Oxford, UK) and Powderject Vaccines Inc. (Madison, Wis.), some examples of which are described in U.S. Pat. Nos. 5,846,796; 6,010,478; 5,865,796; 5,584,807; and European patent no. 0500 799. This approach offers a needle-free delivery approach wherein a dry powder formulation of microscopic particles, such as polynucleotide or polypeptide particles, are accelerated to high speed within a helium gas jet generated by a hand-held device, propelling the particles into a target tissue of interest.

In a related embodiment, other devices and methods that may be useful for gas-driven needle-less injection of compositions of the present invention include those provided by Bioject, Inc. (Portland, Oreg.), some examples of which are described in U.S. Pat. Nos. 4,790,824; 5,064,413; 5,312,335; 5,383,851; 5,399,163; 5,520,639 and 5,993,412.

2.3.1 Immune Stimulating Cell Embodiments

The present invention also contemplates the use of cellular preparations comprising antigen-presenting cells, which present an antigen corresponding to at least a portion of the target antigen. Suitably, the antigen-presenting cells express or otherwise comprise the inhibitor of IL-25 function. Such antigen-presenting cells include professional or facultative antigen-presenting cells. Professional antigen-presenting cells function physiologically to present antigen in a form that is recognised by specific T cell receptors so as to stimulate or anergize a T lymphocyte or B lymphocyte mediated immune response. Professional antigen-presenting cells not only process and present antigens in the context of the major histocompatibility complex (MHC), but also possess the additional immuno-regulatory molecules required to complete T cell activation or induce a tolerogenic response. Professional antigen-presenting cells include, but are not limited to, macrophages, monocytes, B lymphocytes, cells of myeloid lineage, including monocytic-granulocytic-DC precursors, marginal zone Kupffer cells, microglia, T cells, Langerhans cells and dendritic cells including interdigitating dendritic cells and follicular dendritic cells. Non-professional or facultative antigen-presenting cells typically lack one or more of the immunoregulatory molecules required to complete T lymphocyte activation or anergy. Examples of non-professional or facultative antigen-presenting cells include, but are not limited to, activated T lymphocytes, eosinophils, keratinocytes, astrocytes, follicular cells, microglial cells, thymic cortical cells, endothelial cells, Schwann cells, retinal pigment epithelial cells, myoblasts, vascular smooth muscle cells, chondrocytes, enterocytes, thymocytes, kidney tubule cells and fibroblasts. In some embodiments, the antigen-presenting cell is selected from monocytes, macrophages, B lymphocytes, cells of myeloid lineage, dendritic cells or Langerhans cells. In certain advantageous embodiments, the antigen-presenting cell expresses CD11c and includes a dendritic cell or a Langerhans cell.

Cellular preparations for stimulating an immune response to an antigen or group of antigens may be prepared according to any suitable method known to the skilled practitioner. Illustrative methods for preparing antigen-presenting cells for stimulating antigen-specific immune responses are described by Albert et al. (International Publication WO 99/42564), Takamizawa et al. (1997, *J Immunol*, 158(5): 2134-2142), Thomas and Lipsky (1994, *J Immunol*, 153(9): 4016-4028), O'Doherty et al. (1994, *Immunology*, 82(3): 487-93), Fearnley et al. (1997, *Blood*, 89(10): 3708-3716), Weissman et al. (1995, *Proc Natl Acad Sci USA*, 92(3):826-830), Freudenthal and Steinman (1990, *Proc Natl Acad Sci USA*, 87(19):7698-7702), Romani et al. (1996, *J Immunol Methods*, 196(2): 137-151), Reddy et al. (1997, *Blood*, 90(9):3640-3646), Thurnher et al. (1997, *Exp Hematol*, 25(3):232-237), Caux et al. (1996, *J Exp Med*, 184(2):695-706; 1996, *Blood*, 87(6):2376-85), Luft et al. (1998, *Exp Hematol*, 26(6):489-500; 1998, *J Immunol*, 161(4):1947-1953), Cella et al. (1999, *J Exp Med*, 189(5): 821-829; 1997, *Nature*, 388(644):782-787; 1996, *J Exp Med*, 184(2):747-572), Ahonen et al. (1999, *Cell Immunol*, 197(1):62-72) and Piemonti et al. (1999, *J Immunol*, 162(11):6473-6481).

In some embodiments, antigen-presenting cells are isolated from a host, treated and then reintroduced or reinfused into the host. Conveniently, antigen-presenting cells can be obtained from the host to be treated either by surgical resection, biopsy, blood sampling, or other suitable technique. Such cells are referred to herein as "autologous" cells. In other embodiments, the antigen-presenting cells or cell lines are prepared and/or cultured from a different source than the host. Such cells are referred to herein as "allogeneic" cells. Desirably, allogeneic antigen-presenting cells or cell lines will share major and/or minor histocompatibility antigens to potential recipients (also referred to herein as 'generic' antigen-presenting cells or cell lines). In certain advantageous embodiments of this type, the generic antigen-presenting cells or cell lines comprise major histocompatibility (MHC) class I antigens compatible with a high percentage of the population (i.e., at least 10, 20, 30, 40, 50, 60, 70, 75, 80, 85, 90, 92, 94 or 98%) that is susceptible or predisposed to a particular condition. Suitably, the generic antigen-presenting cells or cell lines naturally express an immunostimulatory molecule as described herein, especially an immunostimulatory membrane molecule, at levels sufficient to trigger an immune response, desirably a T lymphocyte immune response (e.g., a cytotoxic T lymphocyte immune response), in the intended host. In certain embodiments, the antigen-presenting cells or cell lines are highly susceptible to treatment with at least one IFN as described in International PCT publication no. WO 01/88097 (i.e., implied high-level expression of class I HLA).

In some embodiments, antigen-presenting cells are made antigen-specific by a process including contacting or 'pulsing' the antigen-presenting cells with an antigen that corresponds to at least a portion of the target antigen for a time and under conditions sufficient to permit the antigen to be internalized by the antigen-presenting cells; and culturing the antigen-presenting cells so contacted for a time and under conditions sufficient for the antigen to be processed for presentation by the antigen-presenting cells. The pulsed cells can then be used to stimulate autologous or allogeneic T cells in vitro or in vivo. The amount of antigen to be placed in contact with antigen-presenting cells can be determined empirically by persons of skill in the art. Typically antigen-presenting cells are incubated with antigen for about 1 to 6 hours at 37° C. Usually, for purified antigens and peptides, 0.1-10 µg/mL is suitable for producing antigen-specific antigen-presenting cells. The antigen should be exposed to the antigen-presenting cells for a period of time sufficient for those cells to internalize the antigen. The time and dose of antigen necessary for the cells to internalize and present the processed antigen may be determined using pulse-chase protocols in which exposure to antigen is followed by a washout period and exposure to a read-out system e.g., antigen reactive T cells. Once the optimal time and dose necessary for cells to express processed antigen on their surface is determined, a protocol may be used to prepare cells and antigen for inducing tolerogenic responses. Those of skill in the art will recognize in this regard that the length of time necessary for an antigen-presenting cell to present an antigen may vary depending on the antigen or form of antigen employed, its dose, and the antigen-presenting cell employed, as well as the conditions under which antigen loading is undertaken. These parameters can be determined by the skilled artisan using routine procedures.

The delivery of exogenous antigen to an antigen-presenting cell can be enhanced by methods known to practitioners in the art. For example, several different strategies have been developed for delivery of exogenous antigen to the endogenous processing pathway of antigen-presenting cells, especially dendritic cells. These methods include insertion of antigen into pH-sensitive liposomes (Zhou and Huang, 1994, *Immunomethods*, 4:229-235), osmotic lysis of pinosomes after pinocytic uptake of soluble antigen (Moore et al., 1988, *Cell*, 54:777-785), coupling of antigens to potent adjuvants (Aichele et al., 1990, *J. Exp. Med.*, 171: 1815-1820; Gao et al., 1991, *J. Immunol.*, 147: 3268-3273; Schulz et al., 1991, *Proc. Natl. Acad. Sci. USA*, 88: 991-993; Kuzu et al., 1993, *Euro. J. Immunol.*, 23: 1397-1400; and Jondal et al., 1996, *Immunity* 5: 295-302) and apoptotic cell delivery of antigen (Albert et al. 1998, *Nature* 392:86-89; Albert et al. 1998, *Nature Med.* 4:1321-1324; and in International Publications WO 99/42564 and WO 01/85207). Recombinant bacteria (e.g., *E. coli*) or transfected host mammalian cells may be pulsed onto dendritic cells (as particulate antigen, or apoptotic bodies respectively) for antigen delivery. Recombinant chimeric virus-like particles (VLPs) have also been used as vehicles for delivery of exogenous heterologous antigen to the MHC class I processing pathway of a dendritic cell line (Bachmann et al., 1996, *Eur. J. Immunol.*, 26(11): 2595-2600).

Alternatively, or in addition, an antigen may be linked to, or otherwise associated with, a cytolysin to enhance the transfer of the antigen into the cytosol of an antigen-presenting cell of the invention for delivery to the MHC class I pathway. Exemplary cytolysins include saponin compounds such as saponin-containing Immune Stimulating Complexes (ISCOMs) (see e.g., Cox and Coulter, 1997, *Vaccine* 15(3): 248-256 and U.S. Pat. No. 6,352,697), phospholipases (see, e.g., Camilli et al., 1991, *J. Exp. Med.* 173: 751-754), pore-forming toxins (e.g., an α-toxin), natural cytolysins of gram-positive bacteria, such as listeriolysin O (LLO, e.g., Mengaud et al., 1988, *Infect. Immun.* 56: 766-772 and Portnoy et al., 1992, *Infect. Immun.* 60: 2710-2717), streptolysin O (SLO, e.g., Palmer et al., 1998, *Biochemistry* 37(8): 2378-2383) and perfringolysin O (PFO, e.g., Rossjohn et al., *Cell* 89(5): 685-692). Where the antigen-presenting cell is phagosomal, acid activated cytolysins may be advantageously used. For example, listeriolysin exhibits greater pore-forming ability at mildly acidic pH (the pH conditions within the phagosome), thereby facilitating delivery of vacuole (including phagosome and endosome) contents to the cytoplasm (see, e.g., Portnoy et al., *Infect. Immun.* 1992, 60: 2710-2717).

The cytolysin may be provided together with a pre-selected antigen in the form of a single composition or may be provided as a separate composition, for contacting the antigen-presenting cells. In one embodiment, the cytolysin is fused or otherwise linked to the antigen, wherein the fusion or linkage permits the delivery of the antigen to the cytosol of the target cell. In another embodiment, the cytolysin and antigen are provided in the form of a delivery vehicle such as, but not limited to, a liposome or a microbial delivery vehicle selected from virus, bacterium, or yeast. Suitably, when the delivery vehicle is a microbial delivery vehicle, the delivery vehicle is non-virulent. In a preferred embodiment of this type, the delivery vehicle is a non-virulent bacterium, as for example described by Portnoy et al. in U.S. Pat. No. 6,287,556, comprising a first polynucleotide encoding a non-secreted functional cytolysin operably linked to a regulatory polynucleotide which expresses the cytolysin in the bacterium, and a second polynucleotide encoding one or more pre-selected antigens. Non-secreted cytolysins may be provided by various mechanisms, e.g., absence of a functional signal sequence, a secretion incompetent microbe, such as microbes having genetic lesions (e.g., a functional signal sequence mutation), or poisoned microbes, etc. A wide variety of nonvirulent, non-pathogenic bacteria may be used; preferred microbes are relatively well characterized strains, particularly laboratory strains of *E. coli*, such as MC4100, MC1061, DH5a, etc. Other bacteria that can be engineered for the invention include well-characterized, nonvirulent, non-pathogenic strains of *Listeria monocytogenes*, *Shigella flexneri*, mycobacterium, *Salmonella*, *Bacillus subtilis*, etc. In particular embodiments, the bacteria are attenuated to be non-replicative, non-integrative into the host cell genome, and/or non-motile inter- or intra-cellularly.

The delivery vehicles described above can be used to deliver one or more antigens to virtually any antigen-presenting cell capable of endocytosis of the subject vehicle, including phagocytic and non-phagocytic antigen-presenting cells. In embodiments when the delivery vehicle is a microbe, the subject methods generally require microbial uptake by the target cell and subsequent lysis within the antigen-presenting cell vacuole (including phagosomes and endosomes).

In some other embodiments, in order to enhance the class I presentation of the antigen, the immune stimulator is modified to comprise an intracellular degradation signal or degron. The degron is suitably a ubiquitin-mediated degradation signal selected from a destabilizing amino acid at the amino-terminus of an antigen, a ubiquitin acceptor, a ubiquitin or combination thereof.

Thus, in one embodiment, the immune stimulator is modified to include a destabilizing amino acid at its amino-terminus so that the protein so modified is subject to the N-end rule pathway as disclosed, for example, by Bachmair et al., in U.S. Pat. No. 5,093,242 and by Varshaysky et al., in U.S. Pat. No. 5,122,463. In a preferred embodiment of this type, the destabilizing amino acid is selected from isoleucine and glutamic acid, more preferably from histidine tyrosine and glutamine, and even more preferably from aspartic acid, asparagine, phenylalanine, leucine, tryptophan and lysine. In an especially preferred embodiment, the destabilizing amino acid is arginine.

Modification or design of the amino-terminus of a protein can also be accomplished at the genetic level. Conventional techniques of site-directed mutagenesis for addition or substitution of appropriate codons to the 5' end of an isolated or synthesized antigen-encoding polynucleotide can be employed to provide a desired amino-terminal structure for the encoded protein. For example, so that the protein expressed has the desired amino acid at its amino-terminus the appropriate codon for a destabilizing amino acid can be inserted or built into the amino-terminus of the protein-encoding sequence. Where necessary, a nucleic acid sequence encoding the amino-terminal region of a protein can be modified to introduce one or more lysine residues in an appropriate context, which act as a ubiquitin acceptor as described in more detail below. This can be achieved most conveniently by employing DNA constructs encoding "universal destabilizing segments". A universal destabilizing segment comprises a nucleic acid construct which encodes a polypeptide structure, preferably segmentally mobile, containing one or more lysine residues, the codons for lysine residues being positioned within the construct such that when the construct is inserted into the coding sequence of the antigen-encoding polynucleotide, the lysine residues are sufficiently spatially proximate to the amino-terminus of the encoded protein to serve as the second determinant of the complete amino-terminal degradation signal. The insertion of such constructs into the 5' portion of an antigen-encoding polynucleotide would provide the encoded protein with a lysine residue (or residues) in an appropriate context for destabilization.

The codon for the amino-terminal amino acid of the protein of interest can be made to encode the desired amino acid by, for example, site-directed mutagenesis techniques currently standard in the field. Suitable mutagenesis methods are described for example in the relevant sections of Ausubel, et al. (supra) and of Sambrook, et al., (supra). Alternatively, suitable methods for altering DNA are set forth, for example, in U.S. Pat. Nos. 4,184,917, 4,321,365 and 4,351,901, which are incorporated herein by reference. Instead of in vitro mutagenesis, the synthetic polynucleotide can be synthesized de novo using readily available machinery. Sequential synthesis of DNA is described, for example, in U.S. Pat. No. 4,293,652. However, it should be noted that the present invention is not dependent on, and not directed to, any one particular technique for constructing a polynucleotide encoding a modified antigen as described herein.

If the antigen-encoding polynucleotide is a synthetic or recombinant polynucleotide the appropriate 5' codon can be built-in during the synthetic process. Alternatively, nucleotides for a specific codon can be added to the 5' end of an isolated or synthesized polynucleotide by ligation of an appropriate nucleic acid sequence to the 5' (amino-terminus-encoding) end of the polynucleotide. Nucleic acid inserts encoding appropriately located lysine residues (such as the "universal destabilizing segments" described above) can suitably be inserted into the 5' region to provide for the second determinant of the complete amino-terminal degradation.

In a preferred embodiment, the modified antigen, which comprises a destabilizing amino acid at its amino terminus, is fused or otherwise conjugated to a masking entity, which masks said amino terminus so that when unmasked the antigen will exhibit the desired rate of intracellular proteolytic degradation. Suitably, the masking entity is a masking protein sequence. The fusion protein is designed so that the masking protein sequence fused to the amino-terminus of the protein of interest is susceptible to specific cleavage at the junction between the two. Removal of the protein sequence thus unmasks the amino-terminus of the protein of interest and the half-life of the released protein is thus governed by the predesigned amino-terminus. The fusion protein can be designed for specific cleavage in vivo, for example, by a host cell endoprotease or for specific cleavage in an in vitro system where it can be cleaved after isolation from a producer cell (which lacks the capability to cleave the fusion protein). Thus, in a preferred embodiment, the masking protein sequence is cleavable by an endoprotease, which is preferably an endogenous endoprotease of a mammalian cell. Suitable endoproteases include, but are not restricted to, serine endoproteases (e.g., subtilisins and furins) as described, for example, by Creemers, et al. (1998, *Semin. Cell Dev. Biol.* 9 (1): 3-10), proteasomal endopeptidases as described, for example, by Zwickl, et al. (2000, *Curr. Opin. Struct. Biol.* 10 (2): 242-250), proteases relating to the MHC class I processing pathway as described, for example, by Stolze et al. (2000, *Nat. Immunol.* 1 413-418) and signal peptidases as described, for example, by Dalbey, et al. (1997, *Protein Sci.* 6 (6): 1129-1138). In a preferred embodiment of this type, the masking protein sequence comprises a signal peptide sequence. Suitable signal peptides sequences are described, for example, by Nothwehr et al. (1990, *Bioessays* 12 (10): 479-484), Izard, et al. (1994, *Mol. Microbiol.* 13 (5): 765-773), Menne, et al. (2000, *Bioinformatics.* 16 (8): 741-742) and Ladunga (2000, *Curr. Opin. Biotechnol.* 11 (1): 13-18). Suitably, an endoprotease cleavage site is interposed between the masking protein sequence and the antigen.

A modified antigen with an attached masking sequence may be conveniently prepared by fusing a nucleic acid sequence encoding a masking protein sequence upstream of another nucleic acid sequence encoding an antigen, which corresponds to the target antigen of interest and which includes a destabilizing amino acid at its amino-terminus. The codon for the amino-terminal amino acid of the antigen of interest is suitably located immediately adjacent to the 3' end of the masking protein-encoding nucleic acid sequence.

In another embodiment, the antigen is modified to include, or is otherwise associated with, a ubiquitin acceptor which is a molecule that preferably contains at least one residue appropriately positioned from the N-terminal of the antigen as to be able to be bound by ubiquitin molecules. Such residues preferentially have an epsilon amino group such as lysine. Physical analysis demonstrates that multiple lysine residues function as ubiquitin acceptor sites (King et al., 1996, *Mol. Biol. Cell* 7: 1343-1357; King et al., 1996, Science 274: 1652-1659). Examples of other ubiquitin acceptors include lacI or Sindis virus RNA polymerase. Ubiquitination at the N-terminal of the protein specifically targets the protein for degradation via the ubiquitin-proteosome pathway.

Other protein processing signals that destabilize an antigen of interest and allow for enhanced intracellular degradation are contemplated in the present invention. These other methods may not necessarily be mediated by the ubiquitin pathway, but may otherwise permit degradation of proteins in the cytoplasm via proteasomes. For example, the present invention contemplates the use of other intracellular processing signals which govern the rate(s) of intracellular protein degradation including, but not limited to, those described by Bohley et al. (1996, *Biol. Chem. Hoppe. Seyler* 377: 425-435). Such processing signals include those that allow for phosphorylation of the target protein (Yaglom et al., 1996, *Mol. Cell Biol.* 16: 3679-3684; Yaglom et al., 1995, *Mol. Cell Biol.* 15: 731-741). Also contemplated by the present invention are modification of an parent antigen that allow for post-translational arginylation (Ferber et al. 1987, *Nature* 326: 808-811; Bohley et al., 1991, *Biomed. Biochim. Acta* 50: 343-346) of the protein which can enhance its rate(s) of intracellular degradation. The present invention also contemplates the use of certain structural features of proteins that can influence higher rates of intracellular protein turn-over, including protein surface hydrophobicity, clusters of hydrophobic residues within the protein (Sadis et al., *Mol Cell Biol,* 1995, 15: 4086-4094), certain hydrophobic pentapeptide motifs at the protein's carboxy-terminus (C-terminus) (e.g., ARINV (SEQ ID NO: 111)), as found on the C-terminus of ornithine decarboxylase (Ghoda et al., *Mol Cell Biol,* 1992, 12: 2178-2185; Li, et al., *Mol Cell Biol,* 1994, 14: 87-92), or AANDENYALAA (SEQ ID NO: 112), as found in C-terminal tags of aberrant polypeptides (Keiler et al., *Science,* 1996, 271: 990-993,) or PEST regions (regions rich in proline (P), glutamic acid (E), serine (S), and threonine (T), which are optionally flanked by amino acids comprising electropositive side chains (Rogers et al., *Science,* 1986, 234 (4774): 364-368; 1988, *J. Biol. Chem.* 263: 19833-19842). Moreover, certain motifs have been identified in proteins that appear necessary and possibly sufficient for achieving rapid intracellular degradation. Such motifs include RXALGXIXN region (SEQ ID NO: 113) (where X=any amino acid) in cyclins (Glotzer et al., *Nature,* 1991, 349: 132-138) and the KTKRNYSARD motif (SEQ ID NO: 114) in isocitrate lyase (Ordiz et al., *FEBS Lett,* 1996, 385: 43-46).

The present invention also contemplates enhanced cellular degradation of a parent antigen which may occur by the incorporation into that antigen of known protease cleavage sites. For example, amyloid beta-protein can be cleaved by beta- and gamma-secretase (Iizuka et al., 1996, *Biochem. Biophys. Res. Commun.* 218: 238-242) and the two-chain vitamin K-dependent coagulation factor X can be cleaved by calcium-dependent endoprotease(s) in liver (Wallin et al., 1994, *Thromb. Res.* 73: 395-403).

In yet another embodiment, the parent antigen is conjugated to a ubiquitin or a biologically active fragment thereof, to produce a modified antigen whose rate of intracellular proteolytic degradation is increased, enhanced or otherwise elevated relative to the parent antigen. In a preferred embodiment of this type, the ubiquitin or biologically active fragment is fused, or otherwise conjugated, to the antigen. Suitably, the ubiquitin is of mammalian origin, more preferably of human or other primate origin.

In one embodiment, the ubiquitin-antigen fusion protein is suitably produced by covalently attaching an antigen corresponding to the target antigen to a ubiquitin or a biologically active fragment thereof. Covalent attachment may be effected by any suitable means known to persons of skill in the art. For example, protein conjugates may be prepared by linking proteins together using bifunctional reagents. The bifunctional reagents can be homobifunctional or heterobifunctional.

Homobifunctional reagents are molecules with at least two identical functional groups. The functional groups of the reagent generally react with one of the functional groups on a protein, typically an amino group. Examples of homobifunctional reagents include glutaraldehyde and diimidates. An example of the use of glutaraldehyde as a cross-linking agent is described by Poznansky et al. (1984, *Science,* 223: 1304-1306). The use of diimidates as a cross-linking agent is described for example by Wang, et al. (1977, *Biochemistry,* 16: 2937-2941). Although it is possible to use homobifunctional reagents for the purpose of forming a modified antigen according to the invention, skilled practitioners in the art will appreciate that it is difficult to attach different proteins in an ordered fashion with these reagents. In this regard, in attempting to link a first protein with a second protein by means of a homobifunctional reagent, one cannot prevent the linking of the first protein to each other and of the second to each other. Heterobifunctional crosslinking reagents are, therefore, preferred because one can control the sequence of reactions, and combine proteins at will. Heterobifunctional reagents thus provide a more sophisticated method for linking two proteins. These reagents require one of the molecules to be joined, hereafter called Partner B, to possess a reactive group not found on the other, hereafter called Partner A, or else require that one of the two functional groups be blocked or otherwise greatly reduced in reactivity while the other group is reacted with Partner A. In a typical two-step process for forming heteroconjugates, Partner A is reacted with the heterobifunctional reagent to form a derivatized Partner A molecule. If the unreacted functional group of the cross linker is blocked, it is then deprotected. After deprotection, Partner B is coupled to derivatized Partner A to form the conjugate. Primary amino groups on Partner A are reacted with an activated carboxylate or imidate group on the cross linker in the derivatization step. A reactive thiol or a blocked and activated thiol at the other end of the cross linker is reacted with an electrophilic group or with a reactive thiol, respectively, on Partner B. When the cross linker possesses a reactive thiol, the electrophile on Partner B preferably will be a blocked and activated thiol, a maleimide, or a halomethylene carbonyl (e.g., bromoacetyl or iodoacetyl) group. Because biological macromolecules do not naturally contain such electrophiles, they must be added to Partner B by a separate derivatization reaction. When the cross linker possesses a blocked and activated thiol, the thiol on Partner B with which it reacts may be native to Partner B.

An example of a heterobifunctional reagent is N-succinimidyl 3-(2-pyridyldithio) propionate (SPDP) (see for example Carlsson et al., 1978, *Biochem. J.,* 173: 723-737). Other heterobifunctional reagents for linking proteins include for example succinimidyl 4-(N-maleimidomethyl) cyclohexane-1-carboxylate (SMCC) (Yoshitake et al., 1979, *Eur. J. Biochem,* 101: 395-399), 2-iminothiolane (IT) (Jue et al., 1978, *Biochemistry,* 17: 5399-5406), and S-acetyl mercaptosuccinic anhydride (SAMSA) (Klotz and Heiney, 1962, *Arch. Biochem. Biophys.,* 96: 605-612). All three react preferentially with primary amines (e.g., lysine side chains) to form an amide or amidine group which links a thiol to the derivatized molecule (e.g., a heterologous antigen) via a connecting short spacer arm, one to three carbon atoms long. Examples of heterobifunctional reagents comprising reactive groups having a double bond that reacts with a thiol group include SMCC mentioned above, succinimidyl m-maleimidobenzoate, succinimidyl 3-(maleimido)propionate, sulfosuccinimidyl 4-(p-maleimidophenyl)butyrate, sulfosuccinimidyl 4-(N-maleimidomethylcyclohexane-1-carboxylate and maleimidobenzoyl-N-hydroxysuccinimide ester (MBS). In a preferred embodiment, MBS is used to produce the conjugate. Other heterobifunctional reagents for forming conjugates of two proteins are described for example by Rodwell et al. in U.S. Pat. No. 4,671,958 and by Moreland et al. in U.S. Pat. No. 5,241,078.

In an alternate embodiment, a ubiquitin-antigen fusion protein is suitably expressed by a synthetic chimeric polynucleotide comprising a first nucleic acid sequence, which encodes an antigen corresponding to the target antigen, and which is linked downstream of, and in reading frame with, a second nucleic acid sequence encoding a ubiquitin or biologically active fragment thereof. In a preferred embodiment of this type, the second polynucleotide comprises a first nucleic acid sequence, which encodes an antigen corresponding to the target antigen, and which is linked immediately adjacent to, downstream of, and in reading frame with, a second nucleic acid sequence encoding a ubiquitin or biologically active fragment thereof. In another embodiment, the second polynucleotide comprises a first nucleic acid sequence, which encodes an antigen corresponding to the target antigen, and which is linked upstream of, and in reading frame with, a second nucleic acid sequence encoding a ubiquitin or biologically active fragment thereof. In yet another embodiment of this type, the second polynucleotide comprises a first nucleic acid sequence, which encodes an antigen corresponding to the target antigen, and which is linked immediately adjacent to, upstream of, and in reading frame with, a second nucleic acid sequence encoding a ubiquitin or biologically active fragment thereof.

In other embodiments, the antigen is produced inside the antigen-presenting cell by introduction of a suitable expression vector as for example described above. The antigen-encoding portion of the expression vector may comprise a naturally-occurring sequence or a variant thereof, which has been engineered using recombinant techniques. In one example of a variant, the codon composition of an antigen-encoding polynucleotide is modified to permit enhanced expression of the antigen in a target cell or tissue of choice using methods as set forth in detail in International Publications WO 99/02694 and WO 00/42215. Briefly, these methods are based on the observation that translational efficiencies of different codons vary between different cells or tissues and that these differences can be exploited, together with codon composition of a gene, to regulate expression of a protein in a particular cell or tissue type. Thus, for the construction of codon-optimized polynucleotides, at least one existing codon of a parent polynucleotide is replaced with a synonymous codon that has a higher translational efficiency in a target cell or tissue than the existing codon it replaces. Although it is preferable to replace all the existing codons of a parent nucleic acid molecule with synonymous codons which have that higher translational efficiency, this is not necessary because increased expression can be accomplished even with partial replacement. Suitably, the replacement step affects 5, 10, 15, 20, 25, 30%, more preferably 35, 40, 50, 60, 70% or more of the existing codons of a parent polynucleotide.

The expression vector for introduction into the antigen-presenting cell will be compatible therewith such that the antigen-encoding polynucleotide is expressible by the cell. For example, expression vectors of this type can be derived from viral DNA sequences including, but not limited to, adenovirus, adeno-associated viruses, herpes-simplex viruses and retroviruses such as B, C, and D retroviruses as well as spumaviruses and modified lentiviruses. Suitable expression vectors for transfection of animal cells are described, for example, by Wu and Ataai (*Curr Opin Biotechnol,* 2000, 11(2): 205-208), Vigna and Naldini (*J Gene Med,* 2000, 2(5): 308-316), Kay, et al. (*Nat Med,* 2001, 7(1): 33-40), Athanasopoulos, et al. (*Int J Mol Med,* 2000, 6(4): 363-375) and Walther and Stein (*Drugs,* 2000, 60(2): 249-271). The expression vector is introduced into the antigen-presenting cell by any suitable means which will be dependent on the particular choice of expression vector and antigen-presenting cell employed. Such means of introduction are well-known to those skilled in the art. For example, introduction can be effected by use of contacting (e.g., in the case of viral vectors), electroporation, transformation, transduction, conjugation or triparental mating, transfection, infection membrane fusion with cationic lipids, high-velocity bombardment with DNA-coated microprojectiles, incubation with calcium phosphate-DNA precipitate, direct microinjection into single cells, and the like. Other methods also are available and are known to those skilled in the art. Alternatively, the vectors are introduced by means of cationic lipids, e.g., liposomes. Such liposomes are commercially available (e.g., LIPOFECTIN®, LIPOFECTAMINE™, and the like, supplied by Life Technologies, Gibco BRL, Gaithersburg, Md.). It will be understood by persons of skill in the art that the techniques for assembling and expressing antigen-encoding nucleic acid molecules, and/or immune stimulator encoding nucleic acid molecules as described herein e.g., synthesis of oligonucleotides, nucleic acid amplification techniques, transforming cells, constructing vectors, expressions system and the like and transducing or otherwise introducing nucleic acid molecules into cells are well established in the art, and most practitioners are familiar with the standard resource materials for specific conditions and procedures.

In some embodiments, the antigen-specific antigen-presenting cells are obtained by isolating antigen-presenting cells or their precursors from a cell population or tissue to which modification of an immune response is desired. Typically, some of the isolated antigen-presenting cells or precursors will constitutively present antigens or have taken up such antigen in vivo that are targets or potential targets of an immune response for which stimulation or inhibition of an immune response is desired. In this instance, the delivery of exogenous antigen is not essential. Alternatively, cells may be derived from biopsies of healthy or diseased tissues, lysed or rendered apoptotic and the pulsed onto antigen-presenting cells (e.g., dendritic cells). In certain embodiments of this type, the antigen-presenting cells represent cancer or tumor cells to which an antigen-specific immune response is required. Illustrative examples of cancers or tumor cells include cells of sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; myelomonocytic, monocytic and erythroleukemia); chronic leukemia (chronic myelocytic (granulocyte) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In certain embodiments, the cancer or tumor cells are selected from the group consisting of melanoma cells and mammary carcinoma cells.

In some of the above embodiments, the cancer or tumor cells will constitute facultative or non-professional antigen-presenting cells, and may in some instances require further modification to enhance their antigen-presenting functions. In these instances, the antigen-presenting cells are further modified to express one or more immunoregulatory molecules, which include any molecules occurring naturally in animals that may regulate or directly influence immune responses including: proteins involved in antigen processing and presentation such as TAP1/TAP2 transporter proteins, proteosome molecules such as LMP2 and LMP7, heat shock proteins such as gp96, HSP70 and HSP90, and major histocompatibility complex (MHC) or human leukocyte antigen (HLA) molecules; factors that provide co-stimulation signals for T cell activation such as B7 and CD40; factors that provide co-inhibitory signals for direct killing of T cells or induction of T lymphocyte or B lymphocyte anergy or stimulation of T regulatory cell (Treg) generation such as OX-2, programmed death-1 ligand (PD-1L); accessory molecules such as CD83; chemokines; lymphokines and cytokines such as IFN s α, β and γ, interleukins (e.g., IL-2, IL-7, IL-12, IL-15, IL-22, etc.), factors stimulating cell growth (e.g., GM-SCF) and other factors (e.g., tumor necrosis factors (TNFs), DC-SIGN, MIP1α, MIP1β and transforming growth factor-β (TGF-β). In certain advantageous embodiments, the immunoregulatory molecules are selected from a B7 molecule (e.g., B7-1, B7-2 or B7-3) and an ICAM molecule (e.g., ICAM-1 and ICAM-2).

Instead of recombinantly expressing immunoregulatory molecules, antigen-presenting cells expressing the desired immunostimulatory molecule(s) may be isolated or selected from a heterogeneous population of cells. Any method of isolation/selection is contemplated by the present invention, examples of which are known to those of skill in the art. For instance, one can take advantage of one or more particular characteristics of a cell to specifically isolate that cell from a heterogeneous population. Such characteristics include, but are not limited to, anatomical location of a cell, cell density, cell size, cell morphology, cellular metabolic activity, cell uptake of ions such as $Ca^{2+}$, $K^+$, and $H^+$ ions, cell uptake of compounds such as stains, markers expressed on the cell surface, protein fluorescence, and membrane potential. Suitable methods that can be used in this regard include surgical removal of tissue, flow cytometry techniques such as fluorescence-activated cell sorting (FACS), immunoaf-finity separation (e.g., magnetic bead separation such as DYNABEAD™ separation), density separation (e.g., metrizamide, PERCOLL™, or FICOLL™ gradient centrifugation), and cell-type specific density separation. Desirably, the cells are isolated by flow cytometry or by immunoaffinity separation using an antigen-binding molecule that is immuno-interactive with the immunoregulatory molecule.

Alternatively, the immunoregulatory molecule can be provided to the antigen-presenting cells in soluble form. In some embodiments of this type, the immunoregulatory molecule is a B7 molecule that lacks a functional transmembrane domain (e.g., that comprises a B7 extracellular domain), non-limiting examples of which are described by McHugh et al. (*Clin Immunol Immunopathol*, 1998, 87(1): 50-59), Faas et al. (*J Immunol*, 2000, 164(12): 6340-6348) and Jeannin et al. (*Immunity*, 2000, 13(3): 303-312). In other embodiments of this type, the immunostimulatory protein is a B7 derivative including, but not limited to, a chimeric or fusion protein comprising a B7 molecule, or biologically active fragment thereof, or variant or derivative of these, linked together with an antigen-binding molecule such as an immunoglobulin molecule or biologically active fragment thereof. For example, a polynucleotide encoding the amino acid sequence corresponding to the extracellular domain of the B7-1 molecule, containing amino acids from about position 1 to about position 215, is joined to a polynucleotide encoding the amino acid sequences corresponding to the hinge, CH2 and CH3 regions of human Ig Cγ1, using PCR, to form a polynucleotide that is expressed as a B7Ig fusion protein. DNA encoding the amino acid sequence corresponding to a B7Ig fusion protein has been deposited with the American Type culture Collection (ATCC) in Rockville, Md., under the Budapest Treaty on May 31, 1991 and accorded accession number 68627. Techniques for making and assembling such B7 derivatives are disclosed for example by Linsley et al. (U.S. Pat. No. 5,580,756). Reference also may be made to Sturmhoefel et al. (*Cancer Res*, 1999, 59: 4964-4972) who disclose fusion proteins comprising the extracellular region of B7-1 or B7-2 fused in frame to the Fc portion of IgG2a.

The half-life of a soluble immunoregulatory molecule may be prolonged by any suitable procedure if desired. Preferably, such molecules are chemically modified with polyethylene glycol (PEG), including monomethoxy-polyethylene glycol, as for example disclosed by Chapman et al. (*Nature Biotechnology*, 1999, 17: 780-783).

Alternatively, or in addition, the antigen-presenting cells are cultured in the presence of at least one IFN for a time and under conditions sufficient to enhance the antigen presenting function of the cells and washing the cells to remove the IFN(s). In certain advantageous embodiments of this type, the step of culturing may comprise contacting the cells with at least one type I IFN and/or a type II IFN. The at least one type I IFN is suitably selected from the group consisting of an IFN-α, an IFN-β, a biologically active fragment of an IFN-α, a biologically active fragment of an IFN-β, a variant of an IFN-α, a variant of an IFN-β, a variant of a said biologically active fragment, a derivative of an IFN-α, a derivative of an IFN-β, a derivative of a said biologically active fragment, a derivative of a said variant, an analogue of IFN-α and an analogue of IFN-β. Typically, the type II IFN is selected from the group consisting of an IFN-γ, a biologically active fragment of an IFN-γ, a variant of an IFN-γ, a variant of said biologically active fragment, a derivative of an IFN-γ, a derivative of said biologically active fragment, a derivative of said variant and an analogue of an IFN-γ. Exemplary methods and conditions for enhancing the antigen-presenting functions of antigen-presenting cells using IFN treatment are described in International PCT publication no. WO 2001/88097.

In some embodiments, the antigen-presenting cells (e.g., cancer cells) or cell lines are suitably rendered inactive to prevent further proliferation once administered to the subject. Any physical, chemical, or biological means of inactivation may be used, including but not limited to irradiation (generally with at least about 5,000 cGy, usually at least about 10,000 cGy, typically at least about 20,000 cGy); or treatment with mitomycin-C (usually at least 10 µg/mL; more usually at least about 50 µg/mL).

The antigen-presenting cells may be obtained or prepared to contain and/or express one or more antigens by any number of means, such that the antigen(s) or processed form(s) thereof, is (are) presented by those cells for potential modulation of other immune cells, including T lymphocytes and B lymphocytes, and particularly for producing T lymphocytes and B lymphocytes that are primed to respond to a specified antigen or group of antigens.

The present invention also contemplates co-introducing an agent that comprises an inhibitor of IL-13 function, and/or an inhibitor of IL-4 function into an antigen-presenting cell or antigen-presenting cell precursor so that the antigen-present cell co-expresses or co-presents both the antigen and the inhibitor of IL-13 function and/or the inhibitor of IL-4 function.

The agents of the present invention may be encapsulated, adsorbed to, or associated with, particulate carriers. Such carriers can be used to selectively introduce the agents to cells of the immune system. The particles can be taken up by professional antigen presenting cells such as macrophages and dendritic cells, and/or can enhance antigen presentation through other mechanisms such as stimulation of cytokine release. Examples of particulate carriers include those derived from polymethyl methacrylate polymers, as well as microparticles derived from poly(lactides) and poly(lactide-co-glycolides), known as PLG. See, e.g., Jeffery et al., 1993, Pharm. Res. 10:362-368; McGee J. P., et al., 1997, J Microencapsul. 14(2):197-210; O'Hagan D. T., et al., 1993, Vaccine 11(2):149-54.

Furthermore, other particulate systems and polymers can be used for the in vivo delivery of the agents of the present invention. For example, polymers such as polylysine, polyarginine, polyornithine, spermine, spermidine, as well as conjugates of these molecules, are useful for transferring a nucleic acid of interest. Similarly, DEAE dextran-mediated transfection, calcium phosphate precipitation or precipitation using other insoluble inorganic salts, such as strontium phosphate, aluminum silicates including bentonite and kaolin, chromic oxide, magnesium silicate, talc, and the like, will find use with the present methods. See, e.g., Feigner, P. L., Advanced Drug Delivery Reviews (1990) 5:163-187, for a review of delivery systems useful for gene transfer. Peptoids (Zuckerman, R. N., et al., U.S. Pat. No. 5,831,005, issued Nov. 3, 1998) may also be used for delivery of a nucleic acid construct of the present invention.

Additionally, biolistic delivery systems employing particulate carriers such as gold and tungsten, are especially useful for delivering agents that are in nucleic acid form (e.g., nucleic acid constructs of the present invention). The particles are coated with the synthetic expression cassette(s) to be delivered and accelerated to high velocity, generally under a reduced atmosphere, using a gun powder discharge from a "gene gun." For a description of such techniques, and apparatuses useful therefor, see, e.g., U.S. Pat. Nos. 4,945,050; 5,036,006; 5,100,792; 5,179,022; 5,371,015; and 5,478,744. In illustrative examples, gas-driven particle acceleration can be achieved with devices such as those manufactured by PowderMed Pharmaceuticals PLC (Oxford, UK) and PowderMed Vaccines Inc. (Madison, Wis.), some examples of which are described in U.S. Pat. Nos. 5,846,796; 6,010,478; 5,865,796; 5,584,807; and EP Patent No. 0500 799. This approach offers a needle-free delivery approach wherein a dry powder formulation of microscopic particles, such as polynucleotide or polypeptide particles, are accelerated to high speed within a helium gas jet generated by a hand-held device, propelling the particles into a target tissue of interest. Other devices and methods that may be useful for gas-driven needle-less injection of compositions of the present invention include those provided by Bioject, Inc. (Portland, Oreg.), some examples of which are described in U.S. Pat. Nos. 4,790,824; 5,064,413; 5,312,335; 5,383,851; 5,399,163; 5,520,639 and 5,993,412.

Alternatively, micro-cannula- and microneedle-based devices (such as those being developed by Becton Dickinson and others) can be used to administer nucleic acid constructs of the invention. Illustrative devices of this type are described in EP 1 092 444 A1, and U.S. application Ser. No. 606,909, filed Jun. 29, 2000. Standard steel cannula can also be used for intra-dermal delivery using devices and methods as described in U.S. Ser. No. 417,671, filed Oct. 14, 1999. These methods and devices include the delivery of substances through narrow gauge (about 30 G) "micro-cannula" with limited depth of penetration, as defined by the total length of the cannula or the total length of the cannula that is exposed beyond a depth-limiting feature. It is within the scope of the present invention that targeted delivery of substances including nucleic acid constructs can be achieved either through a single microcannula or an array of microcannula (or "microneedles"), for example 3-6 microneedles mounted on an injection device that may include or be attached to a reservoir in which the substance to be administered is contained.

2.4 Ancillary Components

In some embodiments the composition further comprises one or more cytokines, which are suitably selected from flt3, SCF, IL-3, IL-6, GM-CSF, G-CSF, TNF-α, TNF-β, LT-β, IL-2, IL-7, IL-9, IL-15, IL-5, IL-1α, IL-1β, IFN-γ, IL-17, IL-16, IL-18, HGF, IL-11, MSP, FasL, TRAIL, TRANCE, LIGHT, TWEAK, CD27L, CD30L, CD40L, APRIL, TALL-1, 4-1BBL, OX40L, GITRL, IGF-I, IGF-II, HGF, MSP, FGF-a, FGF-b, FGF-3-19, NGF, BDNF, NTs, Tpo, Epo, Ang1-4, PDGF-AA, PDGF-BB, VEGF-A, VEGF-B, VEGF-C, VEGF-D, PIGF, EGF, TGF-α, AR, BTC, HRGs, HB-EGF, SMDF, OB, CT-1, CNTF, OSM, SCF, Flt-3L, M-CSF, MK and PTN or their functional, recombinant or chemical equivalents or homologues thereof. Preferably the cytokine is selected from the group consisting of IL-12, IL-3, IL-5, TNF, GMCSF, and IFN-γ.

3. Cell Based Therapy or Prophylaxis

In accordance with the present invention, an inhibitor of IL-25 function, as described for example in Section 2.1, can be administered to a patient, together with antigen-presenting cells as described in Section 2.3.2 for priming or boosting an immune response. These cell based compositions are useful, therefore, for treating or preventing a disease or condition that is associated with the presence or aberrant expression of a target antigen. The cells of the invention can be introduced into a patient by any means (e.g., injection), which produces the desired immune response to an antigen or group of antigens. The cells may be derived from the patient (i.e., autologous cells) or from an individual or individuals who are MHC matched or mismatched (i.e., allogeneic) with the patient. Typically, autologous cells are injected back into the patient from whom the source cells were obtained. The injection site may be mucosal, subcutaneous, intraperitoneal, intramuscular, intradermal, or intravenous. The cells may be administered to a patient to provide protective immunity or to a patient already suffering from a disease or condition or who is predisposed to a disease or condition in sufficient number to treat or prevent or alleviate the symptoms of the disease or condition. The number of cells injected into the patient in need of the treatment or prophylaxis may vary depending on inter alia, the antigen or antigens and size of the individual. This number may range for example between about $10^3$ and $10^{11}$, and usually between about $10^5$ and $10^7$ cells (e.g., dendritic cells or T lymphocytes). Single or multiple administrations of the cells can be carried out with cell numbers and pattern being selected by the treating physician. The cells should be administered in a pharmaceutically acceptable carrier, which is non-toxic to the cells and the individual. Such carrier may be the growth medium in which the cells were grown, or any suitable buffering medium such as phosphate buffered saline. The cells may be administered alone or as an adjunct therapy in conjunction with other therapeutics known in the art for the treatment or prevention of unwanted immune responses for example but not limited to glucocorticoids, methotrexate, D-penicillamine, hydroxychloroquine, gold salts, sulfasalazine, TNFα or interleukin-1 inhibitors, and/or other forms of specific immunotherapy.

4. Preparation of Immunostimulatory Compositions

The preparation of the immunomodulating compositions of the present invention uses routine methods known to persons skilled in the art. Typically, such formulations and vaccines are prepared as injectables, either as liquid solutions or suspensions; solid forms suitable for solution in, or suspension in, liquid prior to injection may also be prepared. The preparation may also be emulsified. The active immunogenic ingredients are often mixed with excipients that are pharmaceutically acceptable and compatible with the active ingredient. Suitable excipients are, for example, water, phosphate buffered saline, saline, dextrose, glycerol, ethanol, or the like and combinations thereof. In addition, if desired, the vaccine may contain minor amounts of auxiliary substances such as wetting or emulsifying agents, pH buffering agents, and/or adjuvants that enhance the effectiveness of the vaccine. Examples of adjuvants which may be effective include but are not limited to: surface active substances such as hexadecylamine, octadecylamine, octadecyl amino acid esters, lysolecithin, dimethyldioctadecylammonium bromide, N, N-dicoctadecyl-N', N'bis(2-hydroxyethyl-propanediamine), methoxyhexadecylglycerol, and pluronic polyols; polyamines such as pyran, dextransulfate, poly IC carbopol; mineral gels such as aluminum phosphate, aluminum hydroxide or alum; peptides such as muramyl dipeptide and derivatives such as N-acetyl-muramyl-L-threonyl-D-isoglutamine (thur-MDP), N-acetyl-nor-muramyl-L-alanyl-D-isoglutamine (CGP 11637, referred to as nor-MDP), N-acetyl-muramyl-L-alanyl-D-isoglutaminyl-L-alanine-2-(1'-2'-dipalmitoyl-sn-glycero-3-hydroxyphosphoryloxy)-ethylamine (CGP 1983A, referred to as MTP-PE), and RIBI, which contains three components extracted from bacteria, monophosphoryl lipid A, dimethylglycine, tuftsin; oil emulsions; trehalose dimycolate and cell wall skeleton (MPL+TDM+CWS) in a 2% squalene/Tween 80 emulsion; lymphokines; QuilA and immune stimulating complexes (ISCOMS). For example, the effectiveness of an adjuvant may be determined by measuring antibody titres resulting from the administration of the immunostimulatory composition, wherein those antibodies are directed against one or more antigens presented by the treated cells of the immunostimulatory composition.

The active ingredients should be administered in a pharmaceutically acceptable carrier, which is non-toxic to the cells and the individual to be treated. Such carrier may be the growth medium in which the cells were grown. Compatible excipients include isotonic saline, with or without a physiologically compatible buffer like phosphate or HEPES and nutrients such as dextrose, physiologically compatible ions, or amino acids, and various culture media suitable for use with cell populations, particularly those devoid of other immunogenic components. Carrying reagents, such as albumin and blood plasma fractions and non-active thickening agents, may also be used. Non-active biological components, to the extent that they are present in the vaccine, are preferably derived from a syngeneic animal or human as that to be treated, and are even more preferably obtained previously from the subject. The injection site may be subcutaneous, intraperitoneal, intramuscular, intradermal, or intravenous. In preferred embodiments, the immunostimulatory composition is administered systemically. Preferably, the immunostimulatory composition is administered intramuscularly (e.g., by intramuscular injection). In some embodiments, the immunostimulatory composition is administered by a route other than intranasally. Suitably, the immunostimulatory composition is administered by a route other than mucosally.

If soluble actives are employed (e.g., a soluble inhibitor of IL-25 function) active ingredients can be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric, maleic, and the like. Salts formed with the free carboxyl groups may also be derived from inorganic basis such as, for example, sodium, potassium, ammonium, calcium, or ferric hydroxides, and such organic basis as isopropylamine, trimethylamine, 2-ethylamino ethanol, histidine, procaine, and the like.

If desired, devices or pharmaceutical compositions or compositions containing the vaccine and suitable for sustained or intermittent release could be, in effect, implanted in the body or topically applied thereto for the relatively slow release of such materials into the body.

Techniques for formulation and administration may be found in "*Remington's Pharmaceutical Sciences*," Mack Publishing Co., Easton, Pa., latest edition. Suitable routes may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

The dosage to be administered may depend on the subject to be treated inclusive of the age, sex, weight and general health condition thereof. The dosage will also take into consideration the binding affinity of the inhibitor of IL-25 function to its target molecule, the immunogenicity of the immune stimulator, their bioavailability and their in vivo and pharmacokinetic properties. In this regard, precise amounts of the agent(s) for administration can also depend on the judgment of the practitioner. In determining the effective amount of the agent(s) to be administered in the treatment of a disease or condition, the physician or veterinarian may evaluate the progression of the disease or condition over time. In any event, those of skill in the art may readily determine suitable dosages of the agents of the invention without undue experimentation. Cell-containing compositions and vaccines are suitably administered to a patient in the range of between about $10^4$ and $10^{10}$, and more preferably between about $10^6$ and $10^8$ treated cells/administration. The dosage of the actives administered to a patient should be sufficient to effect a beneficial response in the patient over time such as a reduction in the symptoms associated with the cancer or tumor. For example, usual patient dosages for systemic administration of inhibitors of IL-25 function range from about 0.1-200 g/day, typically from about 1-160 g/day and more typically from about 10-70 g/day. Stated in terms of patient body weight, usual dosages range from about 1.5-3000 mg/kg/day, typically from about 15-2500 mg/kg/day, more typically from about 150-1000 mg/kg/day and even more typically from about 20-50 mg/kg/day.

Thus, the inhibitor of IL-25 function and the immune stimulator may be provided in effective amounts to stimulate or enhance the immune response to a target antigen.

5. Methods for Stimulating Immune Responses

The compositions of the invention may be used for stimulating an immune response to a target antigen in a subject that is immunologically naïve to the target antigen or that has previously raised an immune response to that antigen. Thus, the present invention also extends to methods for enhancing an immune response in a subject by administering to the subject the compositions or vaccines of the invention. Advantageously, the immune response is a cell-mediated immune response (e.g., a T-cell mediated response, which desirably includes CD8$^+$ IFN-γ-producing T cells).

Also encapsulated by the present invention is a method for treatment and/or prophylaxis of a disease or condition, comprising administering to a patient in need of such treatment an effective amount of a inhibitor of IL-25 function, together with an effective amount of an immune stimulator, as broadly described above. In certain embodiments, the target antigen is associated with or responsible for a disease or condition which is suitably selected from cancers, infectious diseases and diseases characterized by immunodeficiency. Examples of cancer include but are not limited to ABL1 proto-oncogene, AIDS related cancers (e.g., Kaposi's sarcoma), acoustic neuroma, acute lymphocytic leukemia, acute myeloid leukemia, adenocystic carcinoma, adrenocortical cancer, agnogenic myeloid metaplasia, alopecia, alveolar soft-part sarcoma, anal cancer, angiosarcoma, aplastic anemia, astrocytoma, ataxia telangiectasia, basal cell carcinoma (skin), bladder cancer, bone cancers, bowel cancer, brain stem glioma, brain and CNS tumors, breast cancer, CNS tumors, carcinoid tumors, cervical cancer, childhood brain tumors, childhood cancer, childhood leukemia, childhood soft tissue sarcoma, chondrosarcoma, choriocarcinoma, chronic lymphocytic leukemia, chronic myeloid leukemia, colorectal cancers, cutaneous T-cell lymphoma, dermatofibrosarcoma protuberans, desmoplastic small round cell tumor, ductal carcinoma, endocrine cancers, endometrial cancer, ependymoma, esophageal cancer, Ewing's sarcoma, extra-hepatic bile duct cancer, eye cancer, eye: melanoma, retinoblastoma, fallopian tube cancer, fanconi anemia, fibrosarcoma, gall bladder cancer, gastric cancer, gastrointestinal cancers, gastrointestinal carcinoid tumor, genitourinary cancers, germ cell tumors, gestational-trophoblastic disease, glioma, gynecological cancers, hematological malignancies, hairy cell leukemia, head and neck cancer, hepatocellular cancer, hereditary breast cancer, histiocytosis, Hodgkin's disease, human papillomavirus, hydatidiform mole, hypercalcemia, hypopharynx cancer, intraocular melanoma, islet cell cancer, Kaposi's sarcoma, kidney cancer, Langerhans' cell histiocytosis, laryngeal cancer, leiomyosarcoma, leukemia, Li-Fraumeni syndrome, lip cancer, liposarcoma, liver cancer, lung cancer, lymphedema, lymphoma, Hodgkin's lymphoma, non-Hodgkin's lymphoma, male breast cancer, malignant-rhabdoid tumor of kidney, medulloblastoma, melanoma, Merkel cell cancer, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nephroblastoma, neuroblastoma, neurofibromatosis, Nijmegen breakage syndrome, non-melanoma skin cancer, non-small cell lung cancer (NSCLC), ocular cancers, esophageal cancer, oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal tumors, pituitary cancer, polycythemia vera, prostate cancer, rare-cancers-and-associated-disorders, renal cell carcinoma, retinoblastoma, rhabdomyosarcoma, Rothmund thomson syndrome, salivary gland cancer, sarcoma, schwannoma, Sezary syndrome, skin cancer, small cell lung cancer (SCLC), small intestine cancer, soft tissue sarcoma, spinal cord tumors, squamous-cell-carcinoma-(skin), stomach cancer, synovial sarcoma, testicular cancer, thymus cancer, thyroid cancer, transitional-cell-cancer-(bladder), transitional-cell-cancer-(renal-pelvis-/-ureter), trophoblastic cancer, urethral cancer, urinary system cancer, uroplakins, uterine sarcoma, uterus cancer, vaginal cancer, vulva cancer, Waldenstrom's-macroglobulinemia, Wilms' tumor.

In other embodiments, the composition of the invention could also be used for generating large numbers of CD8$^+$ or CD4$^+$ CTL, for adoptive transfer to immunodeficient individuals who are unable to mount normal immune responses. For example, antigen-specific CD8$^+$ CTL can be adoptively transferred for therapeutic purposes in individuals afflicted with HIV infection (Koup et al., 1991, *J. Exp. Med.* 174: 1593-1600; Carmichael et al., 1993, *J. Exp. Med.* 177: 249-256; and Johnson et al., 1992, *J. Exp. Med.* 175: 961-971), malaria (Hill et al., 1992, *Nature* 360: 434-439) and malignant tumors such as melanoma (Van der Brogen et al., 1991, *Science* 254: 1643-1647; and Young and Steinman 1990, *J. Exp. Med.,* 171: 1315-1332).

In still other embodiments, the composition is suitable for treatment or prophylaxis of a viral, bacterial or parasitic infection. Viral infections contemplated by the present invention include, but are not restricted to, infections caused by HIV, Hepatitis, Influenza, Japanese encephalitis virus, Epstein-Barr virus and respiratory syncytial virus. Bacterial infections include, but are not restricted to, those caused by *Neisseria* species, *Meningococcal* species, *Haemophilus* species *Salmonella* species, Streptococcal species, *Legionella* species and *Mycobacterium* species (e.g., *M. tuberculosis*). Parasitic infections encompassed by the invention include, but are not restricted to, those caused by *Plasmodium* species, *Schistosoma* species, *Leishmania* species, *Trypanosoma* species, *Toxoplasma* species and *Giardia* species.

The effectiveness of the immunization may be assessed using any suitable technique. For example, CTL lysis assays may be employed using stimulated splenocytes or peripheral blood mononuclear cells (PBMC) on peptide coated or recombinant virus infected cells using $^{51}$Cr or Alamar Blue™ labeled target cells. Such assays can be performed using for example primate, mouse or human cells (Allen et al., *J Immunol*, 2000, 164(9): 4968-4978 also Woodberry et al., infra). Alternatively, the efficacy of the immunization may be monitored using one or more techniques including, but not limited to, HLA class I tetramer staining—of both fresh and stimulated PBMCs (see for example Allen et al., supra), proliferation assays (Allen et al., supra), ELISPOT assays and intracellular IFN-γ staining (Allen et al., supra), ELISA Assays—for linear B cell responses; and Western blots of cell sample expressing the synthetic polynucleotides.

In some embodiments, the composition comprises a nucleic acid construct from which an antigen that corresponds to the target antigen is expressible. Administration of such nucleic acid constructs to a mammal, especially a human, may include delivery via direct oral intake, systemic injection, or delivery to selected tissue(s) or cells. Delivery of the nucleic acid constructs to cells or tissues of the mammal may be facilitated by microprojectile bombardment, liposome mediated transfection (e.g., Lipofectin or Lipofectamine), electroporation, calcium phosphate or DEAE-dextran-mediated transfection, for example. A discussion of suitable delivery methods may be found in Chapter 9 of Ausubel et al., (1994-1998, supra).

The step of introducing the expression vector into the selected target cell or tissue will differ depending on the intended use and species, and can involve one or more of non-viral and viral vectors, cationic liposomes, retroviruses, and adenoviruses such as, for example, described in Mulligan, R. C., (1993). Such methods can include, for example:

A. Local application of the expression vector by injection (Wolff et al., *Science*, 1990, 247 (4949 Pt 1): 1465-1468), surgical implantation, instillation or any other means. This method can also be used in combination with local application by injection, surgical implantation, instillation or any other means, of cells responsive to the protein encoded by the expression vector so as to increase the effectiveness of that treatment. This method can also be used in combination with local application by injection, surgical implantation, instillation or any other means, of another factor or factors required for the activity of the protein.

B. General systemic delivery by injection of DNA, (Calabretta et al., 1993), or RNA, alone or in combination with liposomes (Zhu et al., 1993), viral capsids or nanoparticles (Bertling et al., 1991) or any other mediator of delivery. Improved targeting might be achieved by linking the polynucleotide/expression vector to a targeting molecule (the so-called "magic bullet" approach employing, for example, an antigen-binding molecule), or by local application by injection, surgical implantation or any other means, of another factor or factors required for the activity of the protein encoded by the expression vector, or of cells responsive to the protein. For example, in the case of a liposome containing antisense IL-25 polynucleotides, the liposome may be targeted to skin cancer cells, e.g., squamous carcinoma cells, by the incorporation of immuno-interactive agents into the liposome coat which are specific the EGF receptor, which is expressed at higher levels in skin cancer.

C. Injection or implantation or delivery by any means, of cells that have been modified ex vivo by transfection (for example, in the presence of calcium phosphate: Chen et al., 1987, or of cationic lipids and polyamines: Rose et al., 1991), infection, injection, electroporation (Shigekawa et al., 1988) or any other way so as to increase the expression of the polynucleotide in those cells. The modification can be mediated by plasmid, bacteriophage, cosmid, viral (such as adenoviral or retroviral; Mulligan, 1993; Miller, 1992; Salmons et al., 1993) or other vectors, or other agents of modification such as liposomes (Zhu et al., 1993), viral capsids or nanoparticles (Bertling et al., 1991), or any other mediator of modification. The use of cells as a delivery vehicle for genes or gene products has been described by Barr et al., 1991 and by Dhawan et al., 1991. Treated cells can be delivered in combination with any nutrient, growth factor, matrix or other agent that will promote their survival in the treated subject.

5.1 Prime-Boost Regimens

The methods of the invention may comprise administering a priming composition of an immune stimulator or a polynucleotide sequence from which a nucleotide sequence encoding an immune stimulator is expressible, wherein the immune stimulator stimulates or otherwise enhances an immune response to a target antigen in a subject, and subsequently administering a later booster composition of the target antigen together with a second agent comprising an inhibitor of IL-25 function or a polynucleotide from which a nucleotide sequence encoding an inhibitor of IL-25 function is expressible as broadly defined above and elsewhere herein.

For example, the booster composition may be administered at least 7, 14, 21 or 28 days, at least 1, 2, 3, 4, 5, or 6 months, or at least 1, 2, 3, 4, or 5 years after the priming composition. The immune stimulator and the inhibitor of IL-25 function may be administered separately or sequentially. The priming and booster compositions may be administered by the same or different routes. For example, the priming and booster doses may both be administered—mucosally (e.g., intranasally), intramuscularly, intravenously, or subcutaneously. Alternatively, the priming dose may be administered locally (e.g., mucosally, such as intranasally) to induce mucosal antigen-specific immune cells, and the booster dose administered intramuscularly, subcutaneously, or intravenously to induce systemic antigen-specific immune cells. Preferably, the booster dose is administered intramuscularly. In preferred embodiments, the booster dose is administered by a route other than intranasally. Suitably, the booster dose is administered by a route other than mucosally.

Optionally, the priming dose of immune stimulator further comprises an inhibitor of IL-4 function or a polynucleotide from which a nucleotide sequence encoding an inhibitor of IL-4 is expressible. The inhibitor of IL-4 function includes any molecule or compound that directly or indirectly binds or physically associates with IL-4 or its receptor(s) and that suitably blocks, inhibits or otherwise antagonizes at least one of its functions or activities (e.g., binding to or interaction with one or more surface molecules (e.g., receptors) present on white blood cells, especially lymphocytes and more especially T lymphocytes). The binding or association may involve the formation of an induced magnetic field or paramagnetic field, covalent bond formation, an ionic interaction such as, for example, occur in an ionic lattice, a hydrogen bond or alternatively, a van der Waals interactions such as, for example, a dipole-dipole interaction, dipole-induced-dipole interaction, induced-dipole-induced-dipole interaction or a repulsive interaction or any combination of the above forces of attraction.

In certain embodiments, the inhibitor of IL-4 function is any molecule capable of specifically preventing activation of cellular receptors for IL-4. For example, inhibitors of this type can be selected from soluble native or variant IL-4 receptors or soluble IL-4 receptor subunits.

In certain embodiments, the inhibitor of IL-4 function is a variant form of IL-4, including but not limited to IL-4C123 or AEROVANT™ (AER 001, pitrakinra produced by Aerovance) which is a 15 kDa recombinant human IL-4 mutein (see, The Lancet, 2007, 370: 1422-1431).

Alternatively, such an inhibitor can be an antigen-binding molecule that is immuno-interactive with an IL-4 receptor. In these embodiments, the antigen-binding molecule may bind to the IL-4 receptor but will not signal via the receptor, thus blocking any host IL-4 signaling. In other embodiments, the inhibitor of IL-4 function is an antigen-binding molecule that is immuno-interactive with at least a portion of IL-4. In these embodiments, the antigen-binding molecules can be immuno-interactive with an active or an inactive form of IL-4, the difference being that antigen-binding molecules to the active cytokine are more likely to recognise epitopes that are only present in the active conformation. Representative examples of such inhibitors include ligands or single-chain antibodies.

In some embodiments, the second agent and the third agent may comprise the same molecule. Notably, in specific embodiments, the second agent and the third agent comprises the IL-4 variant, IL-4C123, which can bind to both the IL-4 type 1 receptor and the IL-4 type 2 receptor preventing cellular signalling through these pathways. An exemplary IL-4C123 polypeptide sequence is set out in SEQ ID NO: 100 (suitably encoded by the optimized nucleic acid sequence set forth in SEQ ID NO: 101), wherein:

SEQ ID NO: 100 is:
HKCDITLQEIIKTLNSLTEQKTLCTELTVTDIFAASKNTTEKETFCRAA

TVLRQFYSHHEKDTRCLGATAQQFHRHKQLIRFLKRLDRNLWGLAGLNS

CPVKEANQSTLENFLERLKTIMREK;
and

SEQ ID NO: 101 is:
ATGGGCCTGACCAGCCAGCTGCTGCCCCCCCTGTTCTTCCTGCTGGCCT

GCGCCGGCAACTTCGTGCACGGCCACAAGTGCGACATCACCCTGCAGGA

GATCATCAAGACCCTGAACAGCCTGACCGAGCAGAAGACCCTGTGCACC

GAGCTGACCGTGACCGACATCTTCGCCGCCAGCAAGAACACCACCGAGA

AGGAGACCTTCTGCAGAGCCGCCACCGTGCTGAGACAGTTCTACAGCCA

CCACGAGAAGGACACCAGATGCCTGGGCGCCACCGCCCAGCAGTTCCAC

AGACACAAGCAGCTGATCAGATTCCTGAAGAGACTGGACAGAAACCTGT

GGGGCCTGGCCGGCCTGAACAGCTGCCCCGTGAAGGAGGCCAACCAGAG

CACCCTGGAGAACTTCCTGGAGAGACTGAAGACCATCATGAGAGAGAAG

TGA.

6. Kits

The present invention also provides kits comprising an immunostimulatory compositions as broadly described above and elsewhere herein. Such kits may additionally comprises alternative immunogenic agents for concurrent use with the immunostimulatory compositions of the invention.

In some embodiments, in addition to the immunostimulatory compositions of the present invention the kit may include suitable components for performing the prime-boost regiments described above. For example, the kit may include a priming dose of the immune stimulator. Furthermore, the priming dose may also comprise an inhibitor if IL-4 function, as described in detail, above.

The kit may comprise additional components to assist in performing the methods of the present invention such as, for example, administration device(s), buffer(s), and/or diluent(s). The kits may include containers for housing the various components and instructions for using the kit components in the methods of the present invention.

In order that the invention may be readily understood and put into practical effect, particular preferred embodiments will now be described by way of the following non-limiting examples.

EXAMPLES

Example 1

Enhancing Immunity Through Inhibition of IL-25 Function

Materials & Methods

Mice 5-8-week-old pathogen free female BALB/c mice were obtained from the Australian Phenomics Facility, the Australian National University. Mice were handled and maintained under the Australian National University Animal Experimentation and Ethics Committee approved guidelines, protocol numbers A2014/14 and A2017-15.

Vaccine Preparation

IL-25BP Gene and Isolation of Recombinant Poxviruses
The synthetic gene for secreted IL-25BP encodes the signal peptide (removed during post-translational processing) and extracellular binding domains of mouse IL-17RB, the transmembrane and cytoplasmic domains are not included. IL-17RB is known to bind IL-17B (poorly defined immune activity) and IL-25 (also known as IL-17E). The synthetic IL-25BP gene was further codon optimized for efficient expression in mouse cells. The addition of an upstream in-frame coding sequence and BamHI restriction site allows in-frame ligation into the Fowlpox vector pAF09 early-late (TAA<u>ATG</u>) promoter (see, Heine, H. G., Boyle, D. B., Arch Virol, 1993, 131(3-4): 277-92). A downstream HindIII restriction site was included to facilitate sub-cloning. The following synthetic DNA sequence was custom prepared by GenScript USA/HK:

[SEQ ID NO: 102]
ATGCTGCTGGTGCTGCTGATCCTGGCCGCCAGCTGCAGGAGCGCCCTGCC

TAGGGAGCCTACCATCCAGTGCGGCAGCGAGACCGGCCCTAGCCCTGAGT

GGATGGTGCAGCACACCCTGACCCCTGGCGACCTGAGGGACCTGCAGGTG

GAGCTGGTGAAGACCAGCGTGGCCGCCGAGGAGTTCAGCATCCTGATGAA

CATCAGCATCCTGAGGGCCGACGCCAGCATCAGGCTGCTGAAGGCCACCA

AGATCTGCGTGAGCGGCAAGAACAACATGAACAGCTACAGCTGCGTGAGG

-continued

```
TGCAACTACACCGAGGCCTTCCAGAGCCAGACCAGGCCTAGCGGCGGCAA

GTGGACCTTCAGCTACGTGGGCTTCCCTGTGGAGCTGAGCACCCTGTACC

TGATCAGCGCCCACAACATCCCTAACGCCAACATGAACGAGGACAGCCCT

AGCCTGAGCGTGAACTTCACCAGCCCTGGCTGCCTGAACCACGTGATGAA

GTACAAGAAGCAGTGCACCGAGGCCGGCAGCCTGTGGGACCCTGACATCA

CCGCCTGCAAGAAGAACGAGAAGATGGTGGAGGTGAACTTCACCACCAAC

CCTCTGGGCAACAGGTACACCATCCTGATCCAGAGGGACACCACCCTGGG

CTTCAGCAGGGTGCTGGAGAACAAGCTGATGAGGACCAGCGTGGCCATCC

CTGTGACCGAGGAGAGCGAGGGCGCCGTGGTGCAGCTGACCCCTTACCTG

CACACCTGCGGCAACGACTGCATCAGGAGGGAGGGCACCGTGGTGCTGTG

CAGCGAGACCAGCGCCCCTATCCCTCCTGACGACAACAGGAGGATGCTGG

GCGGCTGA
```

Recombinant Fowlpox Virus

The synthetic IL-25BP DNA was ligated between the BamHI and HindIII sites of the FPV vector pAF09 (see, Heine, supra) (FIG. 1A). The IL-25BP gene is indicated by a solid red arrow downstream of the FPV early-late promoter. The flanking FPV genes are shown as black arrows. Selectable markers xanthine guanine phosphoribosyl transferase (ECOGPT, green) and β-galactosidase (BGAL LacZ, blue) are shown.

Recombinant fowlpox viruses co-expressing HIVgag and IL-25BP was constructed using parent virus FPV-HIV (HIVgagpol/env AE) (see, Coupar, B. E., et al., Vaccine, 2006, 24(9): 1378-88). The IL-25BP gene was transferred into the FPV-HIV genome by homologous recombination using Lipofectamine 2000 mediated plasmid DNA transfection of FPV-HIV infected chick embryo skin cells, mycophenolic acid/xanthine selection and identification of β-galactosidase positive recombinant plaques using X-gal staining (see, Heine, supra; and Jackson, R. J., Boyle, D. B., Ranasinghe, C., *Methods Mol Biol,* 2014, 1143: 61-90).

Recombinant MVA Virus

The IL-25BP gene as ligated between the BamHI and HindIII sites of the MVA vector pMVAdel III-TDS (Ronald Jackson, unpublished) downstream of a early/late promoter, including a HindIII cassette containing the Psyn-β-glucuronidase (GUS) gene (FIG. 1B). This transfer vector contains an insertion site located within the natural deletion-III region of MVA between open reading frames MVA164 and MVA165. Recombinant MVA expressing IL-25BP was isolated by Lipofectamine 2000 mediated plasmid transfection of MVA infected chick embryo skin cells, using the transient dominant selection procedure (see, Falkner, F. G., Moss, B., *J Virol,* 1990, 64(6): 3108-11) of the green fluorescent protein expression and Blasticidin S resistance and identification of recombinant virus plaques expressing GUS using X-gluc staining (see, Jackson, R. J., Hall, D. F., Kerr, P. J., *J Gen Virol,* 1996, 77(7): 1569-75).

Viruses

FPV-HIV expresses HIV genes gag-pol and env genes (AE clade) inserted into the "F" and "REV" sites respectively, was described by Coupar et al. FPV has abortive replication in mammals, however expresses both early and late promoter controlled viral genes.

MVA is the attenuated Modified Vaccinia Ankara vaccine strain of vaccinia virus that has abortive replication in mammals (see, Kennedy, J. S., Greenberg, R. N., *Expert Rev Vaccines,* 2009, 8(1), 13-24) and expresses both early and late promoter controlled viral genes.

MVA-HIVgagpol(AE) was previously constructed as follows: polymerase chain reaction isolation of the fowlpox virus early/late promoter and HIVgag-pol genes from FPV092 and sub-cloning into the MVA vector MVA-F-GFPBSD (Ronald Jackson, unpublished) into a synthetic intergenic region between MVA036(F7L) and MVA037 (F8L) open reading frames. Recombinant MVA-HIVgagpol (AE) was isolated as Green Fluorescent Protein positive, Blasticidin S resistant plaques (Ronald Jackson, unpublished).

Immunization of Mice

ILC Immunization Studies

BALB/c mice were administered $1\times10^7$ plaque forming units (PFU) rFPV control or rFPV-IL-25BP vaccines (expressing the HIV or TB antigens) by intramuscular (i.m.) injection. The i.m. vaccines were administered as 50 μl quadriceps muscle. All vaccines were diluted in sterile phosphate buffered saline (PBS) and sonicated three times for 15 seconds at 50% output using a Branson Sonifier 450 to distribute virus particles prior to use.

Prime-Boost Vaccination

Prime immunization FPV-HIV ($1\times10^7$ PFU) was administered intra-nasally as described previously (see, Ranasinghe 2013; and Jackson 2014a, supra) Two weeks following the i.n. prime immunization a mixture of MVA-HIV ($1\times10^7$ PFU) and MVA-IL25BP ($1\times10^7$ PFU) was administered by i.m. injection to boost the mucosal and systemic HIV or TB specific immune responses. This was compared to the control prime-boost vaccination using the non-adjuvant i.n. FPV-HIV/i.m. MVA-HIV. Two weeks post boost immunization $HIVgag_{(197-205)}$ specific $CD8^+$ T cell responses in the Peyer's patches (mucosal immunity) and spleen (systemic immunity) were analyzed for cytokine poly-functionality by intracellular cytokine staining for IFN-γ, TNF-α, IL-17A and IL-22 using methods described previously (see, Jackson 2014a; Ranasinghe, 2013; Jackson 2014b, supra; and Ravichandran, J., et al., *Cytokine Res,* 2015, 35(3): 176-85).

Preparation of Single Cell Suspensions

For Innate Lymphoid Cell (ILC) studies, muscle cells were isolated 24 hours post immunization. Vaccinated muscle was cut into <5 mm pieces and digested with 0.5 mg/ml collagenase, 2.4 mg/ml dispase, 5 Units/ml DNase in complete RPMI for 30 minutes at 37° C., then passed through a Falcon cell strainer to remove debris. The separated cells were washed and suspended in complete RPMI (5% FBS), rested overnight at 37° C. with 5% to allow recovery of cell surface markers and then stained for multi-color flow cytometry analysis.

For $CD8^+$ T cell analysis, mice were euthanized at two weeks post-boost immunization. Spleen and intestinal Peyer's patches were removed and single cell suspensions prepared in complete (5% FBS) RPMI. Spleens were dissociated through a Falcon cell strainer and suspended in red blood cell lysis buffer (0.15 mM $NH_4Cl$, 10.0 mM $KHCO_3$, 0.1 mM $Na_2EDTA$) at room temperature for 10 minutes to lyse the red blood cells. The cells were then washed and suspended in complete RPMI. Similarly, Peyer's patch mucosal lymphocytes were prepared as for spleen without the red cell lysis step (as described in Jackson, 2014a).

Flow Cytometry

Monoclonal antibodies FITC-conjugated anti-mouse CD3 (clone 17A2), CD19 (clone 6D5), CD11b (clone M1/70), CD11c (clone N418), CD49 (clone HMα2), FcεRIα (clone MAR-1) (all linage positive markers were selected as FITC). Linage positive cells are: $CD3^+$ T cells, $CD19^+$ B cells, $CD11c^+$ $CD11b^+$ macrophages and dendritic cells, $CD49^+$ NK cells, FcεRIα$^+$ mast cells and basophils. Lineage negative cells do not express the recognised cell surface markers of lineage-positive immune cells and contain the recently identified Innate Lymphoid Cell (ILC) populations.

PE-conjugated anti-mouse ST2/IL-33R (clone DIH9), APC-conjugated anti-mouse IL-17RB (IL-25R, clone 9610), APC/Cy7-conjugated anti-mouse CD45 (clone 30-F11), Brilliant Violet 421-conjugated anti-mouse CD335 (NKp46) (clone 29A1.4), Brilliant Violet 421-conjugated anti-mouse IL-4 (clone 11611), Brilliant Violet 510-conjugated anti-mouse IFN-γ (clone XMG1.2), APC-conjugated IL-22 (clone Poly5164), Alexa Fluor 700-conjugated IL-17A (clone TC11-18H10.1) were obtained from BIOLEGEND. PE-eFlour 610-conjugated anti-mouse IL-13 (clone eBio13A) was purchased from eBioscience.

The ILC cell surface and intracellular cytokine staining were performed according established protocols (see, Jackson 2014a; Ranasinghe, 2013; Jackson 2014b, and Ravichandran, 2015 supra), fixed with 0.5% paraformaldehyde, and run on a BD LSR Fortessa. From each sample $2 \times 10^6$ events were acquired and data were analyzed with Tree Star FlowJo software (version 10.0.7 for Windows) using a gating strategy adapted from Kim et al., 2012 (Kim, H. Y., et al., *J Allergy Clin*, 2012, 129(1): 216-27).

APC-conjugated $K_dGag_{197-205}$ tetramers were synthesized at the Bio-Molecular Resource Facility at The John Curtin School of Medical Research, ANU. Splenocytes or mucosal lymphocytes ($2-5 \times 10^6$) were stained with anti-CD8-FITC antibody (BIOLEGEND) and APC-conjugated $K_dGag_{197-205}$ tetramer and analyzed by intracellular cytokine staining and flow cytometry as previously described (see, Jackson 2014a; Ranasinghe, 2013; Jackson 2014b, and Ravichandran, 2015 supra).

Results

Analysis of ILC in Response to Intramuscular Immunization with FPV Vaccine

ILC2 Cells

Figure 2:
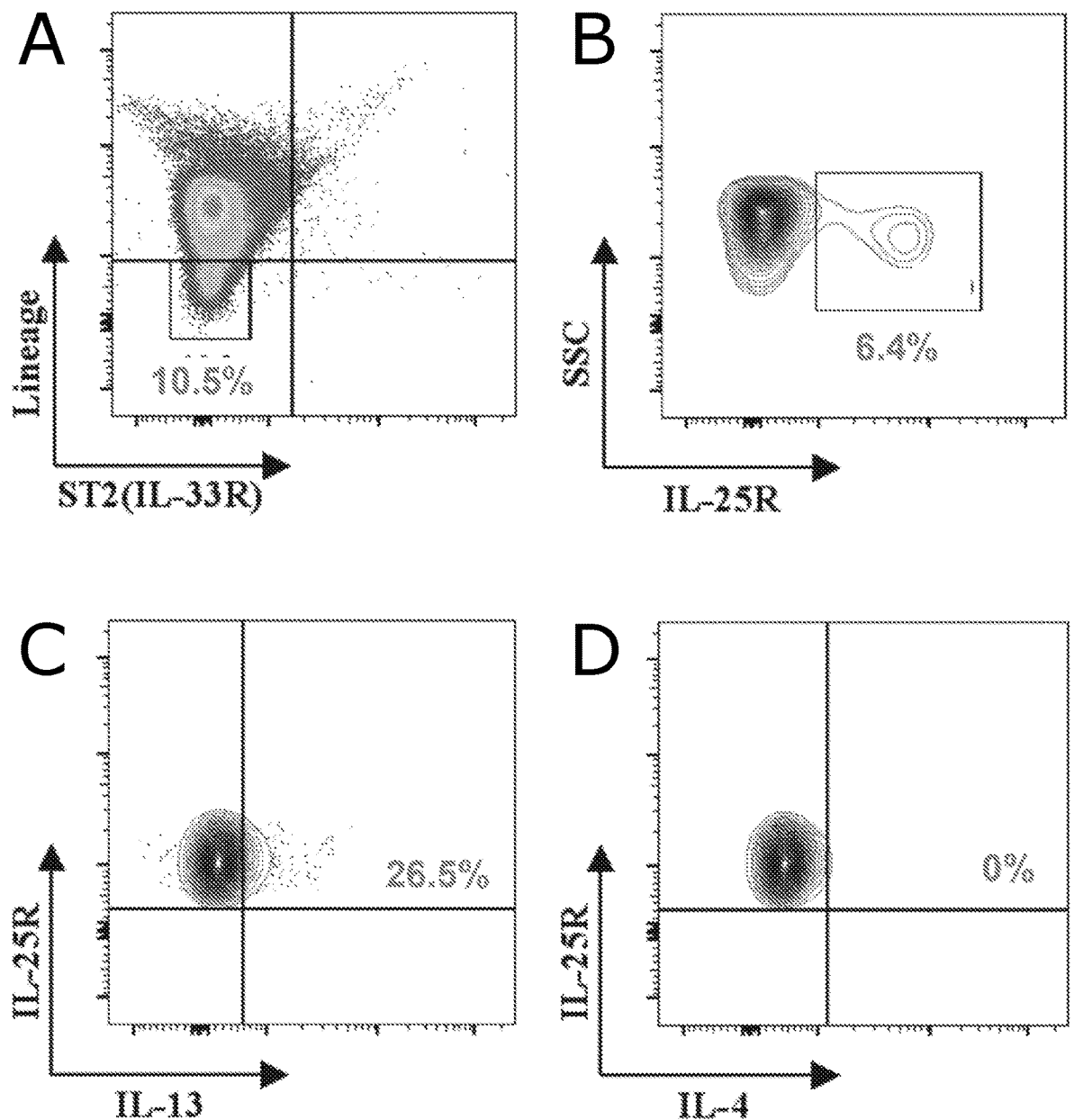
FIG. 2. Evaluation of ILC2 following FPV-HIV vaccination. Following intramuscular (i.m.) vaccination with FPV-HIV, CD45$^+$ cells were analyzed by flow cytometry for lineage negative cells. FITC-conjugated anti-mouse CD3 (clone 17A2), CD19 (clone 6D5), CD11b (clone M1/70), CD11c (clone N418), CD49 (clone HMα2), FcεRIα (clone MAR-1) (all lineage positive markers were selected as FITC) were used to gate out the lineage-positive cells containing, T cells (CD3$^+$), B cells (CD19$^+$), macrophages and dendritic cells (CD11b$^+$, CD11c$^+$), NK cells (CD49$^+$), mast cells and basophils (FcεRIα$^+$) The Lineage negative population (A, bottom left quadrant) was further analyzed for ST2 (IL-33R). Data indicated that in ILC2 in muscle do not express IL-33R but express IL-25R (B). When IL-25R$^+$ ILC2 were further characterized for IL-13 (C) and IL-4 (D) expression by intracellular cytokine staining, data revealed that activated muscle ILC2 cells express IL-13 but not IL-4.

Mice were given intramuscular immunizations with non-adjuvant FPV vaccine. Innate Lymphoid cells (ILC) present in the inoculated muscle were prepared 24 hours post immunization, then analyzed by flow cytometry (FIG. 2). $CD45^+$, Lineage-negative (Lin$^-$) cells were further analyzed for surface ST2 (IL-33R). Data demonstrate that muscle ILC2 do not express surface IL-33R, but do express IL-25R (IL-17RB). When the muscle IL-25R$^+$ ILC2 were further characterized for IL-13 and IL-4 expression, data revealed that activated muscle ILC2 express IL-13, but not IL-4.

ILC1 & ILC3 Cells

Figure 3:
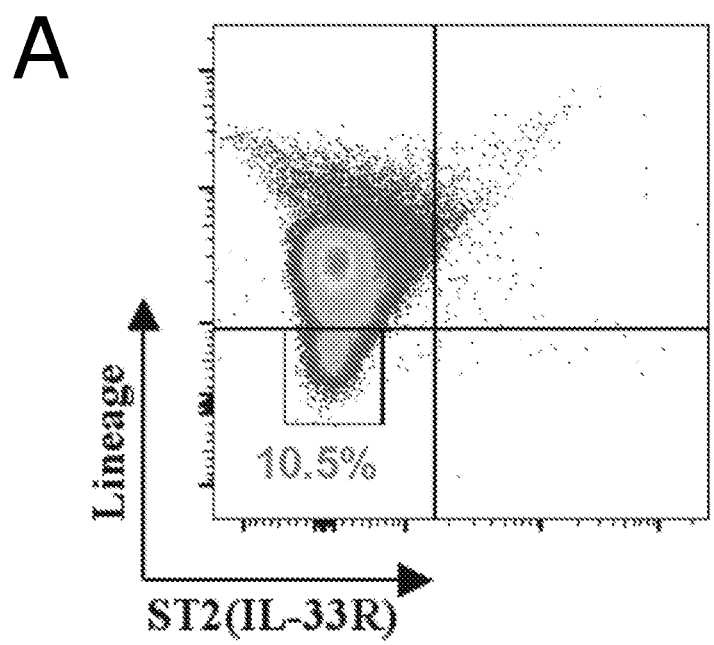
FIG. 3. Evaluation of ILC 1 & 3 following unadjuvanted FPV-HIV vaccination. Following FPV-HIV vaccination, muscle ILC that were CD45$^+$, Lin$^-$, IL-33R$^-$ (as shown in A) were further analyzed for cell surface NKp46$^-$ and NKp46$^+$ (B) innate lymphoid cells containing ILC1 and ILC3 cell populations.
Figure 3:
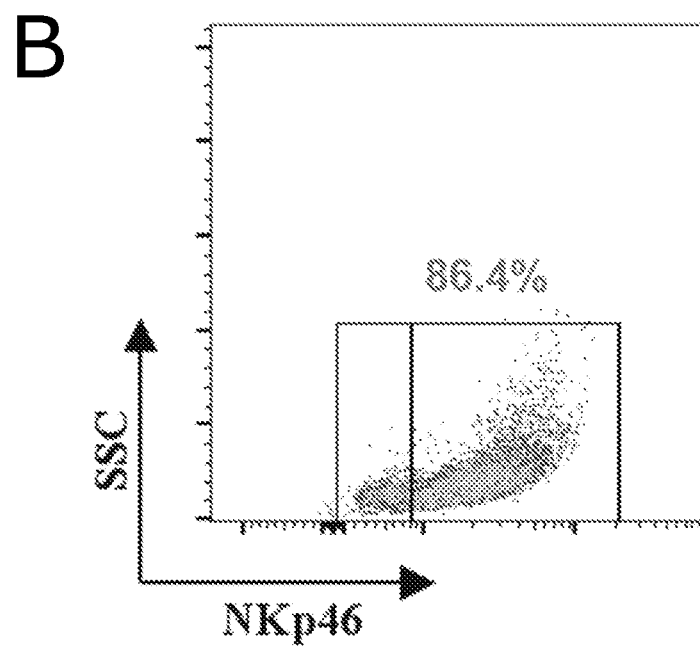
Figure 4:
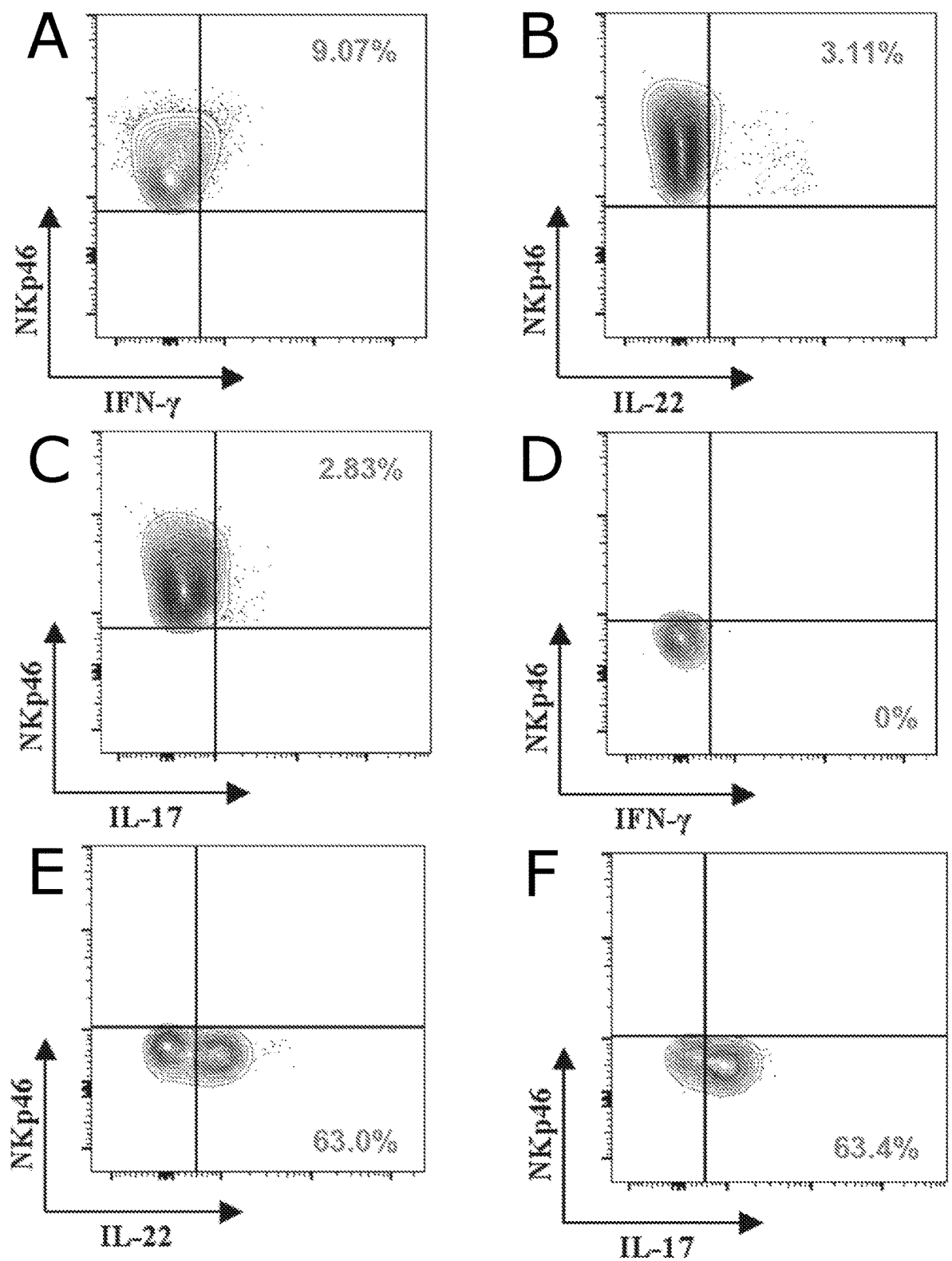
FIG. 4. Evaluation of ILC1 & ILC3 in muscle following i.m. FPV-HIV vaccination. The 2-D plots A, B, and C indicate the expression pattern of (A) IFN-γ, (B) IL-22 and (C) IL-17A by CD45$^+$ Lin$^-$ IL-33R$^-$ NKp46$^+$ cells. The 2-D plots D, E, and F indicate the expression pattern of expressing (D) IFN-γ, (E) IL-22 and (F) IL-17A in CD45$^+$ Lin$^-$ IL-33R$^-$ NKp46$^-$ cells.

Muscle $CD45^+$, Lin$^-$, IL-33R$^-$ were further analyzed for surface NKp46$^+$ and NKp46$^-$ populations (FIG. 3). The NKp46$^+$ and NKp46$^-$ populations were further characterized for expression of interferon-γ (ILC1) or IL-17A and IL-22 (ILC3) expressing cells (FIG. 4). The flow cytometry data indicates that Lin$^-$ NKp46$^+$ cells express IFN-γ, IL-17A and IL-22 and therefore contain both ILC1 and ILC3 populations. Notably, the Lin$^-$ NKp46$^-$ cells express IL-17A and IL-22 (and not IFN-γ), indicating the presence of only ILC3 populations.

Figure 5:
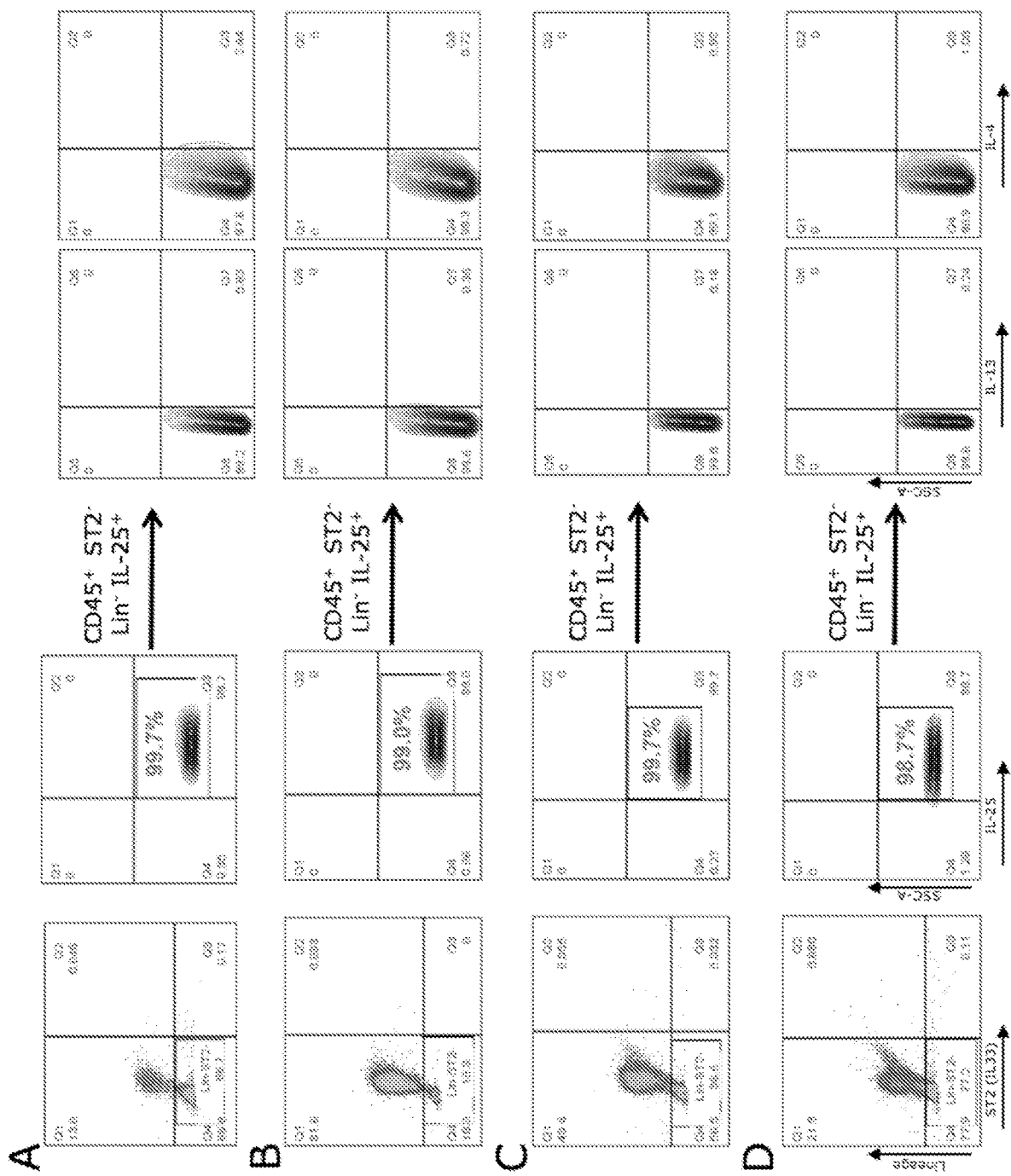
FIG. 5. Evaluation of ILC2 following FPV-HIV-IL25RBP i.m. vaccination. BALB/c mice (n=4) were immunized by intramuscular FPV-HIV-IL25BP and ILC2 evaluated 24 hours post vaccination. Data indicate that following FPV-IL25BP vaccination muscle ILC2 do not express IL-33R (CD45$^+$ Lin$^-$ IL-33R$^-$ (ST2$^-$)) but in contrast all ILC2 induced (99%) were IL-25R$^+$ compared to control unadjuvanted FPV-HIV vaccine strategy where only ~6% of the ILC2 were IL-25R$^+$ (see, FIG. 1). Intracellular cytokine staining indicated that these cells did not express IL-13 or IL-4. Data indicate that transient inhibition of IL-25 activation in muscle by FPV-IL25BP vaccination, completely inhibits IL-13 production by CD45$^+$ Lin$^-$ IL-33R$^-$ IL-25R$^+$ ILC2 cells compared to unadjuvanted i.m. FPV-HIV vaccination.

Analysis of ILC in Response to Intramuscular Immunization with FPV-IL25BP Vaccine ILC2 Cells BALB/c mice were immunized by intramuscular FPV-IL25BP vaccination and ILC2 ($CD45^+$, Lin$^-$, ST2$^-$, IL-25R$^+$) populations analyzed 24 hours post-immunization (FIG. 5). Data indicate that in response to FPV-IL25BP vaccination, muscle ILC2 do not express IL-33R. All Lin$^-$ ILC that were induced (99%) were IL-25R$^+$, in comparison to the non-adjuvant control FPV-HIV vaccine strategy where only ~6% of the ILC were IL-25R$^+$ ILC2 (FIG. 2). Intracellular cytokine staining indicated these IL-25R$^+$ ILC2 did not express IL-13 or IL-4. This data indicates that transient inhibition of IL-25R signaling, by sequestering free IL-25 in muscle by FPV-IL25BP vaccination, completely inhibited activation and IL-13 production by $CD45^+$ Lin$^-$ IL-33R$^-$ IL-25R$^+$ ILC2 compared to non-adjuvanted i.m. administration of FPV-HIV vaccination (FIG. 2).

ILC1 & ILC3 Cells

Figure 6:
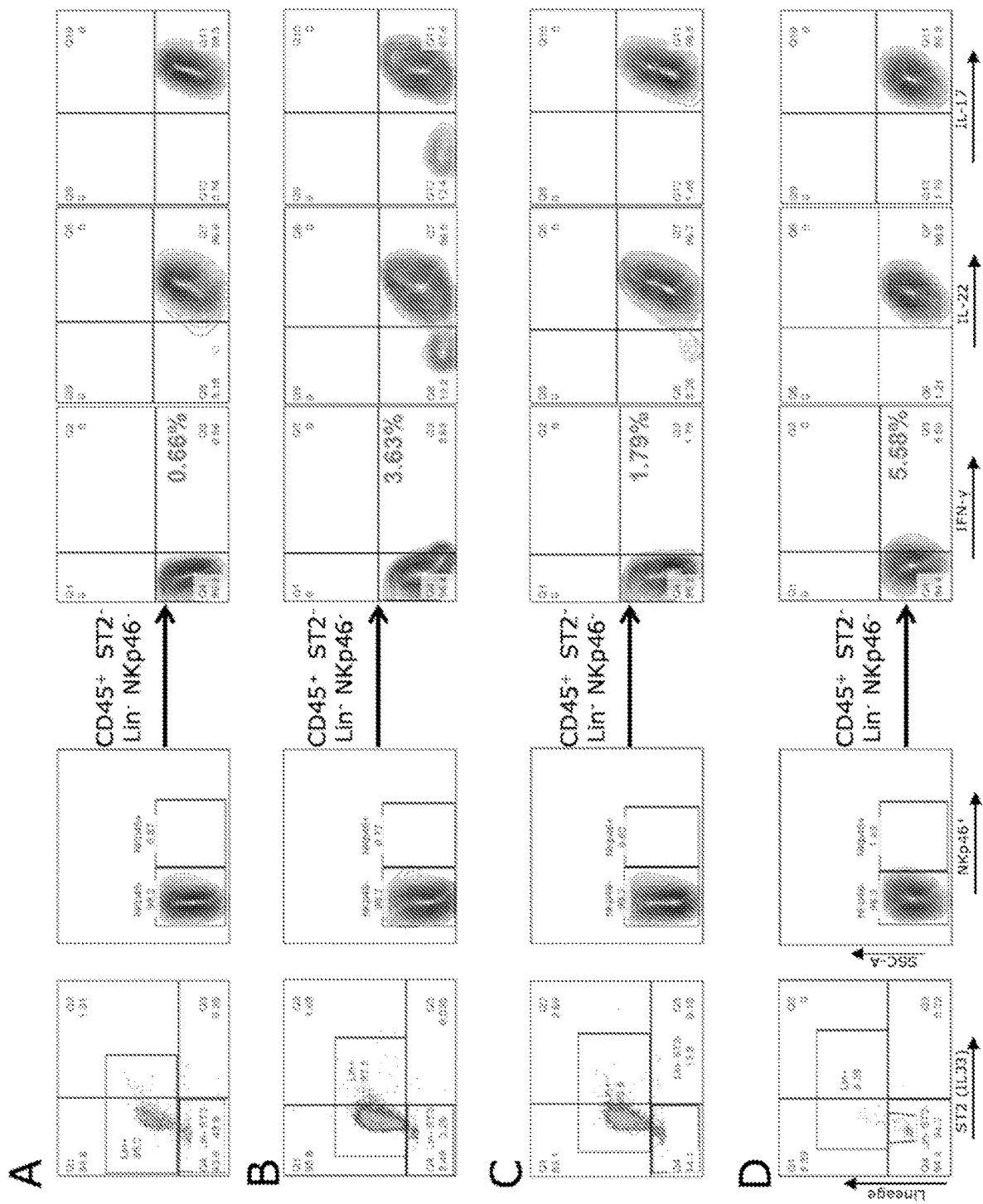
FIG. 6. Evaluation of ILC 1 & 3 following FPV-HIV i.m. vaccination. BALB/c mice (n=4) were immunized by intramuscular FPV-IL25BP and ILC1-like and ILC3-like cells were evaluated 24 hours post vaccination. Data indicate that following FPV-IL-25BP vaccination a majority of the CD45$^+$ Lin$^-$ IL-33R$^-$ ILC3 like cells were NKp46$^-$ and expressed elevated IL-17A (~98%) and IL-22 (~98%), but no or little IFN-γ was detected. Furthermore, no appreciable NKp46$^+$ population (<1.5%) was detected compared with the non-adjuvanted i.m. FPV-HIV vaccination (~86%) (see, FIGS. 2 and 3).

BALB/c mice were immunized by i.m. FPV-IL25BP vaccination and ILC1-like and ILC3-like cells evaluated 24 hours post vaccination (FIG. 6). Data indicates that following FPV-IL25BP vaccination the majority of $CD45^+$ Lin$^-$ IL-33R/ST2$^-$ ILC3-like cells were NKp46$^-$ (99%) and express elevated IL-17A (~98%) and IL-22 (~98%), but no or little IFN-γ expression was detected by "ILC1-like" cells. Furthermore, no appreciable NKp46$^+$ populations (<1.5%) were detected compared with non-adjuvanted i.m. FPV-HIV vaccination (~86%) (see, FIGS. 3 & 4).

Prime-Boost Immunization with FPV-HIVgag/MVA-HIVgag-IL25BP Vaccines

Twenty-four hours post i.n. FPV-HIV vaccination, lung mucosal ILC2 are exclusively IL-33R$^+$ (ST2$^+$) and express IL-13. In contrast, 24 hours post i.m. vaccination FPV-HIV vaccination muscle ILC2 cells are exclusively IL-25R$^+$ and express IL-13. Intranasal vaccination with FPV-HIV also induces IL-22 expression, however, it does not induce IL-17A expression by mucosal Lin$^-$ ST2$^-$. In contrast, i.m. FPV-HIV immunization induces muscle ILC3 cells expressing both IL-22 and IL-17A. These results indicate that lung ILC2 and muscle ILC2 are distinct populations with respect to cell receptor expression and cytokine repertoire.

The results presented herein show that transient inhibition of IL-25R signaling of muscle ILC2, by sequestering free IL-25 using a soluble IL-25BP expressed during vaccination, inhibits activation and maturation of IL-25R$^+$ ILC2. Nearly 100% of the Lin$^-$ ILC cells differentiate to a NKp46$^-$ ILC3-like phenotype expressing both IL-17A and IL-22. Interestingly, these ILC3-like cells are also IL-25R$^+$, having a mixed ILC2 (surface receptor) and ILC3 (cytokine) phenotype. ($CD45^+$ Lin$^-$ IL-33R$^-$ IL-25R$^+$ NKp46$^-$ IL-17A$^+$ IL-22$^+$).

The present inventors performed a heterologous recombinant poxvirus prime-boost vaccination directed at HIVgag antigen T cell immunity to determine whether transient inhibition of IL-25 signaling during the i.m. vaccination would enhance antigen-specific T cells. BALB/c mice (n=4/group) were i.n. primed with recombinant FPV-HIV and then two weeks later i.m. boosted with either an equal mixture of MVA-HIV/MVA-IL25BP adjuvant vaccine, or a MVA-HIV vaccine control.

Figure 7:
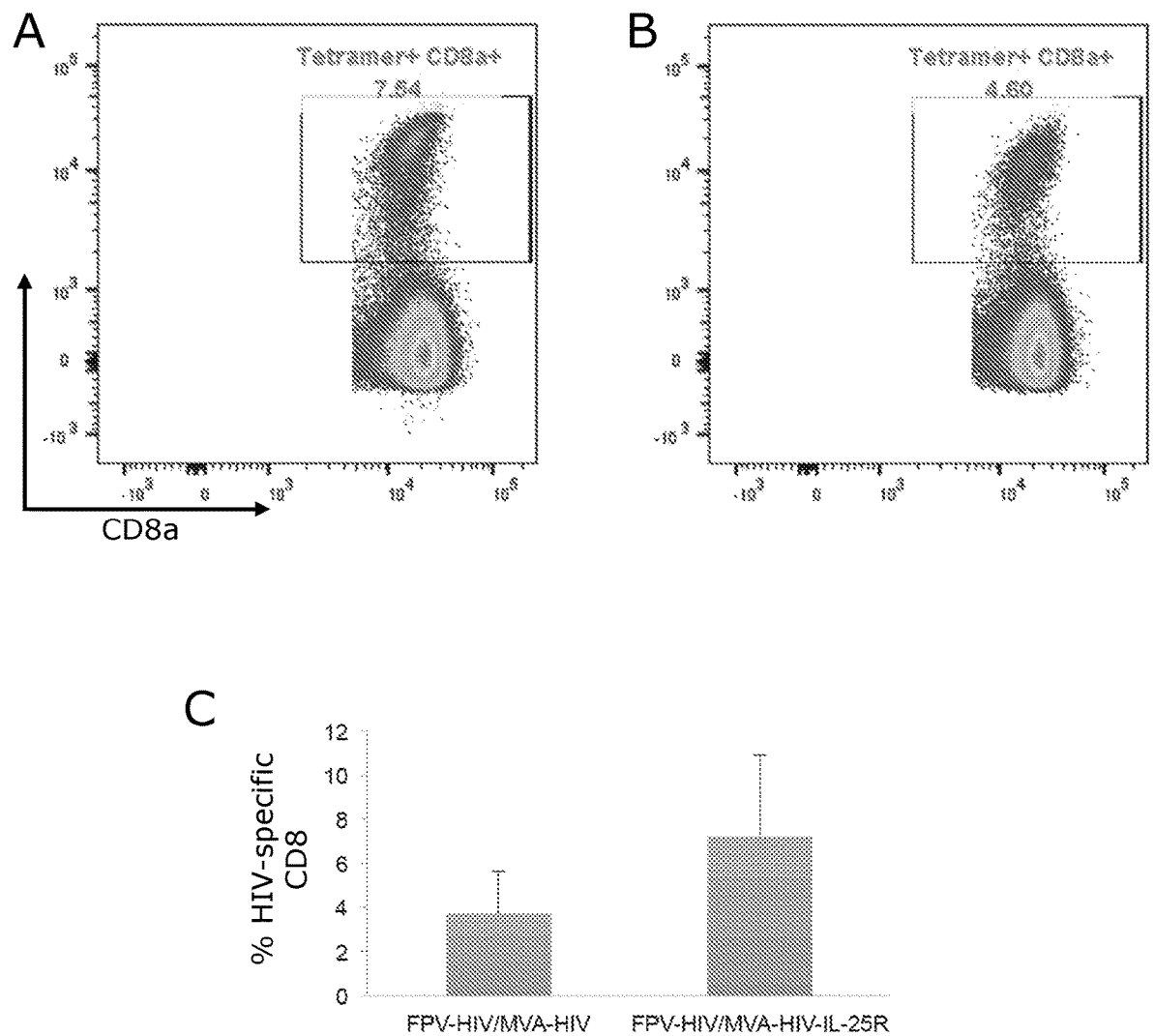
FIG. 7. Evaluation of systemic HIV-specific CD8$^+$ T cell responses following FPV-HIV/MVA-HIV-IL-25RBP adjuvanted vaccination. HIV-specific CD8$^+$ T cell responses following FPV-HIV intranasal (i.n.) prime, followed by MVA-HIVgag-IL-25BP adjuvant intramuscular (i.m.) booster vaccination measured by Kd-Gag-specific tetramer staining in spleen (systemic). The plots represent cells gated on CD8$^+$ T cells.
Figure 8:
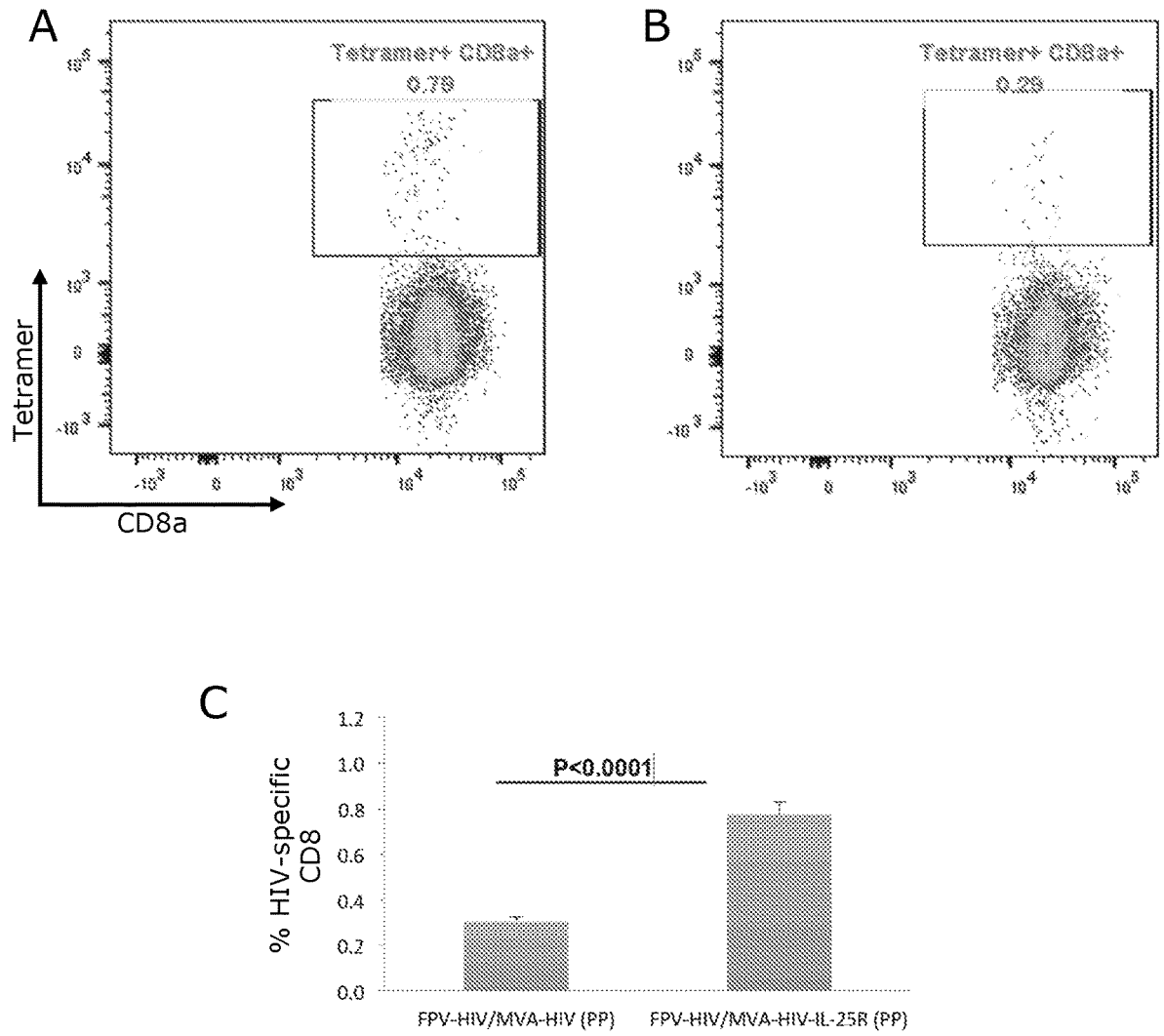
FIG. 8. Evaluation of mucosal HIV-specific CD8$^+$ T cell responses following FPV-HIV/MVA-HIV-IL-25RBP adjuvanted vaccination. HIV-specific CD8$^+$ T cell responses following FPV-HIV intranasal (i.n.) prime, followed by MVA-HIVgag-IL-25BP adjuvant intramuscular (i.m.) booster vaccination measured by Kd-Gag-specific tetramer staining in Payer's Patch (mucosal). Significantly elevated numbers of HIV-gag specific CD8$^+$ cells were detected in Peyer's Patch with the adjuvanted vaccine strategy compared to the control unadjuvanted i.n. FPV-HIV/i.m. MVA-HIV prime-boost vaccine strategy. The plots represent cells gated on CD8$^+$ T cells.

Following i.m. vaccine boosting, HIVgag specific CD8$^+$ T cells were measured by Kd-gag-specific tetramer staining of spleen (systemic) and Peyer's patch (mucosal) cells (FIGS. 7 and 8). Significantly elevated numbers of HIVgag specific CD8$^+$ cells were detected in Peyer's patch with the adjuvanted vaccine strategy compared to the control unadjuvanted i.n. FPV-HIV/i.m. MVA-HIV prime-boost vaccine strategy.

Figure 9:
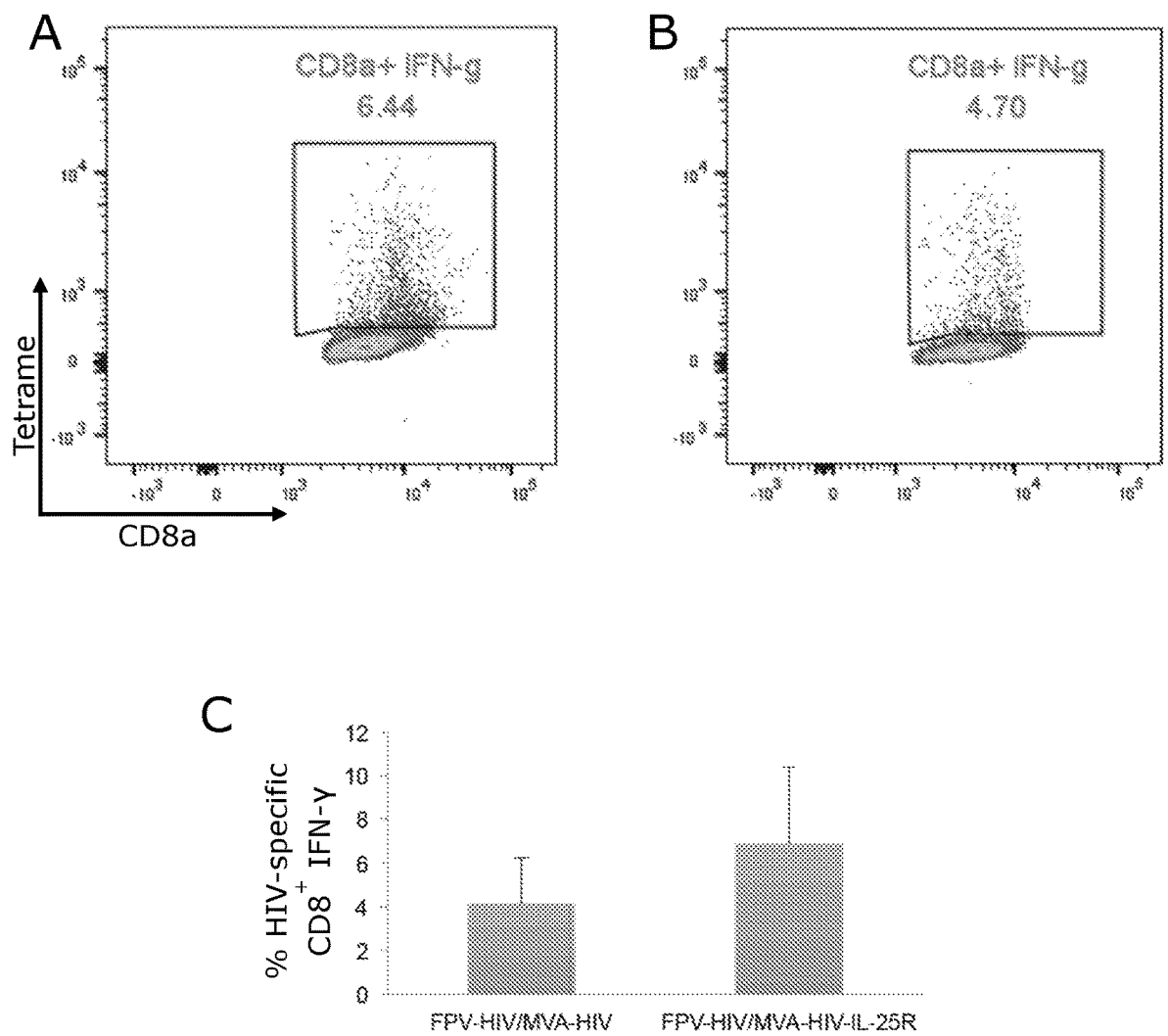
FIG. 9. Evaluation IFN-γ expression by HIVgag-specific CD8$^+$ T cells in spleen (systemic) following i.n. FPV-HIV prime, followed by i.m. MVA-HIVgag-IL-25BP adjuvant booster vaccination. Elevated numbers of HIV-gag specific CD8$^+$ cells expressing IFN-γ were detected in spleen relative to the control unadjuvanted i.n. FPV-HIV/i.m. MVA-HIV vaccination strategy. Note: The plots represent cells gated on CD8$^+$ T cells.
Figure 10:
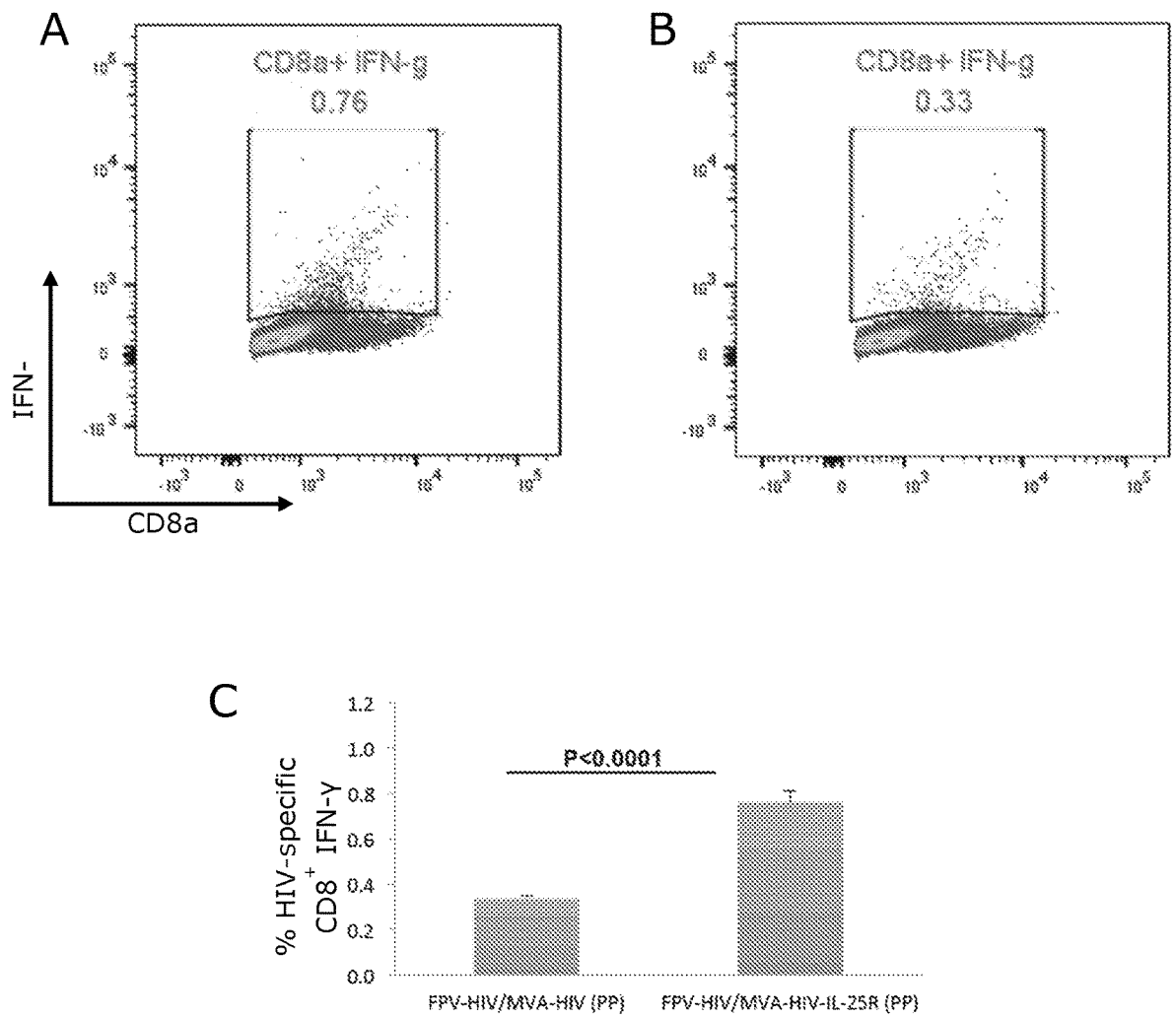
FIG. 10. Evaluation IFN-γ expression by HIVgag-specific CD8$^+$ T cells in Payer's Patches (mucosal) following i.n. FPV-HIV prime, followed by i.m. MVA-HIVgag-IL-25BP adjuvanted booster vaccination. Elevated numbers of HIV-gag-specific CD8$^+$ cells expressing IFN-γ were detected in Peyer's Patch relative to the control unadjuvanted i.n. FPV-HIV/i.m. MVA-HIV vaccination strategy. Note: The plots represent cells gated on CD8$^+$ T cells.

Spleen and Peyer's patch HIVgag specific CD8$^+$ T cells were evaluated for IFN-γ expression following prime-boost FPV-HIV/MVA-HIV-IL25BP vaccination (FIGS. 9 and 10). Elevated numbers of HIVgag specific CD8$^+$ cells expressing IFN-γ were detected in Peyer's patch relative to control unadjuvanted i.n. FPV-HIV/i.m. MVA-HIV vaccination strategy.

Figure 11:
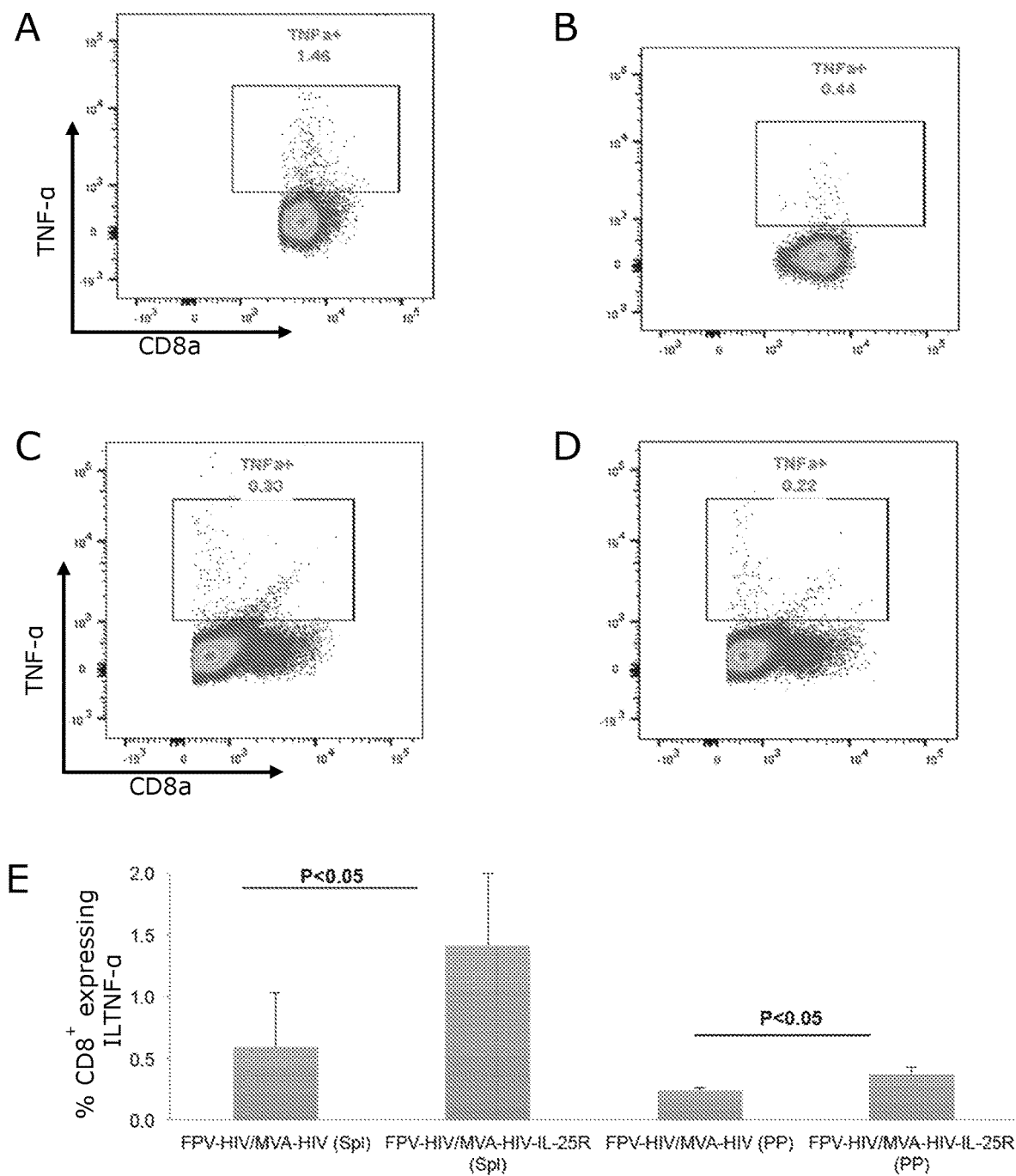
FIG. 11. Evaluation TNF-α expression by HIVgag-specific systemic (spleen; A, B) and mucosal (Peyer's Patch; C, D) CD8$^+$ T cells following i.n. FPV-HIV prime, followed by i.m. MVA-HIVgag-IL-25BP adjuvanted booster vaccination. Although no differences were detected in the mucosal compartment, elevated numbers of TNF-α expressing HIV-gag specific CD8$^+$ cells were detected both in spleen and Peyer's Patch relative to the control unadjuvanted i.n. FPV-HIV/i.m. MVA-HIV vaccination strategy (E). The plots represent cells gated on CD8$^+$ T cells.

Spleen and Peyer's patch HIVgag specific CD8$^+$ T cells were evaluated for TNFα expression following prime boost FPV-HIV/MVA-HIV-IL25BP vaccination (FIG. 11). Although no significant differences were detected in the mucosal compartment (Peyer's patch), elevated numbers of TNF-α expressing HIVgag specific CD8$^+$ cells were observed in spleen relative to the control unadjuvanted i.n. FPV-HIV/i.m. MVA-HIV vaccination strategy.

Figure 12:
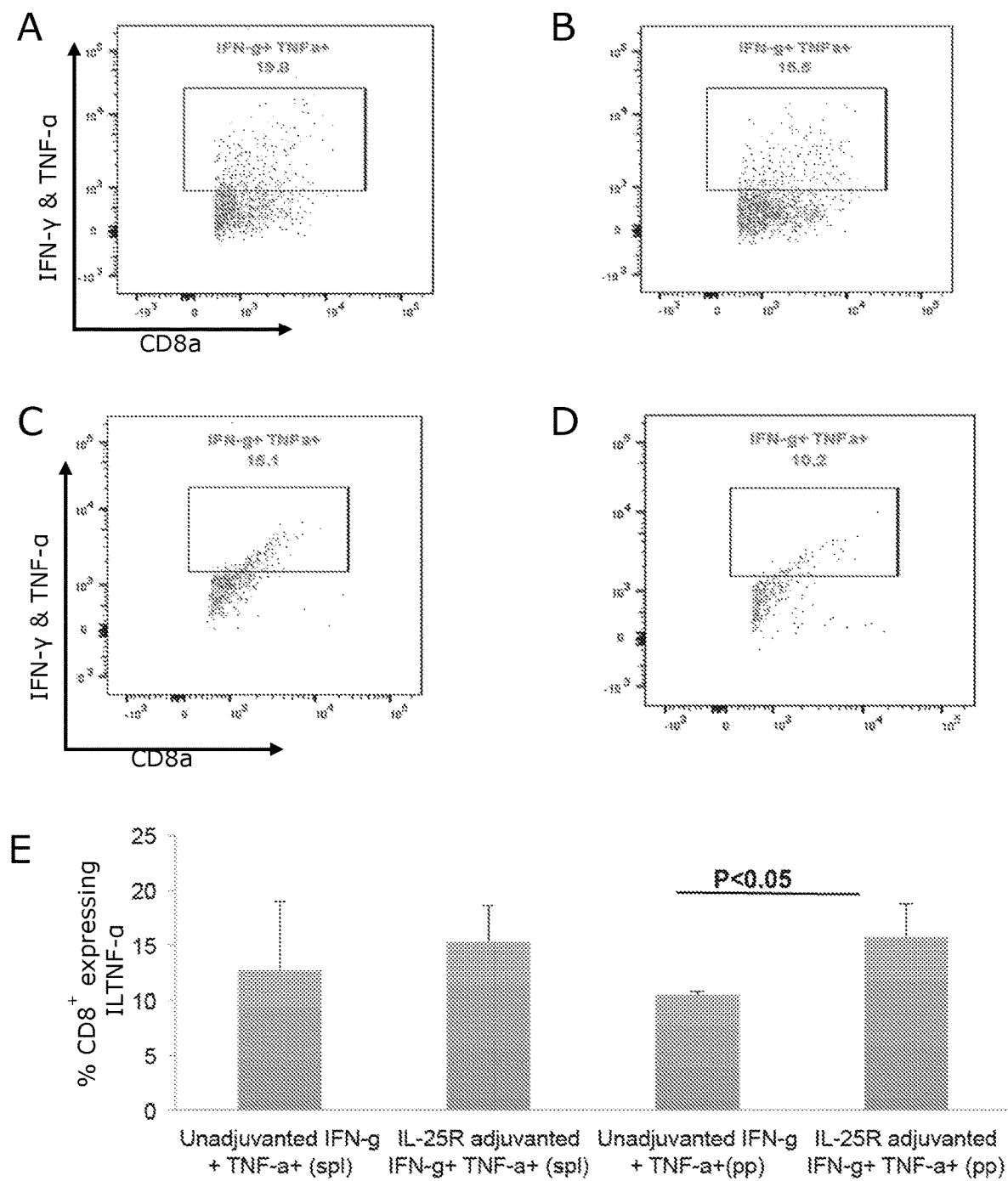
FIG. 12. Evaluation polyfunctional (IFN-γ and TNF-α) HIVgag-specific systemic (spleen; A, B) and mucosal (Peyer's Patch; C, D) CD8$^+$ T cells following i.n. FPV-HIV prime, followed by i.m. MVA-HIVgag-IL-25BP adjuvanted booster vaccination. Although no differences were detected in the systemic compartment, elevated numbers of polyfunctional HIV-gag specific CD8$^+$ cells were detected in Peyer's Patch relative to the control unadjuvanted i.n. FPV-HIV/i.m. MVA-HIV vaccination strategy (E). The plots represent cells gated on CD8$^+$ IFN-γ$^+$ T cells.

CD8$^+$ T cells were evaluated for polyfunctional (IFN-γ and TNF-α expression) following i.n. FPV-HIV/i.m. MVA-HIV-IL25BP prime-boost (FIG. 12). Although no differences were detected in the systemic (spleen) compartment comparing the vaccine strategies, elevated numbers of polyfunctional HIVgag specific CD8$^+$ cells were detected in Peyer's patch relative to the control unadjuvanted i.n. FPV-HIV/i.m. MVA-HIV vaccination strategy.

Transient inhibition of IL-25 signaling during muscle vaccination resulted in a highly significant enhancement of the IL-17A and IL-22 expression by ILC3-like cells.

Figure 13:
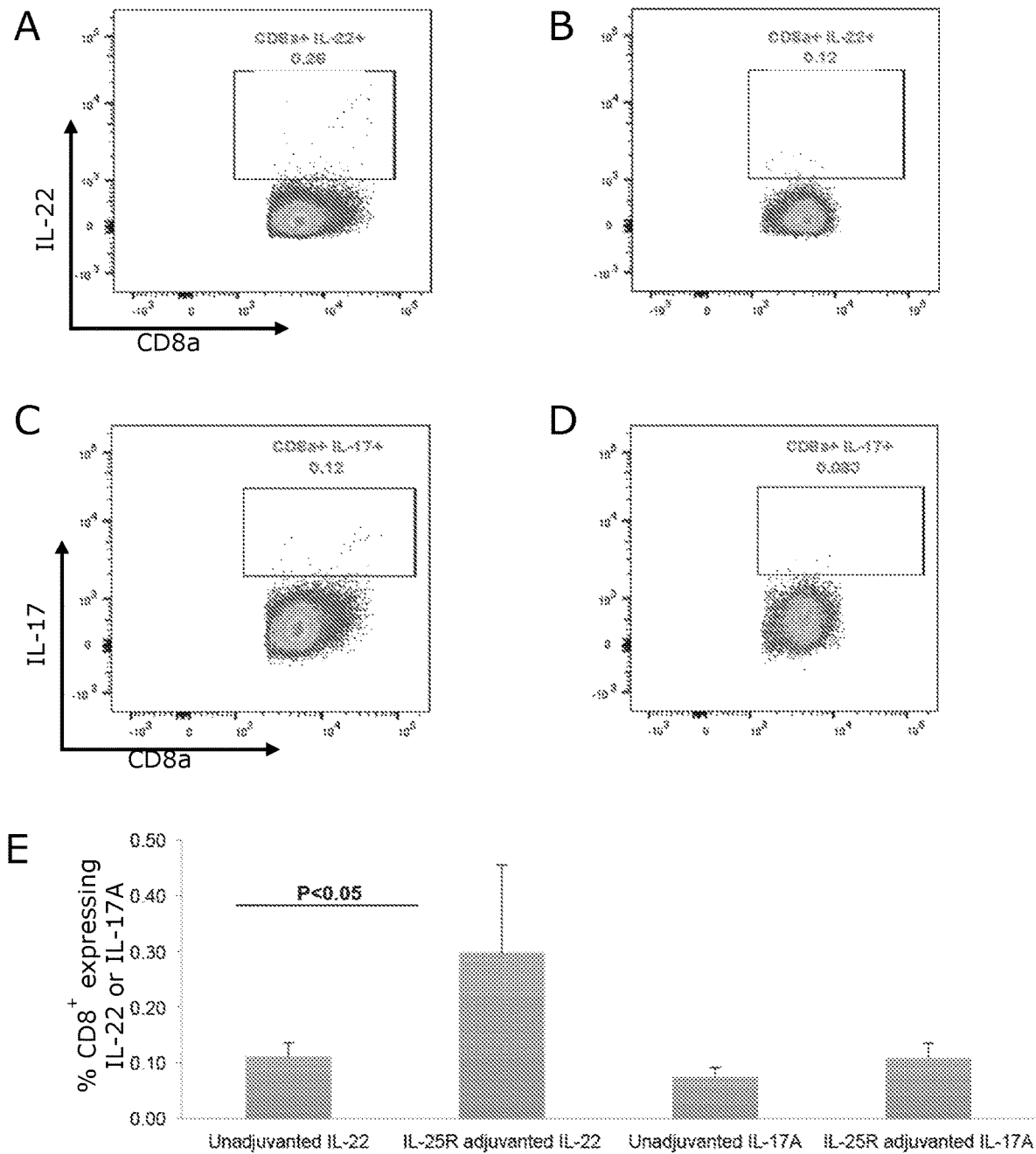
FIG. 13. Evaluation of IL-22 (A) and IL-17 (C) expressing HIVgag-specific systemic (spleen) CD8$^+$ T cells following i.n. FPV-HIV prime, followed by i.m. MVA-HIVgag-IL-25BP adjuvant booster vaccination. Although low compared to IFN-γ or TNF-α expression, elevated numbers of HIV-gag specific CD8$^+$ T cells that expressed IL-22 (A) and IL-17 (C) were detected in spleen (E) relative to the control unadjuvanted i.n. FPV-HIV/i.m. MVA-HIV vaccination strategy (unadjuvanted control data shown in B, D). The plots represent cells gated on CD8$^+$ T cells.

Evaluation of IL-17A and IL-22 expressing HIVgag-specific systemic (spleen) CD8$^+$ T cells following an i.n. FPV-HIV prime vaccination and an i.m. MVA-HIV-IL25BP booster vaccination is shown (FIG. 13). Elevated numbers of HIVgag specific CD8$^+$ T cells expressing IL-22 and IL-17A were detected in spleen relative to the control unadjuvanted vaccine strategy. However, this elevation was low compared to IFN-γ or TNF-α expression.

Figure 14:
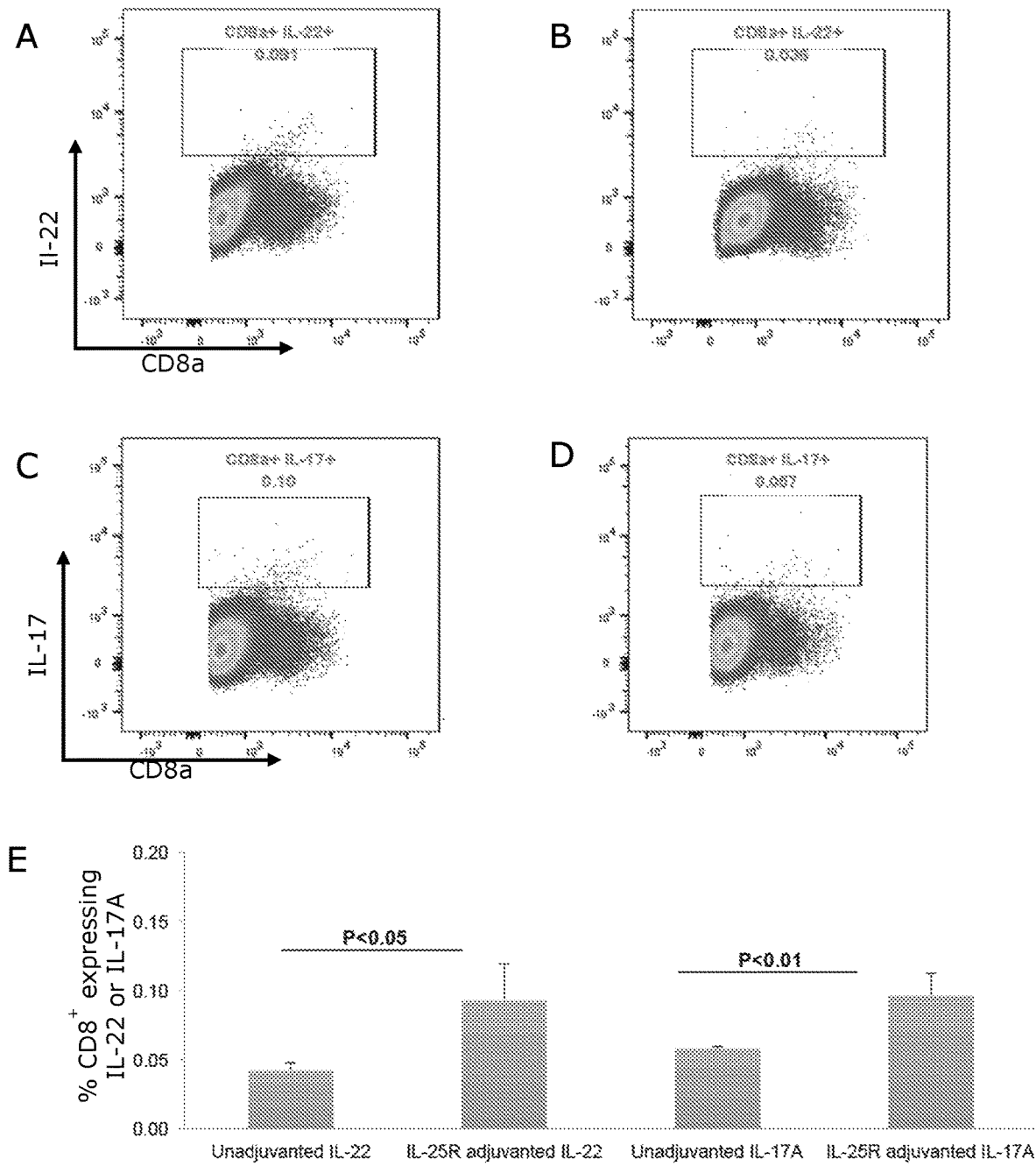
FIG. 14. Evaluation of IL-22 (A) and IL-17 (C) expressing HIVgag-specific mucosal (Peyer's Patch) CD8$^+$ T cells following i.n. FPV-HIV prime, followed by MVA-HIVgag-IL-25BP adjuvanted i.m. booster vaccination. Although low compared to IFN-γ or TNF-α expression, elevated numbers of HIV-gag specific CD8$^+$ T cells that expressed IL-22 (A) and IL-17-γ (C) were detected Peyer's Patches (E) relative to the control unadjuvanted i.n. FPV-HIV/i.m. MVA-HIV vaccination strategy (unadjuvanted control data shown in B, D). Note: The plots represent cells gated on CD8$^+$ T cells.
Figure 15:
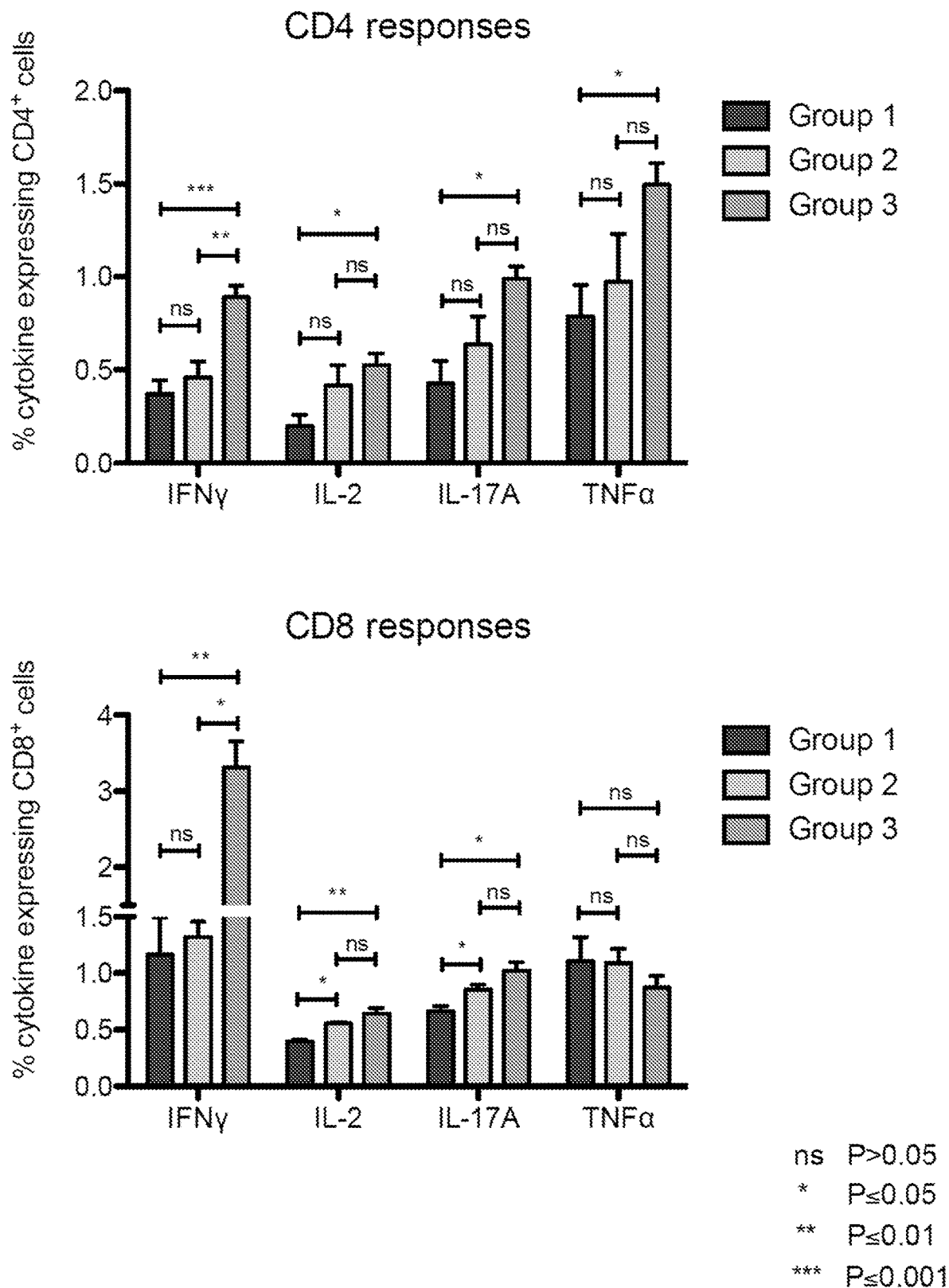
FIG. 15. Evaluation of cytokine expression by CD4$^+$ and CD8$^+$ T cells, following IL-25BP vaccination. WT BALB/c mice (n=5) were prime-boost immunized two weeks apart using intranasal/intramuscular vaccine strategy with; (1) FPV/MVA, (2) FPV-IL-25R/MVA-IL-25R and (3) FPV-IL-4R antagonist/MVA-IL-25R, expressing TB antigens and the expression of IFN-γ, IL-2, IL-17A and TNF-α by CD4$^+$ (top graph) and CD8$^+$ (bottom graph) T cells were evaluated 14 days post booster vaccination.
Figure 16:
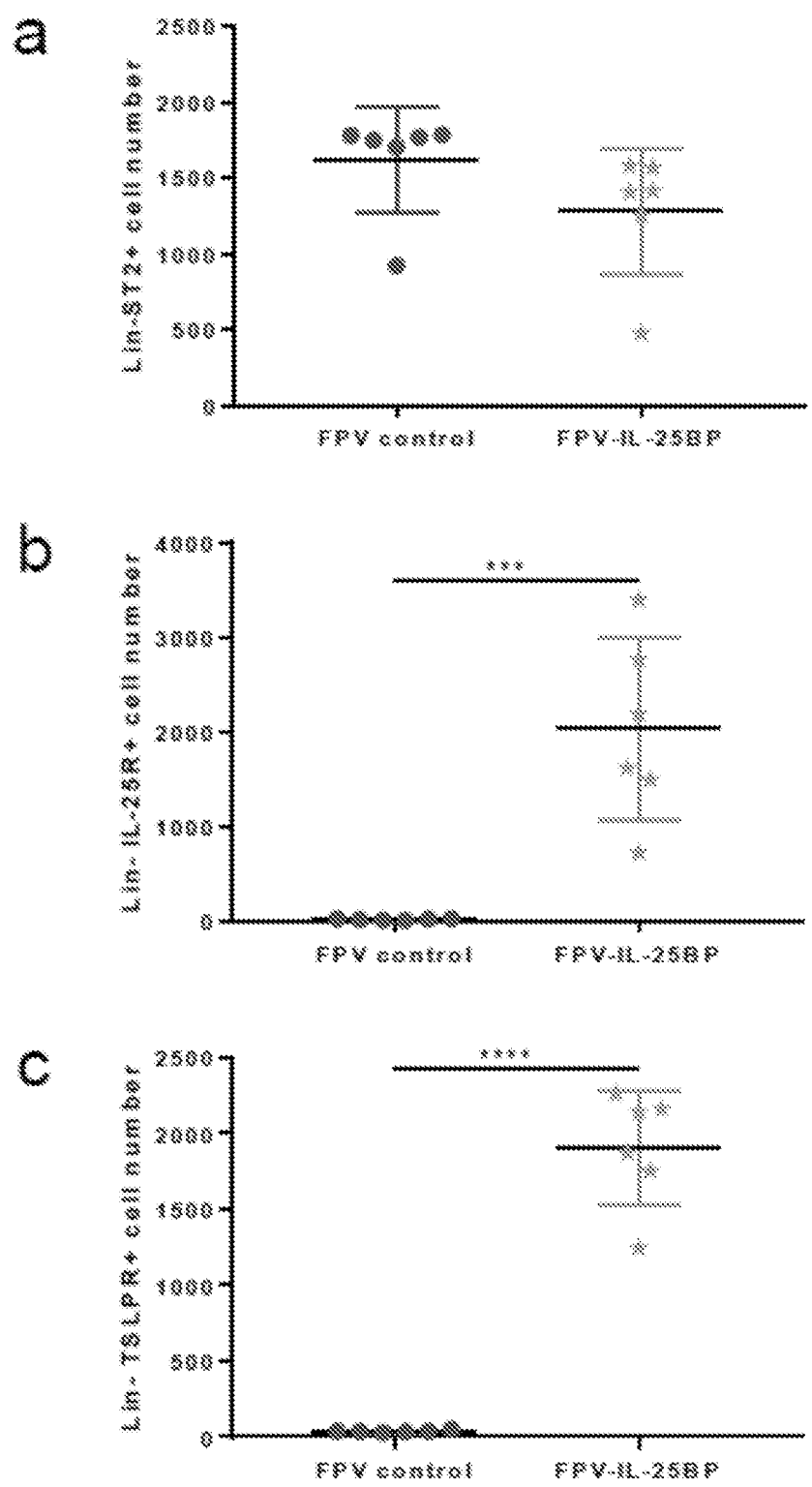
FIG. 16. Evaluation of lung lineage$^-$ ILC2 subsets 24 h post intranasal IL-25BP adjuvanted vaccination. WT BALB/c mice (n=6) were immunized intranasally with unadjuvanted or IL-25BP adjuvanted FPV vaccines and different ILC2 subsets were evaluated 24 h post vaccination. Graphs represents number of (a) lineage$^-$ IL-33R/ST2$^+$ ILC2s. (b) lineage$^-$ IL-33R/ST2$^-$ IL-25R$^+$ ILC2s (c) lineage$^-$ IL-33R/ST2$^-$ TSLPR$^+$ ILC2s back calculated to the CD45$^+$ population 24 h post vaccination. The error bars represent the mean and standard deviation (s.d.). The p-values were calculated using GraphPad Prism software (version 6.05 for Windows). *=p<0.05, =p<0.01, *=p<0.001, ****=p<0.0001.
Figure 17:
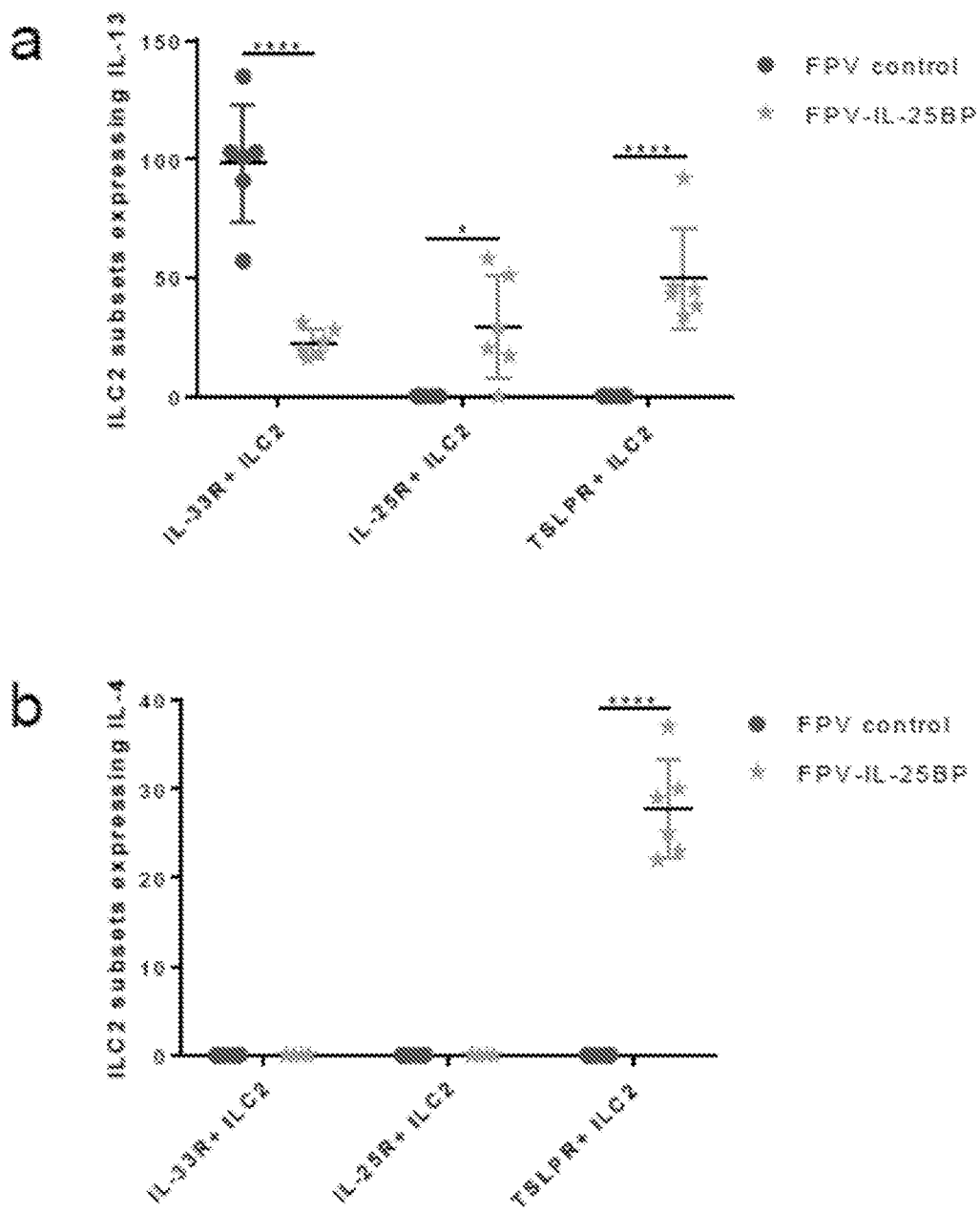
FIG. 17. Expression of IL-13 and IL-4 by different ILC2 subsets 24 h post intranasal IL-25BP adjuvanted vaccination. The three different ILC2 subsets were further analysed for IL-13 and IL-4 expression 24 h post vaccination. The graphs represent (a) IL-13 and (b) IL-4 expression by the different ILC2 subsets. The error bars represent the mean and standard deviation (s.d.). The p-values were calculated using GraphPad Prism software (version 6.05 for Windows). *=p<0.05, =p<0.01, *=p<0.001, ****=p<0.0001.
Figure 18:
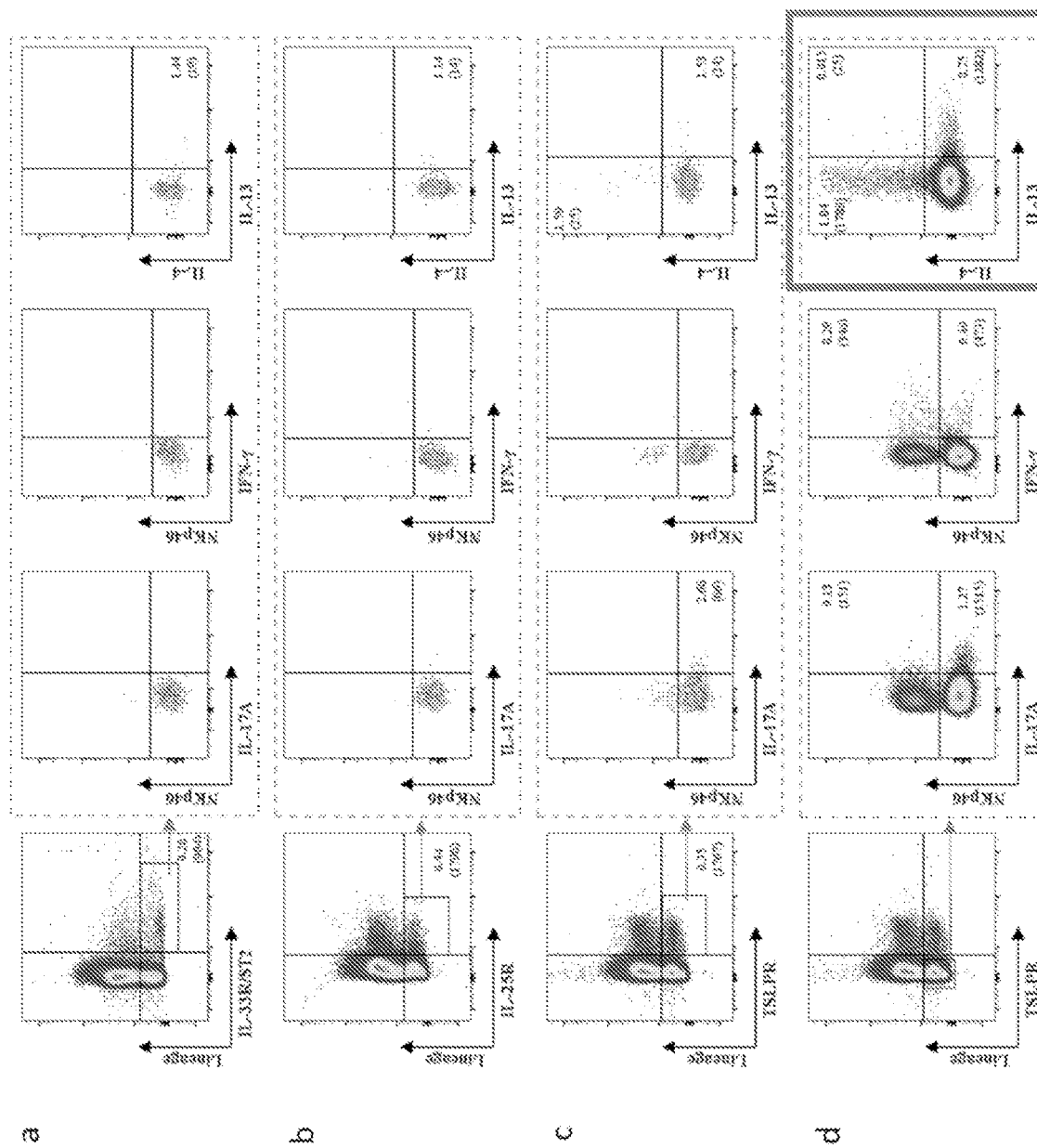
FIG. 18. Expression of IL-13 and IL-4 by lineage$^-$ IL-33R/ST2$^-$ IL-25R$^-$ TSLPR$^-$ (novel) ILC2 subset 24 h post intranasal IL-25BP adjuvanted FPV vaccination. 24 h post intranasal IL-25BP adjuvanted FPV vaccination, the expression of IL-4 and IL-13 by different ILC2 subsets were assessed. The FACS plots represent (a) lineage$^-$ IL-33R/ST2$^+$ ILC2, (b) lineage$^-$ IL-33R/ST2$^-$ IL-25R$^+$ ILC2 (c) lineage$^-$ IL-33R/ST2$^-$ TSLPR$^+$ ILC2 and (d) the novel lineage$^-$ IL-33R/ST2$^-$ IL-25R-TSLPR$^-$ ILC2 expressing IL-13 and IL-4 (bottom right plot).
Figure 19:
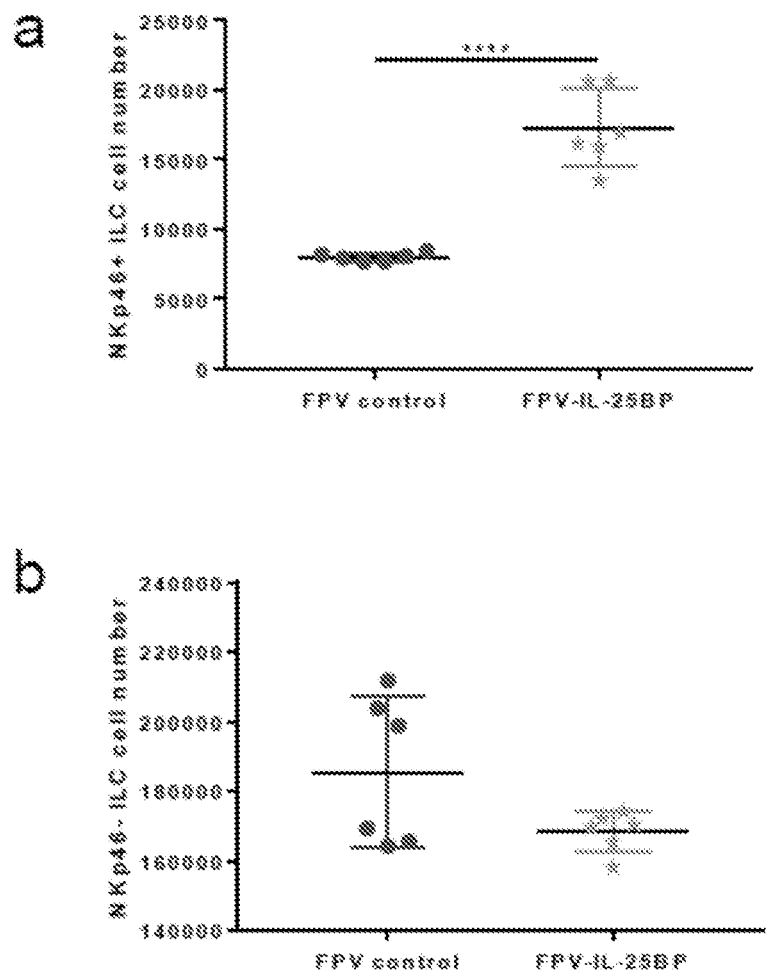
FIG. 19. Identification of lung lineage$^-$ IL-33R/ST2$^-$ NKp46$^{+/-}$ ILC (ILC1&3) subsets 24 h post intranasal IL-25BP adjuvanted vaccination. WT BALB/c mice (n=6) were immunized intranasally with unadjuvanted and IL-25BP adjuvanted FPV vaccines. The graphs represent number of (a) lineage$^-$ IL-33R/ST2$^-$ NKp46$^+$ ILC and (b) lineage$^-$ IL-33R/ST2$^-$ NKp46$^-$ ILC back calculated to CD45$^+$ cells, 24 h post vaccination. The error bars represent the mean and standard deviation (s.d.). The p-values were calculated using GraphPad Prism software (version 6.05 for Windows). *=p<0.05, =p<0.01, *=p<0.001, ****=p<0.0001.
Figure 20:
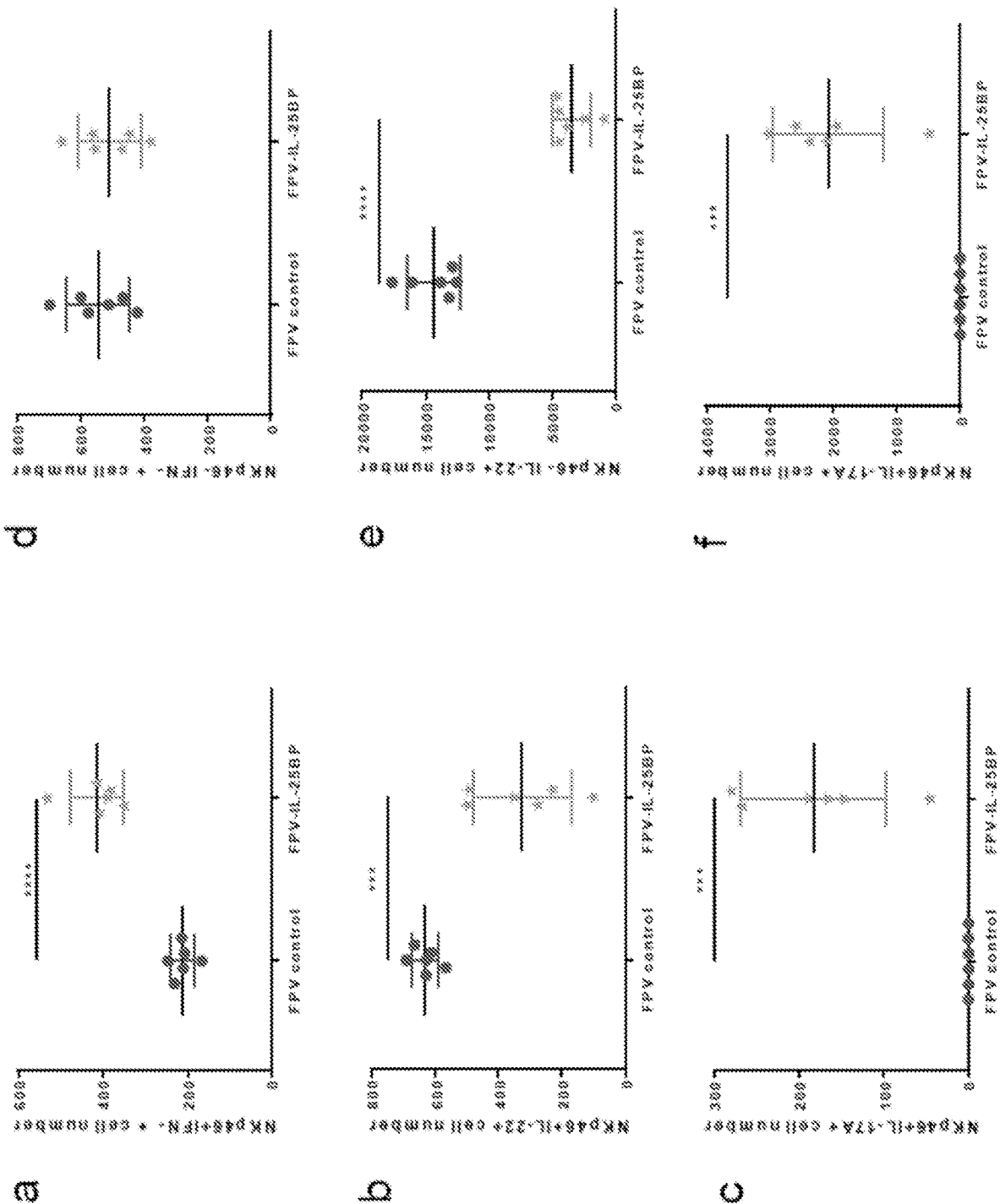
FIG. 20. Evaluation of IFN-γ, IL-22 and IL-17A expression by lineage$^-$ IL-33R/ST2$^-$ NKp46$^+$ and NKp46$^-$ ILC following intranasally IL-25BP adjuvanted FPV vaccination. The graphs indicate the number of NKp46$^+$ and NKp46$^-$ ILC expressing (a and d) IFN-γ, (b and e) IL-22 and (c and f) IL-17A respectively, 24 h post unadjuvanted and IL-256P adjuvanted FPV vaccination. The error bars represent the mean and standard deviation (s.d.). The p-values were calculated using GraphPad Prism software (version 6.05 for Windows). *=p<0.05, =p<0.01, *=p<0.001, ****=p<0.0001.

FIG. 14 provides a clear evaluation of IL-17A and IL-22 expressing HIVgag-specific CD8$^+$ T cells in Peyer's patch following FPV-HIV i.n. prime and i.m. MVA-HIV-IL25BP boost vaccination. Although low compared to IFN-γ and TNF-α expression, elevated numbers of HIVgag-specific CD8$^+$ T cells expressed IL-22 and IL-17A were detected in Peyer's patches relative to the control unadjuvanted vaccination.

In summary, providing a soluble inhibitor for IL-25 during the intramuscular boost vaccination resulted in elevated HIVgag-specific CD8$^+$ T cell response in both the systemic and mucosal immune compartments, with enhanced numbers IFN-γ TNF-α, IL-22 and IL-17A expressing T cells, importantly in the mucosae where pathogens are first encountered. The ability to enhance both Th1 and Th17 mediated response at mucosal surfaces would be beneficial for many vaccines, particularly for immunity for pulmonary tuberculosis where it is recognised CD4$^+$ T cell expression of IFN-γ and IL-17A is required for effective immunity.

The IL-256P i.m. boost could be also used in conjunction with an IL-4R antagonist. Providing the IL-4R antagonist in the i.n. prime vaccination should enhance Th1 mediated immunity with increased antigen-specific CD8$^+$ T avidity and poly-functional cytokine expression (IFN-γ, TNF-α, IL-2) (see, Jackson, 2014b, supra). An i.m. boost including an inhibitor of IL-25 function, such as IL-256P adjuvant, could be used to enhance antigen specific IL-17A/IL-22 T cell responses, providing combined enhanced Th1 and Th17 mediated responses in both mucosal and systemic compartments.

These results indicate that IL-13 expressed by ILC2 negatively regulates Th1 mediated anti-viral CD8$^+$ T cell immunity, while also positively (possibly via an alternative IL-13 receptor) and negatively (via IL-4Rα/IL13Rα1 STATE signaling) influencing ILC1 IFN-γ expression and antibody immunity by an uncharacterized mechanism.

These studies indicate there are complex interactions between ILC and antigen presenting cells (APC, dendritic cells and macrophages) with the cytokines expressed by ILC influencing APC activation and development of adaptive CD4$^+$ T helper cells, CD8$^+$ cytotoxic T cells, and B cells and antibody expression.

Discussion

It is proposed that a recombinant vaccine co-expressing an antigen and an IL-25 inhibitor (such as IL-256P) will be able to elicit T cells with higher avidity to antigens and a capacity to protect against a pathogenic challenge. Thus, the co-expression of an antigen and a soluble IL-25 antagonist in a recombinant vaccine will be able to dramatically enhance T cell avidity elicited to vaccine antigens and afford a higher level of protection against challenge.

It is considered that the vector of the vaccine will enter cells of the host, some of which will be antigen-presenting cells of the immune system, which will express both the antigen and the IL-25 antagonist. The antigen is processed by the cell so as to stimulate an immune response specific for the antigen, while the IL-25 antagonist leaves the cell and binds to host IL-25 that is produced during the immune response. The expression of both the antigen and IL-25 antagonist occurs in the local milieu of the immune response. The present inventors propose that production of both the antigen and IL-25 antagonist in the local milieu of the immune response may be an essential requirement for the desired immune response (production of high avidity CD8$^+$ T cells). It is further proposed that the delivery of the antigen and IL-25 antagonist separately fails to induce appropriate responses. In the recombinant vaccine of the present invention, the IL-25 antagonist binds and therefore detracts host IL-25 from its negative effect on the immune response resulting in heightened T cells responses with increased avidity towards the antigen. The T cells elicited under this regime also have markedly broadened cytokine profile responses different from that induced without the IL-25 antagonist.

Accordingly, it is considered that such vaccines will be useful in providing improved immunity to the recipient as they inhibit the development of detrimental Th2 host responses.

Example 2

Prime-Boost Vaccination Study—Evaluation of CD4$^+$ and CD8$^+$ T Cell Immunity

WT BALB/c mice were prime-boost immunized two weeks apart using intranasal/intramuscular (i.n./i.m.) vaccine strategy with; (1) rFPV $1\times10^7$ PFU/rMVA $2\times10^7$ PFU, (2) rFPV-IL-25BP $1\times10^7$ PFU/rMVA-IL-25BP $2\times10^7$ PFU and (3) rFPV-IL-4R antagonist $1\times10^7$ PFU/rMVA-IL-25BP $2\times10^7$ PFU, expressing TB antigens. These constructs were prepared using analogous protocols to those described in Example 1. $CD4^+$ and $CD8^+$ T cell immune responses were evaluated 14 days post booster immunization.

Data from this study revealed the following:

Similar to the HIV vaccine studies, although no differences in cytokine production by $CD4^+$ or $CD8^+$ T cells were observed in spleen (systemic compartment) following IL-25BP vaccination, significant differences were observed in lung and the mucosal compartment (FIG. 15);

IL-25BP adjuvant vaccine given i.m. can manipulate the ILC at the vaccination site (muscle), and help recruit unique antigen-presenting cells that imprint T cells home to the mucosae. Accordingly, the present inventors propose that co-administration of a IL-25 inhibitor and an antigen that corresponds to a target antigen via a systemic route will enhance mucosal immunity to the target antigen.

Based on these results, the present inventors propose that i.m./i.m. delivery of IL-25R antagonist will generate long lasting mucosal immunity. This would be of great value given the safety associated with i.m. delivery compared to i.n. delivery.

IL-4R antagonist adjuvant prime followed by IL-25BP adjuvant booster induced highly multi-functional $CD4^+$ and $CD8^+$ T cells expressing IFN-γ, IL-2 and IL-17A compared to strategies 1 and 2 above. (production of these cytokines is a hallmark of protective efficacy against both HIV and TB).

Furthermore, following i.n. rFPV-L-4R antagonist/i.m. rMVA-IL-25BP prime-boost strategy, the ability to produce IL-17A by $CD4^+$ and $CD8^+$ T cells appeared to be superior to i.n./i.m. IL-4R antagonist adjuvanted (alone) prime-boost vaccination strategy.

Example 3

Intranasal Delivery of IL-25BP—ILC Study

When rFPV co-expressing IL-25BP was given i.n. ($1\times10^7$ PFU) to BALB/c mice, other than the lung resident IL-33R$^+$ ILC2, unexpected IL-25R$^+$ ILC2 and TSLPR$^+$ ILC2 populations were detected compared to unadjuvanted rFPV vaccination (see, FIG. 16).

Unlike i.m. delivery, when IL-25BP was given i.n. although it inhibited IL-13 production by lung resident IL-33R$^+$ ILC2, it also unexpectedly enhanced IL-13 expression by IL-25R$^+$ ILC2 and also IL-4 and IL-13 expression by TSLPR$^+$ ILC2, and also a new ILC2 subset (interestingly, the latter three types of ILC2 have not been detected in the lung following unadjuvanted rFPV vaccination) (FIGS. 16 and 17).

The new ILC2 subset (IL-33R$^-$ IL-25R$^-$ TSLPR$^-$ ILC2) was shown to induce elevated IL-4 and IL-13 compared to any of the other three LC2 subsets (FIG. **18*d* far right).

Furthermore, IL-256P adjuvanted rFPV vaccination was shown to enhance the NKP46+ ILC1 and 3 numbers (FIG. 19), including their expression of IFN-γ and IL-17A (FIG. 20) compared to unadjuvanted vaccination.

In conclusion, the results of this study indicate that delivery of IL-256P should be performed suitably by a route other than a mucosal route (e.g., other than i.n.) and preferably by a systemic route of administration (e.g., i.m.) to block IL-25R$^+$ ILC2 expressing IL-13 in muscle but not i.n to manipulate lung ILC2.

The disclosure of every patent, patent application, and publication cited herein is hereby incorporated herein by reference in its entirety.

The citation of any reference herein should not be construed as an admission that such reference is available as “Prior Art” to the instant application.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

The invention claimed is:

1. An immunostimulatory composition comprising a first agent comprising an immune stimulator or a polynucleotide sequence from which a nucleotide sequence encoding an immune stimulator is expressible, wherein the immune stimulator stimulates or otherwise enhances an immune response to a target antigen in a subject, co-expressed with a second agent comprising an inhibitor of IL-25 function or a polynucleotide from which a nucleotide sequence encoding an inhibitor of IL-25 function is expressible, wherein the first agent comprises a human immunodeficiency virus (HIV) antigen or tuberculosis (TB) antigen, and wherein the second agent comprises IL-25 binding protein.

2. The composition of claim 1, wherein the composition comprises a nucleic acid composition comprising: a first agent comprising a coding sequence for an immune stimulator operably linked to a regulatory polynucleotide, wherein the immune stimulator stimulates or otherwise enhances an immune response to a target antigen in a subject; and a second agent comprising a coding sequence for an inhibitor of IL-25 function operably linked to a regulatory polynucleotide.

3. The composition of claim 2, wherein the first agent and the second agent are in the form of one or more nucleic acid constructs.

4. The composition of claim 1, wherein the first agent and the second agent are in the form of a single composition.

5. The composition of claim 1, wherein the composition is formulated for intramuscular injection.

6. The composition of claim 1, wherein the target antigen is derived from a pathogenic organism.

7. The composition of claim 6, wherein the pathogenic organism is a virus or bacteria.

8. The composition of claim 7, wherein the virus is human immunodeficiency virus (HIV).

9. The composition of claim 8, wherein the HIV antigen is selected from any one of the gene product of the gag, pol, or env genes, the Nef protein, and reverse transcriptase.

10. The composition of claim 7, wherein the bacteria is selected from *Mycobacterium tuberculosis* (TB), *M. bovis*, and *M. avium paratuberculosis*.

11. A kit comprising a priming composition comprising a first agent comprising an immune stimulator or a polynucleotide from which a nucleotide sequence encoding an immune stimulator is expressible, wherein the immune stimulator stimulates or otherwise enhances an immune response to a target antigen in a subject, and a boosting composition comprising the immune stimulator together with a second agent comprising an inhibitor of IL-25 function or a polynucleotide from which a nucleotide sequence encoding an inhibitor of IL-25 function is expressible, wherein the first agent comprises an HIV antigen or TB antigen, and wherein the second agent comprises IL-25 binding protein.

12. The kit of claim 11, wherein the priming composition further comprises an inhibitor of IL-4 function or a polynucleotide from which a nucleotide sequence encoding an inhibitor of IL-4 function is expressible, wherein the inhibitor of IL-4 function is an IL-4C123 polypeptide.

13. The kit of claim 12, wherein the priming composition is in the form of a single composition.

14. The kit of claim 11, wherein the boosting composition is in the form of a single composition.

* * * * *

SEQUENCE LISTING

```
<160> NUMBER OF SEQ ID NOS: 115

<210> SEQ ID NO 1
<211> LENGTH: 866
<212> TYPE: PRT
<213> ORGANISM: Homo sapiens

<400> SEQUENCE: 1

Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
            20                  25                  30

Leu Arg Leu Leu Asp His Arg Ala Leu Val Cys Ser Gln Pro Gly Leu
        35                  40                  45

Asn Cys Thr Val Lys Asn Ser Thr Cys Leu Asp Asp Ser Trp Ile His
    50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95
```

```
Glu Trp Thr Leu Gln Thr Asp Ala Ser Ile Leu Tyr Leu Glu Gly Ala
                100                 105                 110

Glu Leu Ser Val Leu Gln Leu Asn Thr Asn Glu Arg Leu Cys Val Arg
            115                 120                 125

Phe Glu Phe Leu Ser Lys Leu Arg His His Arg Arg Trp Arg Phe
130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
        195                 200                 205

Val Glu Thr Leu Glu Ala His Gln Leu Arg Val Ser Phe Thr Leu Trp
    210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
            260                 265                 270

Leu Lys Gly Cys Cys Arg His Gln Val Gln Ile Gln Pro Phe Phe Ser
        275                 280                 285

Ser Cys Leu Asn Asp Cys Leu Arg His Ser Ala Thr Val Ser Cys Pro
    290                 295                 300

Glu Met Pro Asp Thr Pro Glu Pro Ile Pro Asp Tyr Met Pro Leu Trp
305                 310                 315                 320

Val Tyr Trp Phe Ile Thr Gly Ile Ser Ile Leu Leu Val Gly Ser Val
                325                 330                 335

Ile Leu Leu Ile Val Cys Met Thr Trp Arg Leu Ala Gly Pro Gly Ser
            340                 345                 350

Glu Lys Tyr Ser Asp Asp Thr Lys Tyr Thr Asp Gly Leu Pro Ala Ala
        355                 360                 365

Asp Leu Ile Pro Pro Leu Lys Pro Arg Lys Val Trp Ile Ile Tyr
    370                 375                 380

Ser Ala Asp His Pro Leu Tyr Val Asp Val Leu Lys Phe Ala Gln
385                 390                 395                 400

Phe Leu Leu Thr Ala Cys Gly Thr Glu Val Ala Leu Asp Leu Leu Glu
                405                 410                 415

Glu Gln Ala Ile Ser Glu Ala Gly Val Met Thr Trp Val Gly Arg Gln
            420                 425                 430

Lys Gln Glu Met Val Glu Ser Asn Ser Lys Ile Ile Val Leu Cys Ser
        435                 440                 445

Arg Gly Thr Arg Ala Lys Trp Gln Ala Leu Leu Gly Arg Gly Ala Pro
    450                 455                 460

Val Arg Leu Arg Cys Asp His Gly Lys Pro Val Gly Asp Leu Phe Thr
465                 470                 475                 480

Ala Ala Met Asn Met Ile Leu Pro Asp Phe Lys Arg Pro Ala Cys Phe
                485                 490                 495

Gly Thr Tyr Val Val Cys Tyr Phe Ser Glu Val Ser Cys Asp Gly Asp
            500                 505                 510
```

```
Val Pro Asp Leu Phe Gly Ala Ala Pro Arg Tyr Pro Leu Met Asp Arg
        515                 520                 525

Phe Glu Glu Val Tyr Phe Arg Ile Gln Asp Leu Glu Met Phe Gln Pro
    530                 535                 540

Gly Arg Met His Arg Val Gly Glu Leu Ser Gly Asp Asn Tyr Leu Arg
545                 550                 555                 560

Ser Pro Gly Gly Arg Gln Leu Arg Ala Ala Leu Asp Arg Phe Arg Asp
                565                 570                 575

Trp Gln Val Arg Cys Pro Asp Trp Phe Glu Cys Glu Asn Leu Tyr Ser
            580                 585                 590

Ala Asp Asp Gln Asp Ala Pro Ser Leu Asp Glu Val Phe Glu Glu
        595                 600                 605

Pro Leu Leu Pro Pro Gly Thr Gly Ile Val Lys Arg Ala Pro Leu Val
        610                 615                 620

Arg Glu Pro Gly Ser Gln Ala Cys Leu Ala Ile Asp Pro Leu Val Gly
625                 630                 635                 640

Glu Glu Gly Gly Ala Ala Val Ala Lys Leu Glu Pro His Leu Gln Pro
                645                 650                 655

Arg Gly Gln Pro Ala Pro Gln Pro Leu His Thr Leu Val Leu Ala Ala
                660                 665                 670

Glu Glu Gly Ala Leu Val Ala Ala Val Glu Pro Gly Pro Leu Ala Asp
            675                 680                 685

Gly Ala Ala Val Arg Leu Ala Leu Ala Gly Glu Gly Glu Ala Cys Pro
        690                 695                 700

Leu Leu Gly Ser Pro Gly Ala Gly Arg Asn Ser Val Leu Phe Leu Pro
705                 710                 715                 720

Val Asp Pro Glu Asp Ser Pro Leu Gly Ser Ser Thr Pro Met Ala Ser
                725                 730                 735

Pro Asp Leu Leu Pro Glu Asp Val Arg Glu His Leu Glu Gly Leu Met
            740                 745                 750

Leu Ser Leu Phe Glu Gln Ser Leu Ser Cys Gln Ala Gln Gly Gly Cys
        755                 760                 765

Ser Arg Pro Ala Met Val Leu Thr Asp Pro His Thr Pro Tyr Glu Glu
770                 775                 780

Glu Gln Arg Gln Ser Val Gln Ser Asp Gln Gly Tyr Ile Ser Arg Ser
785                 790                 795                 800

Ser Pro Gln Pro Pro Glu Gly Leu Thr Glu Met Glu Glu Glu Glu
                805                 810                 815

Glu Glu Gln Asp Pro Gly Lys Pro Ala Leu Pro Leu Ser Pro Glu Asp
                820                 825                 830

Leu Glu Ser Leu Arg Ser Leu Gln Arg Gln Leu Leu Phe Arg Gln Leu
        835                 840                 845

Gln Lys Asn Ser Gly Trp Asp Thr Met Gly Ser Glu Ser Glu Gly Pro
        850                 855                 860

Ser Ala
865

<210> SEQ ID NO 2
<211> LENGTH: 502
<212> TYPE: PRT
<213> ORGANISM: Homo sapiens
```

<400> SEQUENCE: 2

```
Met Ser Leu Val Leu Leu Ser Leu Ala Ala Leu Cys Arg Ser Ala Val
1               5                   10                  15

Pro Arg Glu Pro Thr Val Gln Cys Gly Ser Glu Thr Gly Pro Ser Pro
            20                  25                  30

Glu Trp Met Leu Gln His Asp Leu Ile Pro Gly Asp Leu Arg Asp Leu
        35                  40                  45

Arg Val Glu Pro Val Thr Thr Ser Val Ala Thr Gly Asp Tyr Ser Ile
    50                  55                  60

Leu Met Asn Val Ser Trp Val Leu Arg Ala Asp Ala Ser Ile Arg Leu
65                  70                  75                  80

Leu Lys Ala Thr Lys Ile Cys Val Thr Gly Lys Ser Asn Phe Gln Ser
                85                  90                  95

Tyr Ser Cys Val Arg Cys Asn Tyr Thr Glu Ala Phe Gln Thr Gln Thr
            100                 105                 110

Arg Pro Ser Gly Gly Lys Trp Thr Phe Ser Tyr Ile Gly Phe Pro Val
        115                 120                 125

Glu Leu Asn Thr Val Tyr Phe Ile Gly Ala His Asn Ile Pro Asn Ala
130                 135                 140

Asn Met Asn Glu Asp Gly Pro Ser Met Ser Val Asn Phe Thr Ser Pro
145                 150                 155                 160

Gly Cys Leu Asp His Ile Met Lys Tyr Lys Lys Cys Val Lys Ala
                165                 170                 175

Gly Ser Leu Trp Asp Pro Asn Ile Thr Ala Cys Lys Lys Asn Glu Glu
            180                 185                 190

Thr Val Glu Val Asn Phe Thr Thr Thr Pro Leu Gly Asn Arg Tyr Met
        195                 200                 205

Ala Leu Ile Gln His Ser Thr Ile Ile Gly Phe Ser Gln Val Phe Glu
    210                 215                 220

Pro His Gln Lys Lys Gln Thr Arg Ala Ser Val Val Ile Pro Val Thr
225                 230                 235                 240

Gly Asp Ser Glu Gly Ala Thr Val Gln Leu Thr Pro Tyr Phe Pro Thr
                245                 250                 255

Cys Gly Ser Asp Cys Ile Arg His Lys Gly Thr Val Val Leu Cys Pro
            260                 265                 270

Gln Thr Gly Val Pro Phe Pro Leu Asp Asn Asn Lys Ser Lys Pro Gly
        275                 280                 285

Gly Trp Leu Pro Leu Leu Leu Ser Leu Leu Val Ala Thr Trp Val
290                 295                 300

Leu Val Ala Gly Ile Tyr Leu Met Trp Arg His Glu Arg Ile Lys Lys
305                 310                 315                 320

Thr Ser Phe Ser Thr Thr Thr Leu Leu Pro Pro Ile Lys Val Leu Val
                325                 330                 335

Val Tyr Pro Ser Glu Ile Cys Phe His His Thr Ile Cys Tyr Phe Thr
            340                 345                 350

Glu Phe Leu Gln Asn His Cys Arg Ser Glu Val Ile Leu Glu Lys Trp
        355                 360                 365

Gln Lys Lys Lys Ile Ala Glu Met Gly Pro Val Gln Trp Leu Ala Thr
    370                 375                 380

Gln Lys Lys Ala Ala Asp Lys Val Val Phe Leu Leu Ser Asn Asp Val
385                 390                 395                 400

Asn Ser Val Cys Asp Gly Thr Cys Gly Lys Ser Glu Gly Ser Pro Ser
                405                 410                 415
```

```
Glu Asn Ser Gln Asp Leu Phe Pro Leu Ala Phe Asn Leu Phe Cys Ser
            420                 425                 430

Asp Leu Arg Ser Gln Ile His Leu His Lys Tyr Val Val Tyr Phe
            435                 440                 445

Arg Glu Ile Asp Thr Lys Asp Asp Tyr Asn Ala Leu Ser Val Cys Pro
450                 455                 460

Lys Tyr His Leu Met Lys Asp Ala Thr Ala Phe Cys Ala Glu Leu Leu
465                 470                 475                 480

His Val Lys Gln Gln Val Ser Ala Gly Lys Arg Ser Gln Ala Cys His
            485                 490                 495

Asp Gly Cys Cys Ser Leu
            500

<210> SEQ ID NO 3
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Ser Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
            85                  90                  95

Ala Arg Arg Gln Leu Tyr Phe Asp Tyr Trp Gly Gln Gly Thr Leu Val
            100                 105                 110

Thr Val Ser Ser
        115

<210> SEQ ID NO 4
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Val Gln Leu Val Gln Ser Gly Ala Glu Val Lys Lys Pro Gly Ala
1               5                   10                  15

Ala Val Lys Val Ser Cys Lys Ala Thr Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Asn Thr Lys Tyr Ala Gln Lys Leu
    50                  55                  60

Gln Gly Arg Val Thr Met Thr Thr Asp Thr Ser Thr Ser Thr Ala Tyr
65                  70                  75                  80
```

-continued

```
Met Glu Leu Arg Ser Leu Arg Ser Asp Asp Thr Ala Val Tyr Tyr Cys
                85                  90                  95

Ala Arg Lys Gln Leu Val Phe Asp Tyr Trp Gly Gln Gly Thr Leu Val
            100                 105                 110

Thr Val Ser Ser
        115

<210> SEQ ID NO 5
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Asn Thr Lys Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Gln Leu Ala Leu Asp Tyr Trp Gly Gln Gly Thr Leu Val
            100                 105                 110

Thr Val Ser Ser
        115

<210> SEQ ID NO 6
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Gln Leu Tyr Phe Asp Tyr Trp Gly Gln Gly Thr Leu Val
            100                 105                 110

Thr Val Ser Ser
        115
```

```
<210> SEQ ID NO 7
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Arg Leu Glu Trp Ile
        35                  40                  45

Gly Arg Ile Tyr Pro Ser Gly Arg Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Ala Tyr Glu Leu Gln Leu Gly Leu Tyr Tyr Tyr Tyr Gly Met
            100                 105                 110

Asp Val Trp Gly Gln Gly Thr Pro Val Thr Val Ser Ser
        115                 120                 125

<210> SEQ ID NO 8
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Ala Ala Gly Lys Arg Leu Glu Trp Ile
        35                  40                  45

Gly Arg Ile Tyr Pro Ser Gly Arg Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Ala Tyr Glu Leu Gln Leu Gly Leu Tyr Tyr Tyr Tyr Gly Met
            100                 105                 110

Asp Val Trp Gly Gln Gly Thr Pro Val Thr Val Ser Ser
        115                 120                 125

<210> SEQ ID NO 9
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 9

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Phe Gln Gln Lys Pro Gly Gln Ala Pro Arg Pro Leu Ile
        35                  40                  45

Tyr Asp Ala Ser Thr Arg Ala Thr Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asp Asn Trp Pro Leu
                85                  90                  95

Thr Phe Gly Gly Gly Thr Lys Val Glu Ile Lys
            100                 105

<210> SEQ ID NO 10
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Ser Cys Gln Gln Tyr Asp Asn Trp Pro Leu
                85                  90                  95

Thr Phe Gly Gly Gly Thr Lys Val Glu Ile Lys
            100                 105

<210> SEQ ID NO 11
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Asp
    50                  55                  60

```
Asn Gly Ser Gly Thr Glu Phe Thr Leu Thr Ile Ser Ser Leu Gln Ser
 65                  70                  75                  80

Glu Asp Phe Ala Val Tyr Phe Cys Gln Gln Tyr Asp Thr Trp Pro Leu
                 85                  90                  95

Thr Phe Gly Gly Gly Thr Lys Val Glu Ile Lys
                100                 105

<210> SEQ ID NO 12
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Ile Val Met Thr Gln Ser Pro Ala Thr Leu Ser Val Ser Pro Gly
 1               5                  10                  15

Glu Arg Val Thr Leu Ser Cys Arg Ala Ser Gln Ser Val Ser Ser Asn
                 20                  25                  30

Leu Ala Trp Phe Gln Gln Lys Pro Gly Gln Ala Pro Arg Pro Leu Ile
             35                  40                  45

Tyr Asp Ala Ser Thr Arg Ala Ala Gly Ile Pro Ala Arg Phe Ser Gly
 50                  55                  60

Ser Gly Ser Gly Thr Asp Phe Thr Leu Thr Ile Ser Ser Leu Gln Ser
 65                  70                  75                  80

Glu Asp Phe Ala Val Tyr Tyr Cys Gln Gln Tyr Asp Asn Trp Pro Leu
                 85                  90                  95

Thr Phe Gly Gly Gly Thr Lys Val Glu Ile Lys
                100                 105

<210> SEQ ID NO 13
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ile Gln Met Thr Gln Ser Pro Ser Ser Leu Ser Ala Ser Val Gly
 1               5                  10                  15

Asp Arg Val Thr Ile Ser Cys Arg Ala Ser Gln Gly Ile Ile Asn Asp
                 20                  25                  30

Leu Gly Trp Tyr Gln Gln Lys Pro Gly Lys Ala Pro Lys Arg Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Phe Thr Ile Ser Ser Leu Gln Pro
 65                  70                  75                  80

Glu Asp Phe Ala Thr Tyr Tyr Cys Leu Gln His Asn Ser Tyr Pro Pro
                 85                  90                  95

Thr Phe Gly Gln Gly Thr Lys Val Glu Ile Lys
                100                 105

<210> SEQ ID NO 14
<211> LENGTH: 112
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 14

Asp Ile Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly His Thr Cys Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Val Gly Val Tyr Tyr Cys Met Gln Gly
                85                  90                  95

Thr His Trp Pro Leu Cys Ser Phe Gly Gln Gly Thr Lys Leu Glu Ile
            100                 105                 110

<210> SEQ ID NO 15
<211> LENGTH: 177
<212> TYPE: PRT
<213> ORGANISM: Homo sapiens

<400> SEQUENCE: 15

Met Arg Glu Arg Pro Arg Leu Gly Glu Asp Ser Ser Leu Ile Ser Leu
1               5                   10                  15

Phe Leu Gln Val Val Ala Phe Leu Ala Met Val Met Gly Thr His Thr
            20                  25                  30

Tyr Ser His Trp Pro Ser Cys Cys Pro Ser Lys Gly Gln Asp Thr Ser
        35                  40                  45

Glu Glu Leu Leu Arg Trp Ser Thr Val Pro Val Pro Pro Leu Glu Pro
    50                  55                  60

Ala Arg Pro Asn Arg His Pro Glu Ser Cys Arg Ala Ser Glu Asp Gly
65                  70                  75                  80

Pro Leu Asn Ser Arg Ala Ile Ser Pro Trp Arg Tyr Glu Leu Asp Arg
                85                  90                  95

Asp Leu Asn Arg Leu Pro Gln Asp Leu Tyr His Ala Arg Cys Leu Cys
            100                 105                 110

Pro His Cys Val Ser Leu Gln Thr Gly Ser His Met Asp Pro Arg Gly
        115                 120                 125

Asn Ser Glu Leu Leu Tyr His Asn Gln Thr Val Phe Tyr Arg Arg Pro
    130                 135                 140

Cys His Gly Glu Lys Gly Thr His Lys Gly Tyr Cys Leu Glu Arg Arg
145                 150                 155                 160

Leu Tyr Arg Val Ser Leu Ala Cys Val Cys Val Arg Pro Arg Val Met
                165                 170                 175

Gly

<210> SEQ ID NO 16
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 16

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Ala Asp Gly Thr Val Glu Leu Leu Ile
        35                  40                  45

Tyr Tyr Thr Ser Ser Leu His Ser Gly Val Pro Ser Arg Phe Ser Gly
50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Tyr
                85                  90                  95

Thr Phe Gly Gly Gly Thr Lys Leu Glu Ile Lys
            100                 105

<210> SEQ ID NO 17
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Asp Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Gly Gly Thr Ser Tyr Asn Gln Asn Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Glu Gly Tyr Asp Gly Tyr Leu Tyr Phe Ala Met Asp Tyr Trp
            100                 105                 110

Gly Gln Gly Thr Ser Val Thr Val Ser
        115                 120

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Ser Ile Gly Ser Tyr
1               5

<210> SEQ ID NO 19
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 19

Gln Ser Ile Ser Ser Tyr
1               5

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Ser Val Phe Leu Gly Ser Asn Asn Lys Asn Tyr
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Ser Val Leu Tyr Ser Ser Asn Asn Lys Asn Tyr
1               5                   10

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Asp Ile Asn Asn Tyr
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Ser Ile Ser Ser Tyr
1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Gly Ile Thr Asn Tyr
1               5
```

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Asn Ile Asn Ser His
1               5

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Asn Ile Leu Leu Thr Ser Ser Asn Lys Asn Tyr
1               5                   10

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Asp Ile Asn Ser Tyr
1               5

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Ser Val Leu Asp Ser Ser Asn Asn Lys Asn
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Ser Val Leu Asp Ser Ser Asn Asn Lys Asn Tyr
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 30

Gln Asn Val Leu Ile Thr Ser Asn Asn Lys Asn Tyr
1               5                   10

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Thr Ile Tyr Ser Tyr
1               5

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Ser Ile Leu Tyr Asn Ser Asp Asn Lys Asn Tyr
1               5                   10

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Asp Ile Ser Ser Phe
1               5

<210> SEQ ID NO 34
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala Ala Ser
1

<210> SEQ ID NO 35
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Trp Ala Ser
1
```

```
<210> SEQ ID NO 36
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Trp Ser Ser
1

<210> SEQ ID NO 37
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ser Thr Ser
1

<210> SEQ ID NO 38
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Thr Ala Ser
1

<210> SEQ ID NO 39
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Asp Ala Ser
1

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Gln Thr Tyr Ser Thr Pro Ile Thr
1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 41

Gln Gln Tyr Phe Ile Thr Pro Leu Thr
1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gln Gln Tyr Phe Ser Thr Pro Trp Thr
1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln Gln Thr Phe Ile Thr Pro Leu Thr
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Gln Ser Tyr Leu Thr Pro Leu Thr
1               5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gln Gln Tyr Gly Ser Ala Pro Trp Thr
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Gln Thr Tyr Ile Thr Pro Leu Thr
1               5
```

```
<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Gln Tyr Tyr Ile Thr Pro Phe Thr
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln His Leu Ser Ser Phe Pro Pro Thr
1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gln Gln Tyr Tyr Phe Thr Pro Leu Thr
1               5

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Gln Phe Tyr Asn Ser Pro Trp Thr
1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gln Gln Tyr Tyr Ser Thr Pro Phe Thr
1               5

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 52

Gln Gln Thr Tyr Ser Thr Pro Leu Thr
1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gln Gln Tyr Phe Phe Thr Pro Phe Thr
1               5

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gln Gln Val Asn Ser Tyr Pro Ile Thr
1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Phe Thr Phe Ser Asn Tyr Asp
1               5

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Phe Thr Phe Ser Asn Ala Trp
1               5

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Tyr Thr Phe Thr Ser Tyr Gly
1               5
```

-continued

```
<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Tyr Thr Phe Thr Asn Tyr Gly
1               5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Tyr Thr Phe Ser Ser Tyr Gly
1               5

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Gly Ser Ile Ser Ser His Tyr
1               5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Gly Ser Ile Ser Ser Tyr Phe
1               5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Gly Ser Ile Ser Asn Tyr Phe
1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 63

Gly Gly Ser Ile Ser Ser Tyr Tyr
1               5

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Gly Ser Ile Ser Asp Tyr Tyr
1               5

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gly Gly Ser Ile Asn Ser Tyr Tyr
1               5

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Gly Ser Ile Asn Ser Tyr Ser
1               5

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Ala Ser Ile Ser Asn Tyr Tyr
1               5

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Asp Phe Ala Phe Thr Thr Tyr Gly
1               5
```

```
<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Glu Tyr Thr Phe Ser Asn Tyr Gly
1               5

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ser Gly Ser Ile Arg Ser Ser Asn Tyr Tyr
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ile Glu Arg Lys Thr Asp Gly Gly Thr Thr
1               5                   10

<210> SEQ ID NO 72
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ala Arg Val Pro Ile Thr Gly Thr Thr Trp Phe Asp Pro
1               5                   10

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ile Tyr Tyr Ser Gly Ser Thr
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 74

Ile Phe Tyr Ser Gly Asn Thr
1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ile Asp Tyr Ser Gly Ser Thr
1               5

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ile Ser Ala Tyr Asn Asp Asn Thr
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Asn Tyr Asn Ser Gly Ser Thr
1               5

<210> SEQ ID NO 78
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ile Ser Ala Tyr Asn Gly Asn Thr
1               5

<210> SEQ ID NO 79
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ile Gly Ala Tyr Ser Gly Phe Thr
1               5
```

```
<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ile Tyr Tyr Ser Gly Asn Thr
1               5

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ile Tyr Asn Ser Glu Asn Thr
1               5

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ile Gly Ser Ala Gly Asp Thr
1               5

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Thr Thr Val Gly Pro Tyr Ser Val Pro Phe Asp Tyr
1               5                   10

<210> SEQ ID NO 84
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ala Arg Val Pro Ile Thr Gly Thr Thr Trp Phe Asp Pro
1               5                   10

<210> SEQ ID NO 85
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 85

Ala Arg Val Arg Phe Ser Asp Tyr Glu Leu Asn Trp Phe Asp Pro
1               5                   10                  15

<210> SEQ ID NO 86
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ala Arg Val Pro Leu Gln Trp Phe Gly Glu Ser Phe
1               5                   10

<210> SEQ ID NO 87
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ala Arg Val Gly Thr Gly Thr Asp Ser Tyr Phe Asp Phe
1               5                   10

<210> SEQ ID NO 88
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ala Arg Val Pro Ile Thr Gly Thr Thr Ser Ser Phe Asp Phe
1               5                   10

<210> SEQ ID NO 89
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ala Arg His Asp Tyr Asn Asp Tyr Glu Leu Asn Tyr Phe Asp Leu
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ala Arg Gln Glu Ile Ile Asn Phe Glu Leu Asn Trp Phe Asp Pro
1               5                   10                  15
```

```
<210> SEQ ID NO 91
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ala Arg Gly Tyr Asn Trp Asn Tyr Glu Ile Ala Trp Phe Asp Pro
1               5                   10                  15

<210> SEQ ID NO 92
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ala Arg Asp Pro Asp Tyr Cys Ser Ser Asn Thr Cys Ser Asp Ala Phe
1               5                   10                  15

Asp Leu

<210> SEQ ID NO 93
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ala Arg His Tyr Phe Asp Ser Gly Thr Tyr Glu Leu Gly Tyr
1               5                   10

<210> SEQ ID NO 94
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ala Arg Asp Gly Tyr Ser Ser Ser Ser Gly Phe Tyr Tyr Phe Gly Met
1               5                   10                  15

<210> SEQ ID NO 95
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ala Arg Gly Val Ile Trp Asn Tyr Glu Leu Arg Glu Phe
1               5                   10

<210> SEQ ID NO 96
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 96

Ala Arg Gln Gly Tyr Ser Asp Tyr Glu Leu Asn Trp Phe Asp Pro
1               5                   10                  15

<210> SEQ ID NO 97
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ala Arg Thr Tyr Asn Trp Asn Tyr Glu Ile Gly Ala Met
1               5                   10

<210> SEQ ID NO 98
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ala Arg His Asp Ser Asp Tyr Glu Leu Tyr Gly Met Asp Val
1               5                   10

<210> SEQ ID NO 99
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ala Arg Gly Asp Asn Trp Asn Tyr Val Ser Trp Phe Phe
1               5                   10

<210> SEQ ID NO 100
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

His Lys Cys Asp Ile Thr Leu Gln Glu Ile Ile Lys Thr Leu Asn Ser
1               5                   10                  15

Leu Thr Glu Gln Lys Thr Leu Cys Thr Glu Leu Thr Val Thr Asp Ile
            20                  25                  30

Phe Ala Ala Ser Lys Asn Thr Thr Glu Lys Glu Thr Phe Cys Arg Ala
        35                  40                  45

Ala Thr Val Leu Arg Gln Phe Tyr Ser His His Glu Lys Asp Thr Arg
    50                  55                  60

Cys Leu Gly Ala Thr Ala Gln Gln Phe His Arg His Lys Gln Leu Ile
65                  70                  75                  80

Arg Phe Leu Lys Arg Leu Asp Arg Asn Leu Trp Gly Leu Ala Gly Leu
                85                  90                  95
```

Asn Ser Cys Pro Val Lys Glu Ala Asn Gln Ser Thr Leu Glu Asn Phe
            100                 105                 110

Leu Glu Arg Leu Lys Thr Ile Met Arg Glu Lys
        115                 120

<210> SEQ ID NO 101
<211> LENGTH: 444
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101
atgggcctga ccagccagct gctgccccc ctgttcttcc tgctggcctg cgccggcaac      60
ttcgtgcacg ccacaagtg cgacatcacc ctgcaggaga tcatcaagac cctgaacagc     120
ctgaccgagc agaagaccct gtgcaccgag ctgaccgtga ccgacatctt cgccgccagc    180
aagaacacca ccgagaagga gaccttctgc agagccgcca ccgtgctgag acagttctac    240
agccaccacg agaaggacac cagatgcctg ggcgccaccg cccagcagtt ccacagacac    300
aagcagctga tcagattcct gaagagactg acagaaaacc tgtggggcct ggccggcctg    360
aacagctgcc ccgtgaagga ggccaaccag agcaccctgg agaacttcct ggagagactg    420
aagaccatca tgagagagaa gtga                                           444

<210> SEQ ID NO 102
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ser Ala Ser Gln Gly Ile Ser Asn Tyr Leu Asn
1               5                   10

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Tyr Thr Ser Ser Leu His Ser
1               5

<210> SEQ ID NO 104
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gln Gln Tyr Leu Ala Phe Pro Tyr Thr Phe
1               5                   10

```
<210> SEQ ID NO 105
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gly Tyr Thr Met Asn
1               5

<210> SEQ ID NO 106
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Leu Ile Asn Pro Tyr Asn Gly Gly Thr Ser Tyr Asn Gln Asn Phe Lys
1               5                   10                  15

Gly

<210> SEQ ID NO 107
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Glu Asp Tyr Asp Gly Tyr Leu Tyr Phe Ala Met Tyr
1               5                   10

<210> SEQ ID NO 108
<211> LENGTH: 16
<212> TYPE: PRT
<213> ORGANISM: Homo sapiens

<400> SEQUENCE: 108

Ser Glu Asp Gly Pro Leu Asn Ser Arg Ala Ile Ser Pro Trp Arg Tyr
1               5                   10                  15

<210> SEQ ID NO 109
<211> LENGTH: 19
<212> TYPE: PRT
<213> ORGANISM: Homo sapiens

<400> SEQUENCE: 109

Asp Leu Asn Arg Leu Pro Gln Asp Leu Tyr His Ala Arg Cys Leu Cys
1               5                   10                  15

Pro His Cys

<210> SEQ ID NO 110
<211> LENGTH: 7
<212> TYPE: PRT
<213> ORGANISM: Homo sapiens

<400> SEQUENCE: 110

Arg Leu Tyr Arg Val Ser Leu
1               5
```

```
<210> SEQ ID NO 111
<211> LENGTH: 5
<212> TYPE: PRT
<213> ORGANISM: Unknown
<220> FEATURE:
<223> OTHER INFORMATION: Description of Unknown:
      hydrophobic motif sequence

<400> SEQUENCE: 111

Ala Arg Ile Asn Val
1               5

<210> SEQ ID NO 112
<211> LENGTH: 11
<212> TYPE: PRT
<213> ORGANISM: Unknown
<220> FEATURE:
<223> OTHER INFORMATION: Description of Unknown:
      C-terminal tag sequence

<400> SEQUENCE: 112

Ala Ala Asn Asp Glu Asn Tyr Ala Leu Ala Ala
1               5                   10

<210> SEQ ID NO 113
<211> LENGTH: 9
<212> TYPE: PRT
<213> ORGANISM: Unknown
<220> FEATURE:
<223> OTHER INFORMATION: Description of Unknown:
      cyclin sequence
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid

<400> SEQUENCE: 113

Arg Xaa Ala Leu Gly Xaa Ile Xaa Asn
1               5

<210> SEQ ID NO 114
<211> LENGTH: 10
<212> TYPE: PRT
<213> ORGANISM: Unknown
<220> FEATURE:
<223> OTHER INFORMATION: Description of Unknown:
      isocitrate lyase sequence

<400> SEQUENCE: 114

Lys Thr Lys Arg Asn Tyr Ser Ala Arg Asp
1               5                   10

<210> SEQ ID NO 115
<211> LENGTH: 858
<212> TYPE: DNA
<213> ORGANISM: Artificial Sequence
<220> FEATURE:
<223> OTHER INFORMATION: Description of Artificial Sequence: Synthetic
      polynucleotide
```

-continued

```
<400> SEQUENCE: 115
atgctgctgg tgctgctgat cctggccgcc agctgcagga gcgccctgcc tagggagcct     60
accatccagt gcggcagcga gaccggccct agccctgagt ggatggtgca gcacaccctg    120
acccctggcg acctgaggga cctgcaggtg gagctggtga agaccagcgt ggccgccgag    180
gagttcagca tcctgatgaa catcagcatc ctgagggccg acgccagcat caggctgctg    240
aaggccacca agatctgcgt gagcggcaag aacaacatga acagctacag ctgcgtgagg    300
tgcaactaca ccgaggcctt ccagagccag accaggccta gcggcggcaa gtggaccttc    360
agctacgtgg gcttccctgt ggagctgagc accctgtacc tgatcagcgc ccacaacatc    420
cctaacgcca acatgaacga ggacagccct agcctgagcg tgaacttcac cagccctggc    480
tgcctgaacc acgtgatgaa gtacaagaag cagtgcaccg aggccggcag cctgtgggac    540
cctgacatca ccgcctgcaa gaagaacgag aagatggtgg aggtgaactt caccaccaac    600
cctctgggca acaggtacac catcctgatc cagagggaca ccaccctggg cttcagcagg    660
gtgctggaga acaagctgat gaggaccagc gtggccatcc ctgtgaccga ggagagcgag    720
ggcgccgtgg tgcagctgac cccttacctg cacacctgcg gcaacgactg catcaggagg    780
gagggcaccg tggtgctgtg cagcgagacc agcgccccta tccctcctga cgacaacagg    840
aggatgctgg gcggctga                                                  858
```